(12) United States Patent
Shaolian et al.

(10) Patent No.: US 8,337,556 B2
(45) Date of Patent: Dec. 25, 2012

(54) CURABLE MEDIA FOR IMPLANTABLE MEDICAL DEVICE

(75) Inventors: Samuel M. Shaolian, Newport Beach, CA (US); George P. Teitelbaum, Santa Monica, CA (US); Thanh Van Nguyen, Irvine, CA (US); To V. Pham, Trabuco Canyon, CA (US); Richard H. Estes, Buford, GA (US)

(73) Assignee: SDGI Holdings, Inc., Wilmington, DE (US)

( * ) Notice: Subject to any disclaimer, the term of this patent is extended or adjusted under 35 U.S.C. 154(b) by 1686 days.

(21) Appl. No.: 11/056,971

(22) Filed: Feb. 11, 2005

(65) Prior Publication Data

US 2005/0149022 A1    Jul. 7, 2005

Related U.S. Application Data

(60) Division of application No. 10/327,706, filed on Dec. 20, 2002, now Pat. No. 6,875,212, which is a continuation-in-part of application No. 10/161,554, filed on May 31, 2002, now Pat. No. 6,964,667, which is a continuation-in-part of application No. 09/976,459, filed on Oct. 10, 2001, now Pat. No. 6,749,614, which is a continuation-in-part of application No. 09/943,636, filed on Aug. 29, 2001, now Pat. No. 6,899,713, which is a continuation-in-part of application No. 09/747,066, filed on Dec. 21, 2000, now Pat. No. 6,821,277.

(60) Provisional application No. 60/213,385, filed on Jun. 23, 2000.

(51) Int. Cl.
    *A61B 17/88* (2006.01)

(52) U.S. Cl. ..................................... 623/17.12; 606/262
(58) Field of Classification Search ................ 623/17.12, 623/901; 606/92–94, 90, 105; 156/326, 156/330, 331.1; 523/116, 118, 400, 406
See application file for complete search history.

(56) References Cited

U.S. PATENT DOCUMENTS

| | | | |
|---|---|---|---|
| 2,267,925 A | 12/1941 | Johnston | |
| 3,155,091 A | 11/1964 | Nissenbaum et al. | |
| 3,834,394 A | 9/1974 | Hunter et al. | |
| 3,875,595 A * | 4/1975 | Froning | 623/17.12 |

(Continued)

FOREIGN PATENT DOCUMENTS

DE    3924990    2/1991

(Continued)

OTHER PUBLICATIONS

International Search Report for European Application No. 00 98 9371 (the European counterpart of the parent application) mailed on Jan. 2, 2007.

(Continued)

*Primary Examiner* — Alvin Stewart
*Assistant Examiner* — Tara Carter

(57) ABSTRACT

A subcutaneously formed in place orthopedic fixation device is provided, such as for fixation of the spine or other bone or bones. The device comprises an inflatable member, such as a tubular balloon. The balloon is positioned at a treatment site in the body while in a flexible, low crossing profile configuration. The balloon is thereafter inflated with a hardenable epoxy media comprising one or more epoxy compounds and one or more amine curing compounds that cures rapidly in place with low to moderate exotherm. Methods and delivery structures are also disclosed.

23 Claims, 39 Drawing Sheets

U.S. PATENT DOCUMENTS

| | | |
|---|---|---|
| 3,877,424 A | 4/1975 | Murray |
| 4,041,939 A | 8/1977 | Hall |
| 4,064,566 A | 12/1977 | Fletcher et al. |
| 4,085,757 A | 4/1978 | Pevsner |
| 4,289,123 A | 9/1981 | Dunn |
| 4,327,734 A | 5/1982 | White, Jr. |
| 4,341,218 A | 7/1982 | Ü |
| 4,346,712 A | 8/1982 | Handa et al. |
| 4,364,392 A | 12/1982 | Strother et al. |
| 4,383,879 A * | 5/1983 | Le Du et al. ............... 156/307.7 |
| 4,441,495 A | 4/1984 | Hicswa |
| 4,471,779 A | 9/1984 | Antoshkiw et al. |
| 4,517,979 A | 5/1985 | Pecenka |
| 4,545,367 A | 10/1985 | Tucci |
| 4,547,168 A | 10/1985 | Blacksberg et al. |
| 4,612,384 A | 9/1986 | Omura et al. |
| 4,638,803 A | 1/1987 | Rand |
| RE32,348 E | 2/1987 | Pevsner |
| 4,643,733 A | 2/1987 | Becker |
| 4,648,388 A | 3/1987 | Steffee |
| 4,686,973 A | 8/1987 | Frisch |
| 4,693,721 A | 9/1987 | Ducheyne |
| 4,714,721 A | 12/1987 | Franek et al. |
| 4,743,260 A | 5/1988 | Burton |
| 4,772,287 A | 9/1988 | Ray et al. |
| 4,772,289 A | 9/1988 | Anzinger et al. |
| 4,819,637 A | 4/1989 | Dormandy, Jr. et al. |
| 4,832,680 A | 5/1989 | Haber et al. |
| 4,887,595 A | 12/1989 | Heinig et al. |
| 4,888,022 A | 12/1989 | Huebsch |
| 4,892,550 A | 1/1990 | Huebsch |
| 4,893,618 A | 1/1990 | Herzberg |
| 4,904,260 A | 2/1990 | Ray et al. |
| 4,963,151 A | 10/1990 | Ducheyne et al. |
| 4,998,936 A | 3/1991 | Mehdian |
| 5,000,165 A | 3/1991 | Watanabe |
| 5,002,556 A | 3/1991 | Ishida et al. |
| 5,002,576 A | 3/1991 | Fuhrmann et al. |
| 5,030,220 A | 7/1991 | Howland |
| 5,037,445 A | 8/1991 | Sander et al. |
| 5,084,049 A | 1/1992 | Asher et al. |
| 5,084,051 A | 1/1992 | Törmälä |
| 5,106,360 A | 4/1992 | Ishiwara et al. |
| 5,108,404 A | 4/1992 | Scholten et al. |
| 5,139,499 A | 8/1992 | Small et al. |
| 5,141,521 A | 8/1992 | Wenner |
| 5,146,933 A | 9/1992 | Boyd |
| 5,165,919 A | 11/1992 | Sasaki et al. |
| 5,171,279 A | 12/1992 | Mathews |
| 5,171,280 A | 12/1992 | Baumgartner |
| 5,176,680 A | 1/1993 | Vignaud et al. |
| 5,181,921 A | 1/1993 | Makita et al. |
| 5,190,540 A | 3/1993 | Lee |
| 5,195,970 A | 3/1993 | Gahara |
| 5,222,970 A | 6/1993 | Reeves |
| 5,242,443 A | 9/1993 | Kambin |
| 5,242,444 A | 9/1993 | MacMillan |
| 5,304,123 A | 4/1994 | Atala et al. |
| 5,306,275 A | 4/1994 | Bryan |
| 5,320,529 A | 6/1994 | Pompa |
| 5,324,261 A | 6/1994 | Amundson et al. |
| 5,342,361 A | 8/1994 | Yuan et al. |
| 5,344,398 A | 9/1994 | Hara |
| 5,357,983 A | 10/1994 | Mathews |
| 5,366,490 A | 11/1994 | Edwards et al. |
| 5,397,363 A | 3/1995 | Gelbarb |
| 5,464,407 A | 11/1995 | Mcguire |
| 5,468,245 A | 11/1995 | Vargas, III |
| 5,470,336 A | 11/1995 | Ling et al. |
| 5,474,551 A | 12/1995 | Finn et al. |
| 5,484,418 A | 1/1996 | Quiachon et al. |
| 5,486,174 A | 1/1996 | Fournet-Fayard et al. |
| 5,496,322 A | 3/1996 | Mathews |
| 5,520,689 A | 5/1996 | Schlapfer et al. |
| 5,529,653 A | 6/1996 | Glastra |
| 5,549,679 A * | 8/1996 | Kuslich ............... 623/17.12 |
| 5,554,191 A | 9/1996 | Lahille et al. |
| 5,556,429 A | 9/1996 | Felt |
| 5,562,661 A | 10/1996 | Yoshimi et al. |
| 5,562,736 A * | 10/1996 | Ray et al. ............... 606/86 A |
| 5,569,248 A | 10/1996 | Mathews |
| 5,571,189 A | 11/1996 | Kuslich |
| 5,584,887 A | 12/1996 | Kambin |
| 5,591,165 A | 1/1997 | Jackson |
| 5,591,167 A | 1/1997 | Laurain et al. |
| 5,591,199 A | 1/1997 | Porter et al. |
| 5,593,408 A | 1/1997 | Gayet et al. |
| 5,649,925 A | 7/1997 | Alacreu |
| 5,653,736 A | 8/1997 | Glastra |
| 5,658,286 A * | 8/1997 | Sava ............... 606/279 |
| 5,658,289 A | 8/1997 | Boucher et al. |
| 5,681,872 A | 10/1997 | Erbe |
| 5,702,373 A | 12/1997 | Samson |
| 5,720,751 A | 2/1998 | Jackson |
| 5,728,097 A | 3/1998 | Mathews |
| 5,733,260 A | 3/1998 | DeMaio et al. |
| 5,752,955 A | 5/1998 | Errico |
| 5,772,661 A | 6/1998 | Michelson |
| 5,772,681 A | 6/1998 | Leoni |
| 5,776,099 A | 7/1998 | Tremulis |
| 5,779,672 A | 7/1998 | Dormandy, Jr. |
| 5,792,044 A | 8/1998 | Foley et al. |
| 5,792,106 A | 8/1998 | Mische |
| 5,795,353 A | 8/1998 | Felt |
| 5,800,435 A | 9/1998 | Errico et al. |
| 5,827,289 A | 10/1998 | Reiley et al. |
| 5,837,752 A | 11/1998 | Shastri et al. |
| 5,840,059 A | 11/1998 | March et al. |
| 5,865,848 A | 2/1999 | Baker |
| 5,879,713 A | 3/1999 | Roth et al. |
| 5,888,220 A * | 3/1999 | Felt et al. ............... 128/898 |
| 5,899,939 A | 5/1999 | Boyce et al. |
| 5,910,142 A | 6/1999 | Tatar |
| 5,914,356 A | 6/1999 | Erbe |
| 5,938,663 A | 8/1999 | Petreto |
| 5,972,015 A | 10/1999 | Scribner et al. |
| 5,980,253 A | 11/1999 | Oxman et al. |
| 5,980,522 A | 11/1999 | Koros et al. |
| 6,025,406 A | 2/2000 | Oxman et al. |
| 6,033,406 A | 3/2000 | Mathews |
| 6,042,380 A | 3/2000 | De Rowe |
| 6,043,295 A | 3/2000 | Oxman et al. |
| 6,048,343 A | 4/2000 | Mathis et al. |
| 6,048,346 A | 4/2000 | Reiley et al. |
| 6,066,154 A | 5/2000 | Reiley et al. |
| 6,080,801 A | 6/2000 | Draenert et al. |
| 6,099,528 A | 8/2000 | Saurat |
| 6,102,912 A | 8/2000 | Cazin et al. |
| 6,106,530 A | 8/2000 | Harada |
| 6,123,707 A | 9/2000 | Wagner |
| 6,126,689 A | 10/2000 | Brett |
| 6,127,597 A | 10/2000 | Beyar et al. |
| 6,140,452 A | 10/2000 | Felt et al. |
| 6,149,655 A | 11/2000 | Constantz et al. |
| 6,159,012 A | 12/2000 | Oxman et al. |
| 6,174,334 B1 | 1/2001 | Suddaby |
| 6,175,758 B1 | 1/2001 | Kambin |
| 6,176,882 B1 | 1/2001 | Bierdermann et al. |
| 6,183,515 B1 | 2/2001 | Barlow et al. |
| 6,187,048 B1 | 2/2001 | Milner et al. |
| 6,206,922 B1 | 3/2001 | Zdeblick et al. |
| 6,226,548 B1 | 5/2001 | Foley et al. |
| 6,235,028 B1 | 5/2001 | Brumfield et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,270,515 B1 | 8/2001 | Linden et al. |
| 6,280,456 B1 | 8/2001 | Scribner |
| 6,293,960 B1 | 9/2001 | Ken |
| 6,296,643 B1 | 10/2001 | Hopf et al. |
| 6,296,644 B1 | 10/2001 | Saurat et al. |
| 6,306,177 B1 | 10/2001 | Felt et al. |
| 6,309,421 B1 | 10/2001 | Pisharodi |
| 6,332,894 B1 | 12/2001 | Stalcup et al. |
| 6,336,930 B1 | 1/2002 | Stalcup et al. |
| 6,379,329 B1 | 4/2002 | Naglreiter et al. |
| 6,395,034 B1 | 5/2002 | Suddaby |

| | | |
|---|---|---|
| 6,402,784 B1 | 6/2002 | Wardlaw |
| 6,425,923 B1 | 7/2002 | Stalcup et al. |
| 6,443,988 B2 | 9/2002 | Felt et al. |
| 6,447,514 B1 | 9/2002 | Stalcup |
| 6,530,926 B1 | 3/2003 | Davison |
| 6,530,929 B1 | 3/2003 | Justis et al. |
| 6,547,804 B2 | 4/2003 | Porter et al. |
| 6,558,386 B1 | 5/2003 | Cragg |
| 6,558,390 B2 | 5/2003 | Cragg |
| 6,666,870 B2 | 12/2003 | Dixon et al. |
| 6,726,691 B2 | 4/2004 | Osorio et al. |
| 6,733,533 B1 | 5/2004 | Lozier |
| 6,749,614 B2 | 6/2004 | Teitelbaum et al. |
| 6,805,695 B2 | 10/2004 | Keith et al. |
| 6,821,277 B2 | 11/2004 | Teitelbaum |
| 6,893,466 B2 | 5/2005 | Trieu |
| 6,899,713 B2 | 5/2005 | Shaolian et al. |
| 6,932,843 B2 | 8/2005 | Smith et al. |
| 6,958,077 B2 | 10/2005 | Suddaby |
| 6,964,667 B2 | 11/2005 | Shaolian et al. |
| 6,969,405 B2 | 11/2005 | Suddaby |
| 6,987,136 B2 | 1/2006 | Erbe et al. |
| 7,001,431 B2 | 2/2006 | Bao et al. |
| 7,004,971 B2 | 2/2006 | Serhan et al. |
| 7,077,865 B2 | 7/2006 | Bao et al. |
| 2001/0004710 A1 | 6/2001 | Felt et al. |
| 2002/0022764 A1 | 2/2002 | Smith et al. |
| 2002/0045904 A1 | 4/2002 | Fuss et al. |
| 2002/0068975 A1 | 6/2002 | Teitelbaum et al. |
| 2002/0082598 A1 | 6/2002 | Teitelbaum |
| 2002/0082600 A1 | 6/2002 | Shaolian et al. |
| 2002/0082601 A1 | 6/2002 | Toyama et al. |
| 2002/0095158 A1 | 7/2002 | Dixon et al. |
| 2002/0123750 A1 | 9/2002 | Eisermann et al. |
| 2002/0161368 A1 | 10/2002 | Foley et al. |
| 2002/0165572 A1 | 11/2002 | Saadat |
| 2002/0198526 A1 | 12/2002 | Shaolian et al. |
| 2003/0028251 A1 | 2/2003 | Mathews |
| 2003/0040800 A1 | 2/2003 | Li et al. |
| 2003/0060826 A1 | 3/2003 | Foley et al. |
| 2003/0087984 A1 | 5/2003 | Erbe et al. |
| 2003/0125739 A1 | 7/2003 | Bagga et al. |
| 2003/0144624 A1 | 7/2003 | Barbut |
| 2003/0144737 A1 | 7/2003 | Sherman |
| 2003/0167967 A1 | 9/2003 | Narhhi et al. |
| 2003/0171451 A1 | 9/2003 | White et al. |
| 2003/0195547 A1 | 10/2003 | Scribner et al. |
| 2003/0220666 A1 | 11/2003 | Mirigian et al. |
| 2004/0006341 A1 | 1/2004 | Shaolian et al. |
| 2004/0082954 A1 | 4/2004 | Teitelbaum et al. |
| 2004/0087950 A1 | 5/2004 | Teitelbaum |
| 2004/0092948 A1 | 5/2004 | Stevens et al. |
| 2004/0215193 A1 | 10/2004 | Shaolian et al. |
| 2004/0230309 A1 | 11/2004 | DiMauro et al. |
| 2005/0010220 A1 | 1/2005 | Casutt et al. |
| 2005/0027257 A1 | 2/2005 | Davey |
| 2005/0090901 A1 | 4/2005 | Studer |
| 2005/0273178 A1 | 12/2005 | Boyan et al. |
| 2006/0106459 A1 | 5/2006 | Truckai et al. |
| 2006/0173464 A1 | 8/2006 | Ellman et al. |
| 2006/0293750 A1 | 12/2006 | Sherman et al. |
| 2007/0067043 A1 | 3/2007 | Dericks |
| 2007/0073292 A1 | 3/2007 | Kohm et al. |
| 2007/0150061 A1 | 6/2007 | Trieu |

FOREIGN PATENT DOCUMENTS

| | | |
|---|---|---|
| DE | 197 26 754 A1 | 2/1999 |
| EP | 1132053 | 9/2001 |
| EP | 1421921 | 5/2004 |
| GB | 2086231 | 5/1982 |
| JP | 2005028046 | 2/2005 |
| NL | 9001858 | 3/1992 |
| SU | 839513 | 5/1981 |
| SU | 1745231 A1 | 7/1992 |
| WO | WO 8909031 | 10/1989 |
| WO | WO 97/30666 | 8/1997 |
| WO | WO 97/38639 | 10/1997 |
| WO | WO 99/09902 | 3/1999 |
| WO | WO 99/15097 | 4/1999 |
| WO | WO 99/26549 | 6/1999 |
| WO | WO 00/44288 | 8/2000 |
| WO | WO 02/00126 | 1/2002 |
| WO | WO 2004/017857 | 3/2004 |
| WO | WO 2004/058045 | 7/2004 |
| WO | WO 2006/063083 | 6/2006 |
| WO | WO 2006/074410 | 7/2006 |

OTHER PUBLICATIONS

Bennett, Gregory J., Lumbosacral Stabilization Using Screw Fixation Techniques, *Neurosurgery*, McGraw-Hill Health Professions Division, Second Edition, vol. II, pp. 3027-3035.

Kyphon Inc., *Kypohon: Fragility Fracture Management: About Kyphon*, 2000.

Müller, Adolf, M.D. et al. A Keyhole Approach for Endoscopically Assisted Pedicle Screw Fixation in Lumbar Spine Instability, *Neurosurgery*, vol. 47, No. 1, Jul. 2000, pp. 85-96.

Wilkins, Robert H., M.D. et al., *Neurosurgery*, 2nd Edition, vol. 1, pp. 3027-3035.

International Search Report for Aplication No. PCT/US2000/34855 (the PCT counterpart of the parent application).

Katsuya Goto et al., "Permanent Inflation of Detachable Balloons with a Low-Viscosity, Hydrophilic Polymerizing System", Radiology, Dec. 1988; 169:787-790.

European Search Report for Application No. PCT/US0227516 mailed on Aug. 25, 2009.

* cited by examiner

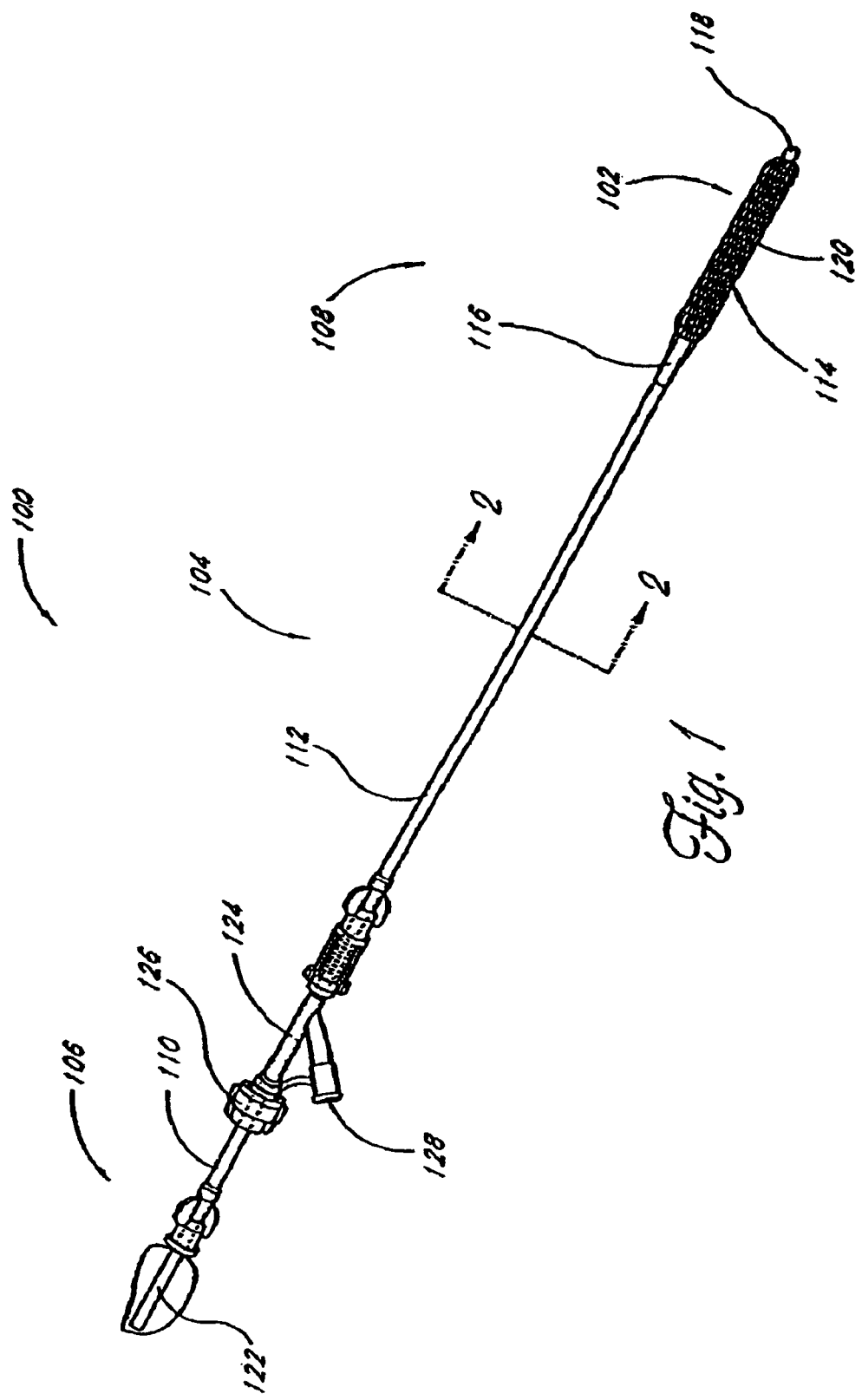

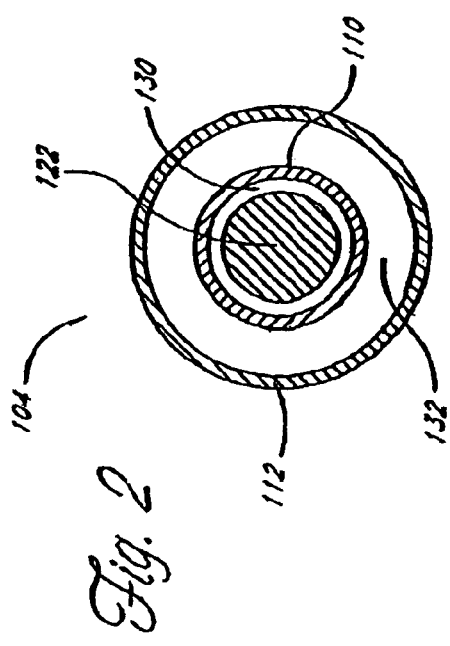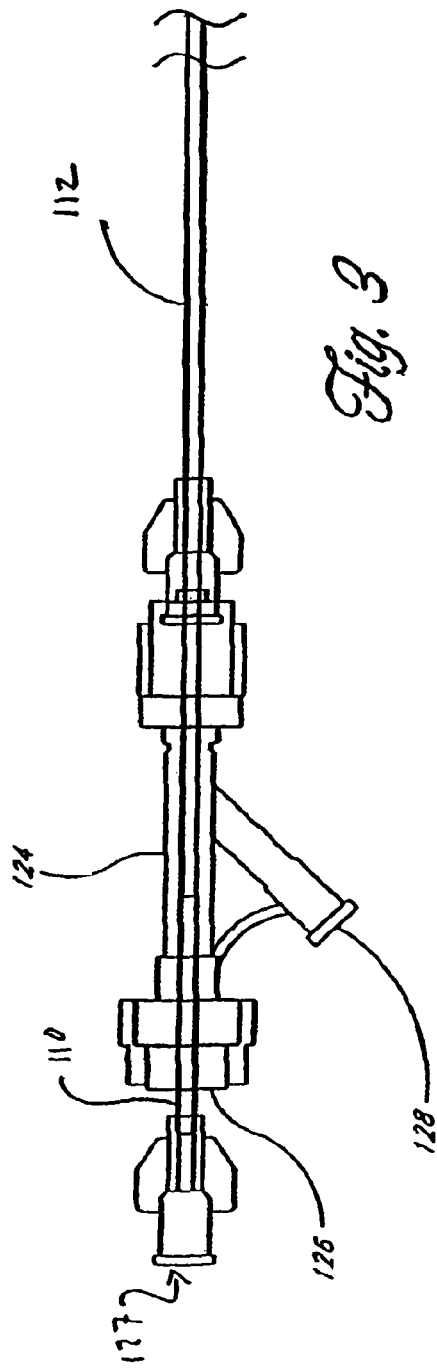

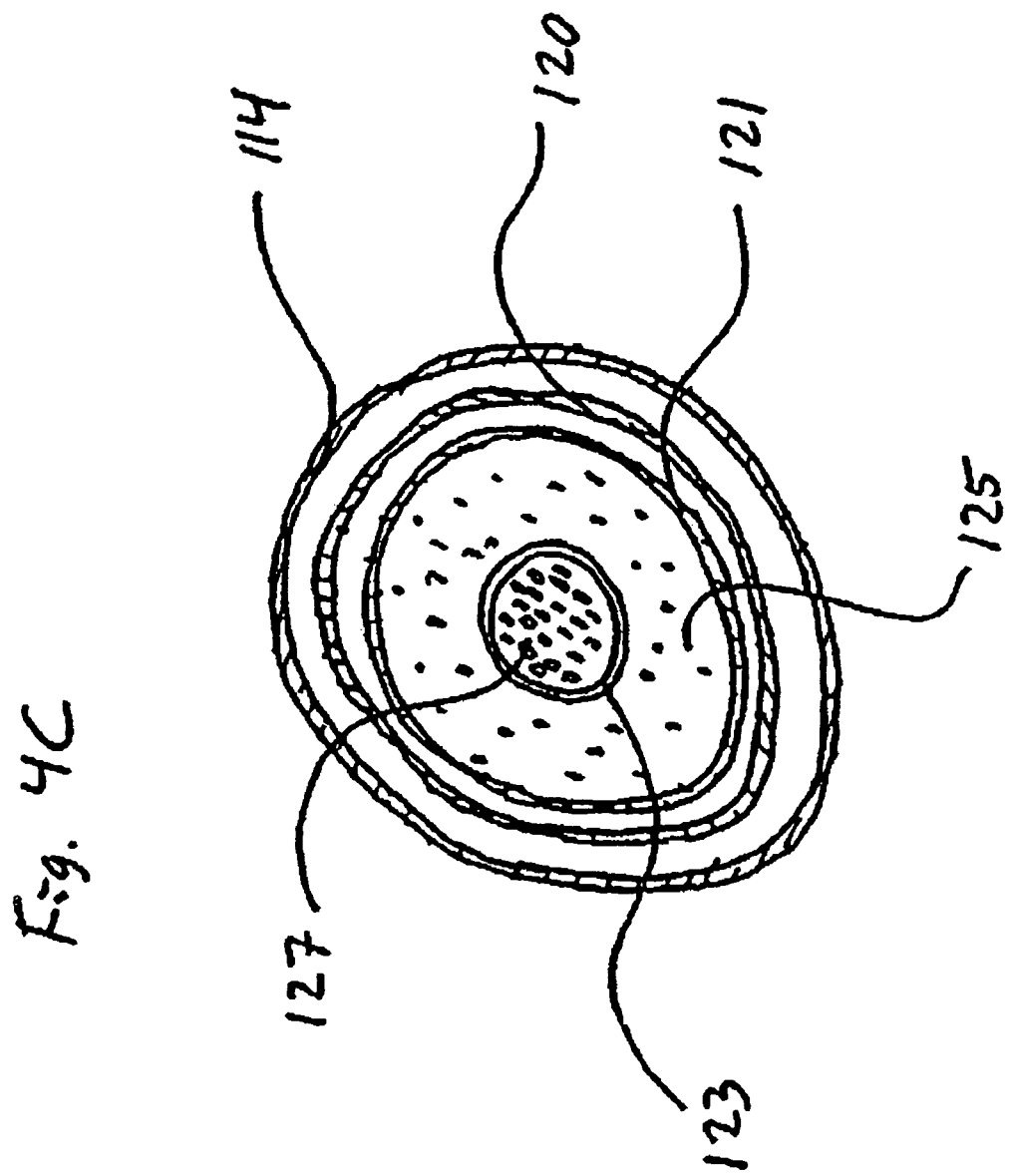

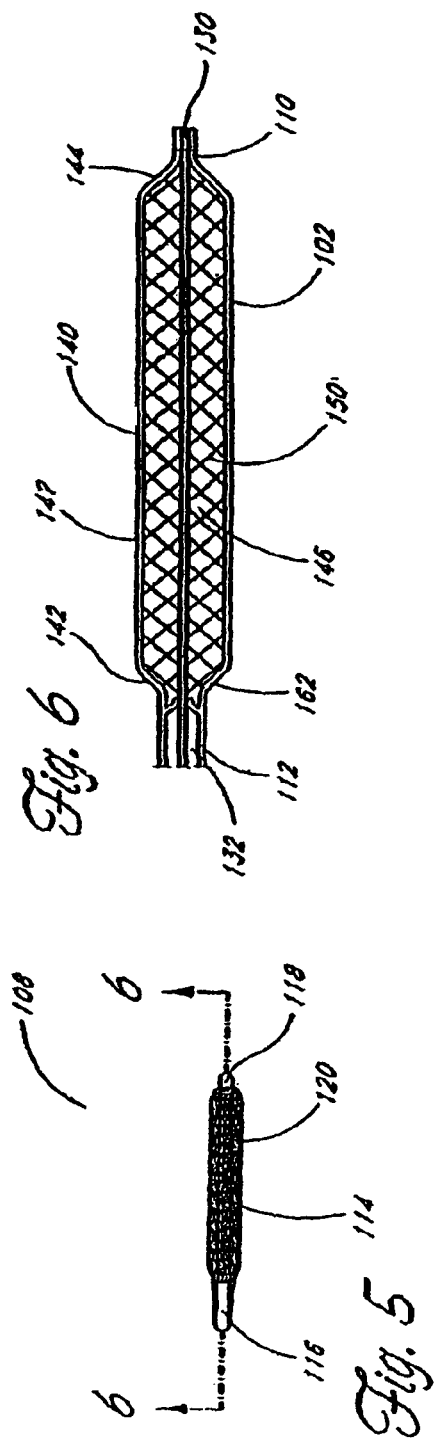
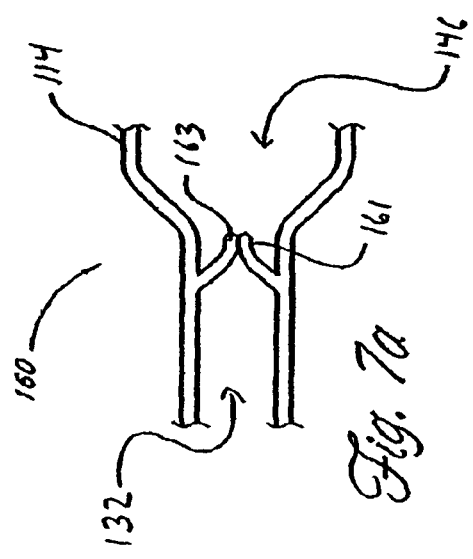

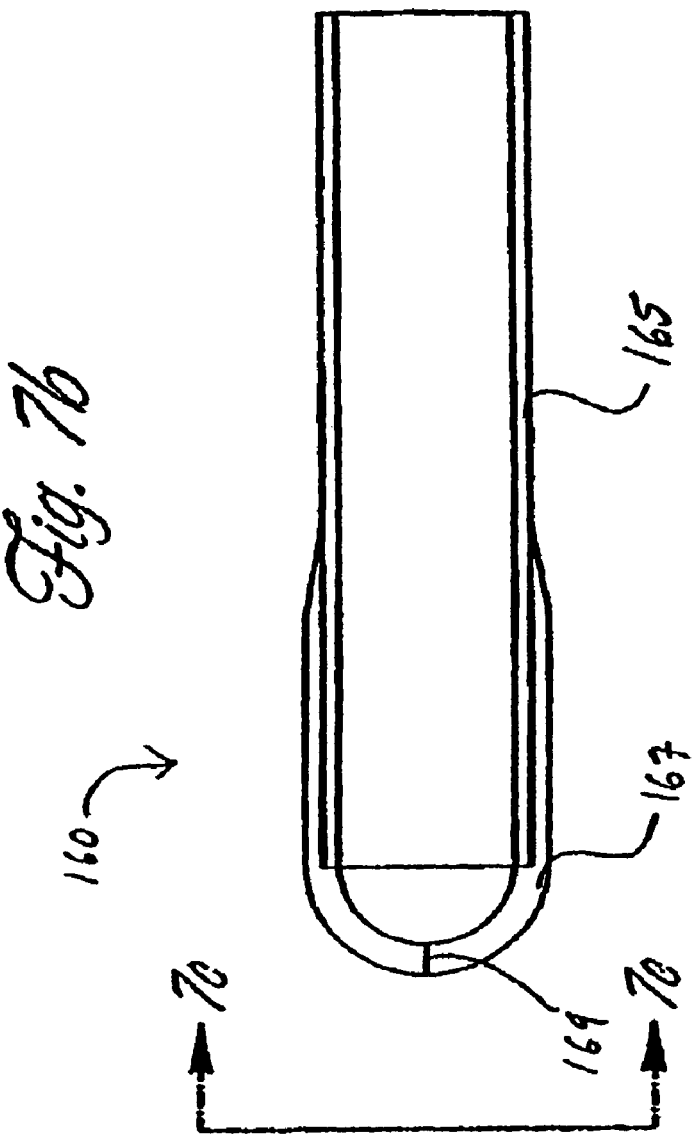
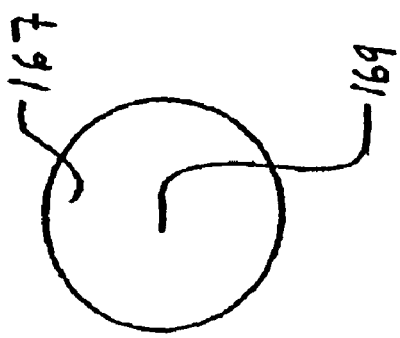

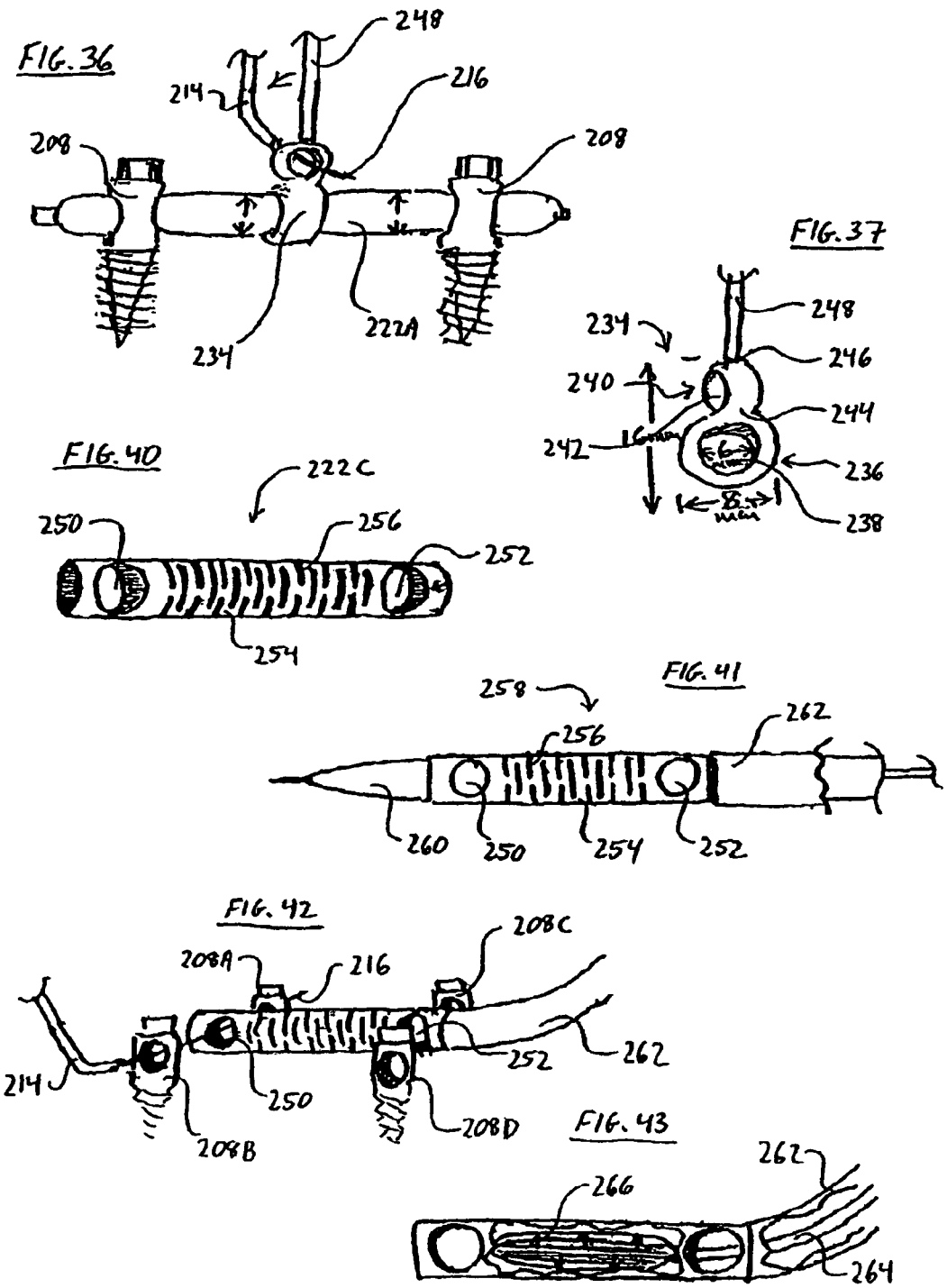

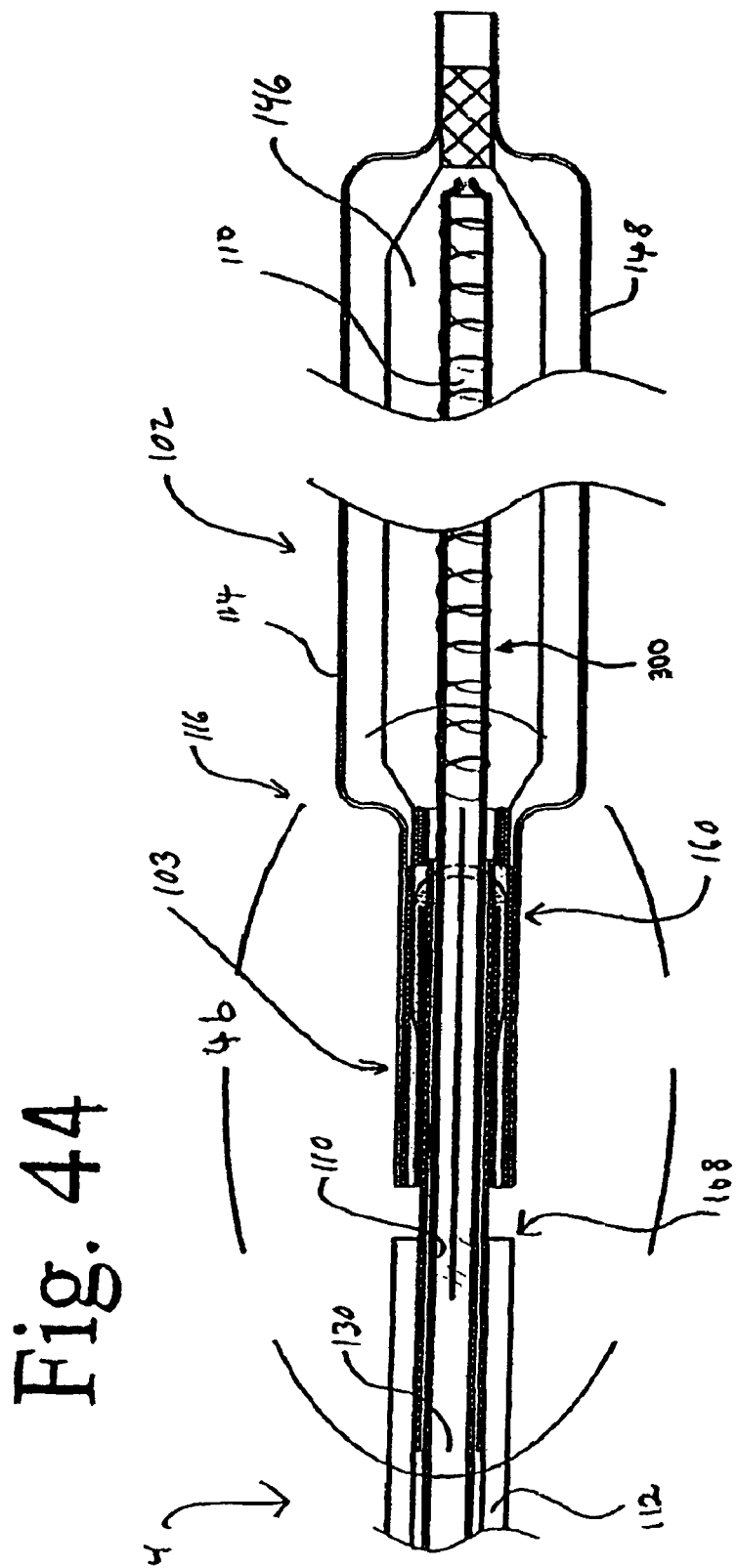

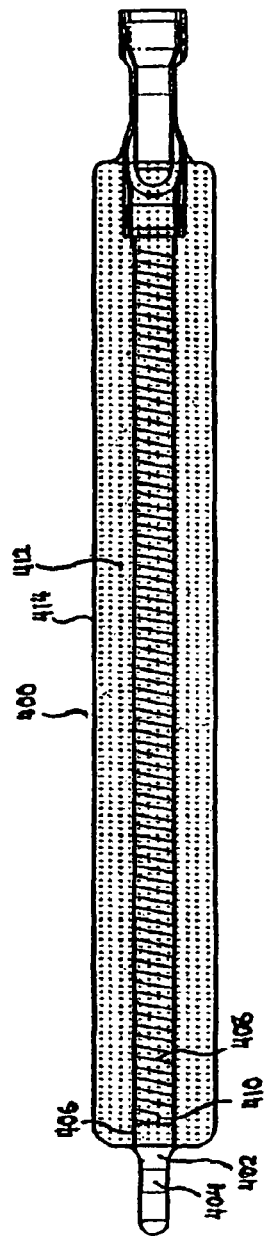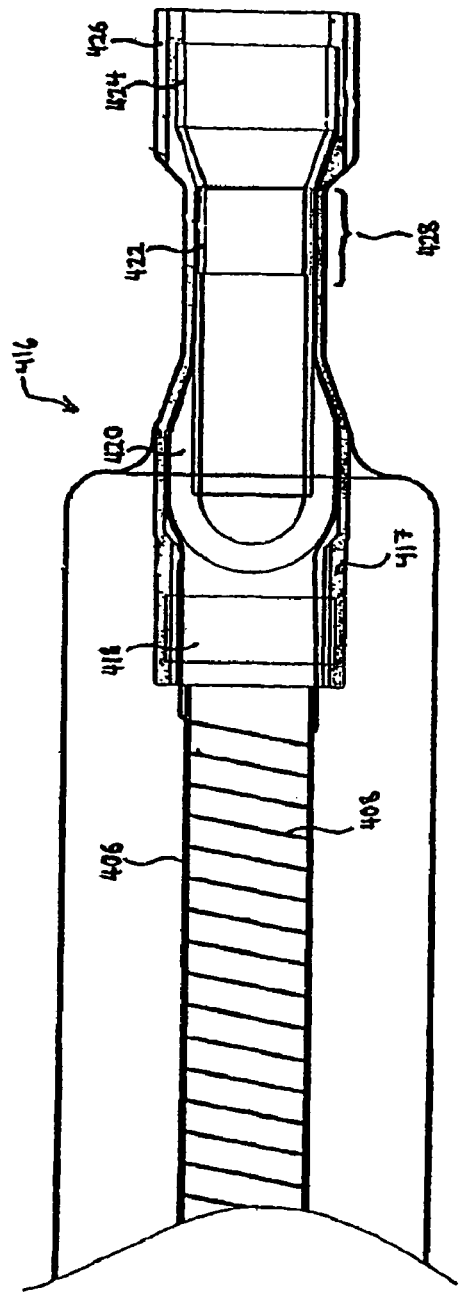

Temperature vs. Time for Polymerization

CURABLE MEDIA FOR IMPLANTABLE MEDICAL DEVICE

This is a divisional of U.S. patent application Ser. No. 10/327,706, filed Dec. 20, 2002 now U.S. Pat. No. 6,875,212, which is a continuation-in-part of U.S. patent application Ser. No. 10/161,554, filed on May 31, 2002 now U.S. Pat. No. 6,964,667, which is a continuation-in-part of U.S. patent application Ser. No. 09/976,459, filed on Oct. 10, 2001 now U.S. Pat. No. 6,749,614, which is a continuation-in-part of U.S. patent application Ser. No. 09/943,636, filed on Aug. 29, 2001 now U.S. Pat. No. 6,899,713, which is a continuation-in-part of U.S. patent application Ser. No. 09/747,066, filed on Dec. 21, 2000 now U.S. Pat. No. 6,821,277, which claims priority to U.S. Provisional Patent Application 60/213,385, filed Jun. 23, 2000, entitled "Percutaneous Interbody Fusion Device," the contents of each of which are incorporated in their entirety into this disclosure by reference

BACKGROUND OF THE INVENTION

1. Field of the Invention

The present invention relates to medical devices and, more particularly, to systems for forming orthopedic fixation or stabilization implants in place within the body, such as by infusing a formable media into a cavity. In one application, the present invention relates to minimally invasive procedures and devices for forming a spinal stabilization rod in situ.

2. Description of the Related Art

The human vertebrae and associated connective elements are subject to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to these diseases, conditions, injuries and manipulations often result from the displacement of all or part of a vertebra from the remainder of the vertebral column. A variety of methods have been developed to restore the displaced vertebrae or portions of displaced vertebrae to their normal position and to fix them within the vertebral column. For example, open reduction with screw fixation is one currently used method. The surgical procedure of attaching two or more parts of a bone with pins, screws, rods and plates requires an incision into the tissue surrounding the bone and the drilling of one or more holes through the bone parts to be joined. Due to the significant variation in bone size, configuration, and load requirements, a wide variety of bone fixation devices have been developed in the prior art. In general, the current standard of care relies upon a variety of metal wires, screws, rods, plates and clamps to stabilize the bone fragments during the healing or fusing process. These methods, however, are associated with a variety of disadvantages, such as morbidity, high costs, lengthy in-patient hospital stays and the pain associated with open procedures.

Therefore, devices and methods are needed for repositioning and fixing displaced vertebrae or portions of displaced vertebrae which cause less pain and potential complications. Preferably, the devices are implantable through a minimally invasive procedure.

SUMMARY OF THE INVENTION

In accordance with one embodiment, there is provided a formed in place orthopedic device. The device comprises an outer wall, defining a cavity therein and a hardenable media within the cavity to form the orthopedic device, said hardenable media comprising a resin and hardener mixture that is substantially cured at a temperature below about 45° C. in about 90 minutes or less, wherein the hardenable media is hardened while the device is positioned within the body of a patient to create the formed in place orthopedic device.

In accordance with another embodiment, there is provided a bone fixation device. The device comprises a delivery catheter comprising an inflatable member, a hardenable media contained within the inflatable member, and at least two anchors having portals, wherein the inflatable member extends through the portals of the anchors. The hardenable media comprises an epoxy that cures to a hardened form having a static compression bending value (ASTM F1717) of at least 90 lbs in about 90 minutes or less.

In accordance with another embodiment, there is provided an orthopedic fixation device. The device comprises an elongate, flexible tubular body having a distal end and a proximal end, said body forming a central lumen, a manifold at the proximal end of the tubular body comprising at least one port, an inflatable member having a proximal end, a distal end, and an interior, removably attached to the distal end of the tubular body a hardenable media for inflating said inflatable member, said hardenable media comprising about 45-52% by weight aromatic diepoxide resin, about 19-23% by weight aliphatic diepoxide resin, about 20-29% by weight dialkylamines and about 4-9% cycloalkylamines; and a valve, provided at the proximal end of the inflatable member.

In accordance with another embodiment, there is provided a method of forming an orthopedic device at a treatment site within the body of a patient, comprising the steps of positioning an outer wall at the treatment site within the patient, the outer wall defining a chamber therein, and introducing a hardenable media into the chamber, wherein the hardenable media cures from a liquid form to a hardened form having a static compression bending value of at least 90 lbs (ASTM F1717) in about 90 minutes or less.

In accordance with another embodiment, there is provided a method of stabilizing an orthopedic fracture, comprising inserting at least two anchors having portals into a bone, delivering an orthopedic device comprising an inflatable balloon to the bone, and inflating said balloon with a hardenable media comprising about 45-52% by weight aromatic diepoxide resin, about 19-23% by weight aliphatic diepoxide resin, about 20-29% by weight dialkylamines and about 4-9% cycloalkylamines, wherein said orthopedic device extends through said portals, such that said inflating fixes said anchors in relation to one another.

In accordance with another embodiment, there is provided a method of stabilizing an orthopedic fracture, comprising inserting at least two anchors having portals into a bone, delivering an orthopedic device comprising an inflatable balloon through the portals, and inflating said balloon with a liquid curable material, wherein the inflating step fixes said anchors in relation to one another and the curable material is substantially cured at a temperature below about 45° C. in about 90 minutes or less. In another embodiment, there is provided a formed in place medical device, comprising an outer wall, defining a cavity therein and a hardenable media within the cavity to form the medical device, said hardenable media comprising a resin and hardener mixture that cures at a temperature below about 45° C. wherein said cured media has a static compression bending value (ASTM F1717) of at least 150 lbs wherein the hardenable media is hardened while the device is positioned within the body of a patient to create the formed in place medical device.

In preferred embodiments, the hardenable or curable material comprises about 45-52% by weight aromatic diepoxide resin, about 19-23% by weight aliphatic diepoxide resin, about 20-29% by weight dialkylamines and about 4-9% cycloalkylamines. In an especially preferred embodiment, the aromatic diepoxide resin comprises diglycidyl ether of Bisphenol A or diglycidyl ether of Bisphenol F; the aliphatic diepoxide resin comprises one or more alkane diols of glycidyl ether; the cycloalkylamines are N-aminoalkylpiperazines; and the dialkylamines are according to the formula $H_2N-R-NH_2$, wherein R is a branched or unbranched $C_2$-$C_{10}$ alkyl group. The hardenable media, when substantially cured, preferably has a static compression bending value (ASTM F1717) of at least about 60 lbs, and at least about 100 lbs when fully cured. The media is preferably substantially cured in about 90 minutes or less, and the curing takes place at a temperature of about 45° C. or less, more preferably about 43° C. or less.

Further features and advantages of the present invention will become apparent to those of skill in the art in view of the detailed description of preferred embodiments which follows, when considered together with the attached claims and drawings.

BRIEF DESCRIPTION OF THE DRAWINGS

FIG. 1 is a side elevational view of a delivery catheter having an inflatable fixation device thereon.

FIG. 2 is a cross-sectional view taken along the line 2-2 of the delivery catheter of FIG. 1.

FIG. 3 is a side elevational cross section of a proximal portion of the delivery catheter of FIG. 1.

FIG. 4C schematically illustrates a cross-section through a composite formable rod in accordance with one aspect of the present invention.

FIG. 5 is a side elevational view of the inflatable fixation device of FIG. 1.

FIG. 6 is a cross-sectional view through the inflatable fixation device of FIG. 5, in the expanded position.

FIG. 7A is a schematic cross-sectional view of a valve of the inflatable fixation device of FIG. 6.

FIG. 7B is a schematic cross-sectional view of an alternate valve.

FIG. 7C is an end view of the valve of FIG. 7B.

FIG. 8 is a perspective view of the manifold of the delivery catheter of FIG. 1.

FIG. 36 is a perspective, schematic view of various components of the cross tie system.

FIG. 37 is a perspective view of a cross tie.

FIG. 40 is a side elevational perspective view of a tubular crossbar sheath.

FIG. 41 is a side elevational schematic view of the crossbar sheath of FIG. 40, mounted on a deployment catheter.

FIG. 42 is a schematic perspective view of the crossbar deployment system of FIG. 41, positioned within two pairs of opposing pedicle screws.

FIG. 43 is a partial cutaway side elevational view of a sheath as in FIG. 40, having an inflatable balloon positioned therein.

FIG. 44 is a schematic side elevational view of the distal end of deployment catheter having a heated implant removably positioned thereon.

FIG. 48A is a side elevational view of an alternate implant in accordance with the present invention, having a resistance heating coil positioned therein.

FIG. 48B is an enlarged fragmentary view of the proximal end of the implant illustrated in FIG. 48A.

DETAILED DESCRIPTION OF THE PREFERRED EMBODIMENT

Figure 4A:
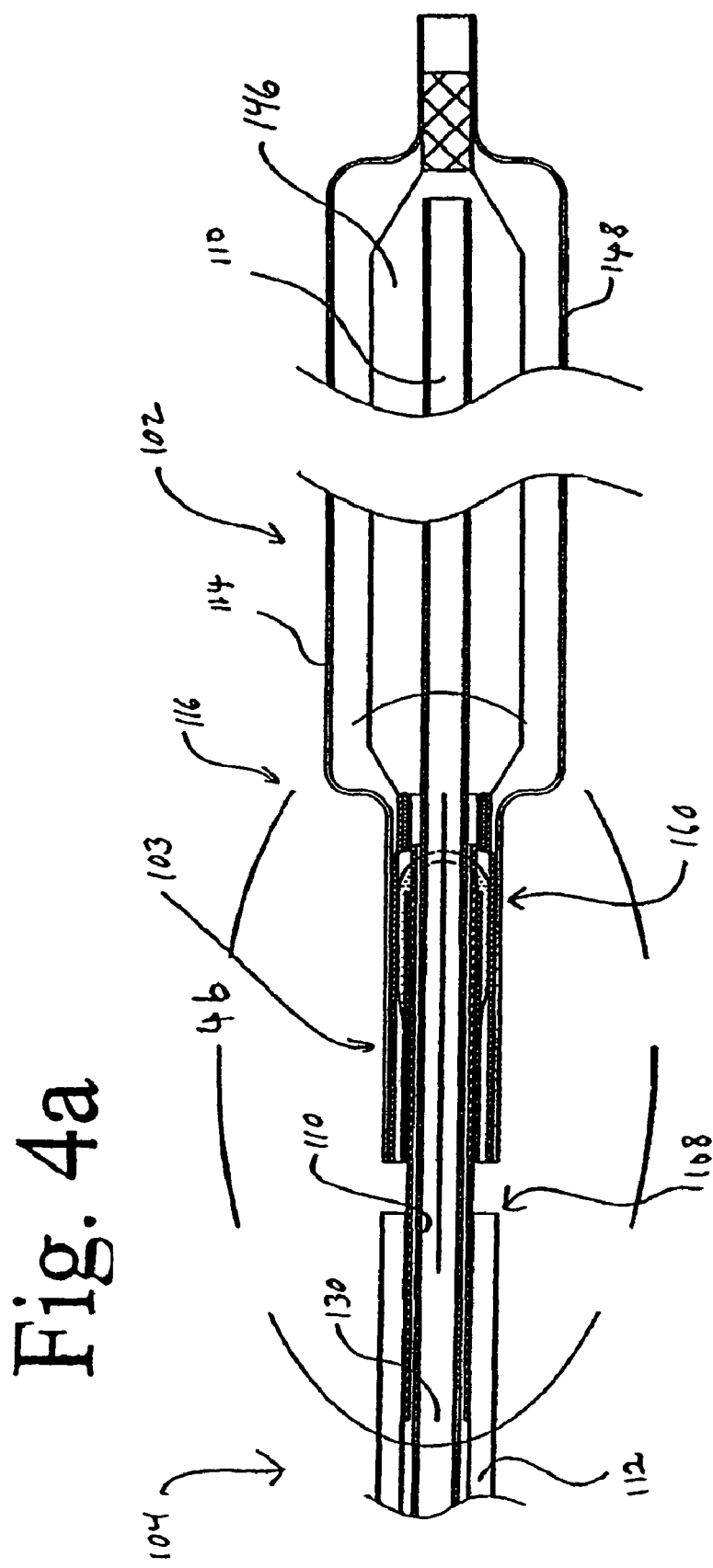
FIG. 4A is a side elevational cross section of a distal portion of the delivery catheter of FIG. 1.

Although the application of the present invention will be disclosed primarily in connection with a spinal fixation procedure, the methods and devices disclosed herein are intended for use in any of a wide variety of medical applications where formation of an attachment, bulking, support, fixation or other element in situ may be desirable.

One advantage of the in situ prosthesis formation in accordance with the present invention is the ability to obtain access to a treatment site through a minimally invasive access pathway, while enabling the formation of a relatively larger implant at the treatment site. This allows procedure morbidity to be minimized, since open surgical cutdowns or other invasive access procedures may be avoided. In addition, the in situ formation in accordance with the present invention allows the formation of an implant having any of a wide variety of customized or predetermined shapes, due to the ability of the infusible hardenable media to assume the shape of the cavity or flexible container into which it is infused.

The methods and devices of the present invention additionally enable access to a treatment site within the body along a curved and even tortuous pathway, through which a preformed prosthesis would not fit or would not be navigable. The detachable inflatable prosthesis of the present invention, removably coupled to the distal end of an elongate flexible tubular catheter body, can be dimensioned for percutaneous, surgical or transluminal advancement and deployment of an inflatable or otherwise curable in place prosthesis in any of a wide variety of orthopedic applications, such as the spine as disclosed in greater detail below, as well as long bones, short bones, and associated ligaments and tendons. In addition, the deployment catheter and prosthesis can be dimensioned for transluminal navigation throughout the cardiovascular system, the gastrointestinal tract, the biliary tract, the genitourinary tract, or the respiratory tract (e.g. the tracheobronchial tree). The device may thus be advanced through artificial access pathways as well as naturally occurring lumens and hollow organs. Additional applications of the in situ device formation technology of the present invention will become apparent to those of skill in the art in view of the disclosure herein.

In connection with spinal fixation applications, the present invention involves inserting one or two or more bone anchors having a connector such as a portal into at least a first and a second adjacent or nonadjacent vertebra. An implantable, inflatable orthopedic device is inserted through the portals and inflated to lock to the bone anchors and stabilize the bone components. A deployment system, comprising a delivery catheter removably carrying the implantable device, is provided, such that the procedure may be conducted in a percutaneous or minimally invasive manner to minimize procedure trauma to the patient.

The deployment system shown in FIG. 1 comprises a delivery catheter 100 which deploys the implantable inflatable orthopedic device 102. Delivery catheter 100 preferably includes an elongate, flexible tubular body 104, having a proximal end 106 and a distal end 108. For certain applications, however, in which direct linear access is intended, the tubular body 104 may be substantially rigid. The tubular body 104 includes one or more passages or lumens extending axially through the body, depending upon the desired functionality of the device.

The overall length and cross sectional dimensions of the delivery catheter 100 may be varied, depending upon the intended clinical application. In a device intended for percutaneous or minimally invasive fusion of lumbar and/or sacral vertebrae, for example, the tubular body 104 will generally have a length within the range of from about 15 cm to about 50 cm, and a diameter within the range of from about 2 mm to about 6 mm.

Percutaneous insertion of the delivery catheter 100 may be facilitated by the provision of a removable elongate stiffening wire 122, extending through a lumen such as inflation lumen 130 (see FIG. 2) from the proximal end 106 of tubular body 104, to the distal end 108 of tubular body 104. Optionally, the stiffening wire 122 extends into, and even all the way to the distal end 118 of the orthopedic device 102, to provide support and column strength to the device 102 which may be desirable during tissue penetration. The distal end of the stiffening wire 122 may be connected to a coil approximately 8 cm in length to allow for a degree of flexibility.

FIG. 2 shows a cross-sectional view through the elongate body 104, showing (not to scale) an inner sleeve 110 and an outer sleeve 112. The inner sleeve 110 defines a first, inflation lumen 130, while a second, venting lumen 132 is defined by the annular space between the inner sleeve 110 and outer sleeve 112. The inflation lumen 130 is adapted to receive the elongate stiffening wire 122 in a sliding fashion through a proximal opening 127 on inner sleeve 110, which in turn extends axially into the outer sleeve 112 by way of port 126 in catheter manifold 124. Although the illustrated embodiment has a dual lumen, concentric or coaxial configuration, three or more lumen may alternatively be provided, depending upon the desired capabilities of the catheter. A single lumen catheter may also be provided, to accommodate a removable stiffening wire, if utilized, and to facilitate inflation of the implantable device. Alternatively, a two or more lumen catheter shaft may be fabricated, extruded or otherwise formed with the lumen in a side-by-side configuration.

The deployment device 100 further comprises a manifold 124, located at the proximal end 106 of the elongate tubular body 104. The catheter manifold 124 provides a maneuvering handle for the health care professional, and supports an inflation port 126 and a vent port 128. Either or both the inflation port 126 or the vent port 128 may be provided with a coupling, such as a luer-lock fitting for connection to associated devices as is known in the art. For example, a luer or other connector on the inflation port 126 facilitates connection to a source of pressurized inflation media in a conventional manner. The vent port 128 may be connected to a syringe or other device to draw a vacuum, to evacuate air from the balloon prior to infusion of the hardenable media.

The manifold 124 may also include an injection port for allowing injection of radiopaque contrast fluid to enable visualization of the delivery device on a fluoroscope. The proximal manifold 124 may be machined or injection molded of any of a variety of known suitable materials such as PTFE, ABS, nylon, polyethylene, polycarbonate, or others known in the art. A precision gasket may also be provided, which seals securely around the inner sleeve 110, prohibiting fluid loss.

Catheter manufacturing techniques are generally known in the art, including extrusion and coextrusion, coating, adhesives, and molding. The catheter of the present invention is preferably made in a conventional manner. The elongate shaft of the catheter may be extruded, using polymers such as Nylon, PEBAX, PEEK, PTFE, PE or others known in the catheter arts, the stiffness of which may be selected as appropriate. Material selection varies based on the desired characteristics. The joints are preferably bonded. Biocompatible adhesives or heat bonding may be used to bond the joints. The balloon and stent are also made in a conventional manner or in any suitable manner.

The deployment system 100 further comprises an implantable inflatable orthopedic device 102, which may function, in a spinal fusion application, as an inflatable or formed in place fixation plate or rod. Implantable device 102 is removably carried by the distal end of the tubular body 104, such that inflation lumen 130 is in communication with the interior cavity 146 of the inflatable device 102. The inflation media may thus be infused through inflation port 126 (or opening 127) located at manifold 124 to fill the cavity 146.

The implantable device 102, which may be a balloon 114, includes a proximal end 116, a distal end 118, and a flexible wall 148. The balloon 114 may be formed from any of a variety of polymeric materials which are known in the balloon angioplasty arts. These include, for example, complaint materials such as polyethylene, polyethylene blends or nylon, and substantially noncompliant materials such as polyethylene terephthalate. Any of a wide variety of other biocompatible polymers may be utilized, as will be apparent to those of skill in the art in view of the disclosure herein.

The balloon 114 may comprise a single or multiple layers, depending upon the desired physical properties. In one embodiment, the balloon comprises two layers, having a reinforcing structure such as a stent or a plurality of axially extending support strips sandwiched therebetween. In an alternate embodiment, the balloon 114 comprises a first, inner layer which restrains the hardenable media. A second, outer layer is coaxially disposed about the first layer, and is provided with a plurality of apertures or a microporous structure. An infusion lumen is provided in the elongate tubular body, for providing communication between a proximal infusion port and the space in between the inner and outer balloon layers. In this manner, fluids, which may contain any of a variety of medications, can be infused into the tissue surrounding the treatment site. Suitable structures and manufacturing considerations are disclosed in U.S. Pat. No. 5,295,962 to Crocker et al., the disclosure of which is incorporated in its entirety herein by reference.

Although a cylindrical configuration for balloon 114 is illustrated herein, any of a variety of alternative cross sectional configurations may be utilized. The overall length, diameter and wall thickness of the implantable inflatable orthopedic device 102 may be varied, depending on the particular treatment and access site. In one embodiment, device 102 has an inflated length between about 2 and 12 cm, and often between about 5 cm and about 8 cm for adjacent vertebrae fixation. The device 102 has an inflated diameter of generally between about 0.5 and 2 cm.

The length of the balloon 114 is based upon the anticipated distance between the first and second anchors, or, in an embodiment having more than two anchors, between the anchors having the greatest axial separation. For example, in a fusion application in which two adjacent lumbar vertebrae (e.g. L4-L5) are to be fused in an adult, the first and second anchors will generally be spaced apart by a distance within the range of from about 5 cm to about 8 cm. Preferably, the axial length of the balloon 114 is sufficiently longer than the inter anchor spacing to permit a portion of the balloon to expand on the "far" side of the anchor aperture as is illustrated, for example, in FIG. 9. Thus, balloon lengths for the above identified inter anchor distances will generally exceed the sum of the inter anchor distance and the anchor diameters by at least about 0.5 cm. Preferably, the balloon extends at least about 1 cm beyond the portals.

For use in an application where a first vertebrae is attached to a second vertebrae, and the second vertebrae is separated from the first vertebrae by at least a third vertebrae, for example in the lumbar spine, the inter anchor distance will generally be within the range of from about 10 cm to about 20 cm. As will be appreciated by those of skill in the art, in a three or more vertebrae fixation, the intermediate vertebra or vertebrae will normally but need not necessarily be connected to the inflatable balloon 114. Thus, in one application, the balloon 114 connects a first attachment point at a first bone and a second attachment point at a second bone, with one or more intermediate bones unconnected to the balloon 114. In another application, at least a third anchor is provided in between the first and second anchors, and the balloon 114 is threaded through an aperture on each of the first, second and third anchors. The desirability of attaching or leaving unattached intervening vertebrae or other bones or structures between two attachment points is a matter of clinical judgement, in view of the particular circumstances of the patient.

The primary function of the balloon 114 is to influence or control the shape of the hardenable media, following injection therein. The implantable balloon 114 is not normally required to restrain pressure over an extended period of time. Thus, a greater design flexibility may be permitted, compared to conventional angioplasty or other dilatation balloons. For example, the balloon 114 may be porous, either for drug delivery as has been discussed, or to permit osteoincorporation and/or soft tissue ingrowth.

Certain hardenable media which may be utilized in connection with the present invention, such as PMMA, have a significantly greater viscosity in the precured form, compared to conventional angioplasty balloon inflation media. In addition, since the balloon 114 is not intended to contain significant pressure, conventional high strength materials such as for high pressure angioplasty may not be necessary. This allows the balloon 114 to be constructed in any of a variety of ways, including techniques utilized for balloon angioplasty applications. In addition, the balloon 114 (or balloon-like structure) may be made out of any of a wide variety of woven or nonwoven fibers, fabrics, metal mesh such as woven or braided wires, and carbon. Biocompatible fabrics or sheet material such as ePTFE and Dacron® may also be used.

The hardenable media is preferably a rapid setting, low viscosity, liquid polymer or polymer precursor, such as polymethyl methacrylate. However, any of a variety of other materials which provide the required stiffening or setting characteristics may be used, including any of a variety of epoxies, polyurethane or blends of polyurethane-silicone.

In the context of a rod shaped inflatable container, for use in spinal fixation procedures, the physical requirements of the hardenable media will depend upon the length and diameter of the rod as well as the physical requirements imposed by the implantation site. For certain embodiments, polymethyl methacrylate, epoxy, polyurethane or other particular material may or may not exhibit sufficient physical properties. Physical properties of a hardenable material can be modified through the addition of any of a variety of additives, such as carbon fibers, Kevlar or Titanium Rods, woven or laser etched metallic tubular stents, or other strength enhancers as will be understood in the art. The selection of a particular hardenable media, as well as the desirability of adding strength, flexibility, or other physical property enhancers, can be optimized for any particular implantation system through routine experimentation by those of skill in the art in view of the disclosure herein.

Certain composite materials, such as carbon fibers embedded in a bonding agent such as a two part epoxy, or two part polyurethane have been found particularly useful in forming the implant of the present invention. For example, graphite (carbon fibers) having a diameter within the range of from about 0.003 to about 0.007 inches are provided in bundles (tows) composed of from about 3,000 to about 12,000 fibers. One typical fiber useful for this purpose is manufactured by Hexcel Carbon Fibers, Salt Lake City, Utah, Part No. HS/CP-5000/IM7-GP 12K. Preferably, the Tow tensile strength is in the range of from about 5,000 to about 7,000 Mpa. Tow tensile modulus is within the range of from about 250 to about 350 Gpa.

In certain embodiments, the fixation rods are formed without the need of reinforcing fibers or rods. In such embodiments, the hardenable material itself exhibits physical properties sufficient for use in the implants.

In general, the composite rods in accordance with the present invention will exhibit a static compression bending values (per ASTM F1717) within the range of from about 100 to about 200 lbs., and, preferably greater than about 150 lbs. The composite rods will exhibit a static torsion (per ASTM F1717) within the range of from about 300 to about 500 inch pounds, and, generally in excess of about 400 inch pounds. The rods will preferably reach at least about 5 million cycles, at 5 Hz. Each of these parameters may be measured in accordance with the protocols described in the American Society for Testing and Materials (ASTM) designation F 1717-96, a copy of which is attached hereto as Appendix A, and which is incorporated in its entirety herein by reference.

Within the range of from about 30 to about 60 bundles of the carbon fiber described above is packed in a deflated balloon, optionally along with a Ni—Ti stent having an 8 mm diameter and 8 cm length. Although any of a variety of stents may be utilized, one useful structure is similar to the Smart Stent (Cordis), and it helps keep the structure intact and also adds structural strength to the implanted structure.

A one or a two part epoxy having a viscosity in the range of from about 100 to about 1000 cps is then injected into the balloon under pressure such as by using a pump and pressure within the range of from about 4 ATM to about 10 ATM or more depending upon viscosity, balloon strength and other design considerations. The pump is run for a sufficient duration and under a sufficient pressure to ensure that the epoxy wets all of the fibers. This may range from about 10 minutes or more to about an hour, and, in one application where the pump was run at about 5 ATM pressure, requires at least about ½ hour. Specific method parameters may be optimized depending upon the viscosity of the epoxy, infusion pressure, infusion flow rate, density of the packed carbon fibers, and other variables as will be apparent to those of skill in the art in view of the disclosure herein.

In an alternate embodiment, carbon fibers having within the range of from about 15 to about 45 degrees of braids are utilized. The braid may be in the form of a plain weave, and may be obtained, for example, from Composite Structures Technology (Tehachapi, Calif.). A 0.5 inch diameter of 45 degrees braided carbon fiber sleeve is positioned within the center of the balloon. This braided sleeve conforms dimensionally to the inside diameter of the balloon. A 0.3 inch diameter braided carbon sleeve (again 45°×45° plain weave) may also be positioned concentrically within the balloon, within the outer braided carbon fiber sleeve. Unidirectional fibers are thereafter introduced inside of the ID of the inner braided carbon sleeve. Unidirectional fibers are also introduced into the annular gap between the two braided sleeves. The volume of the fiber per volume of balloon is generally within the range of from about 40% to about 55%. After placement of the foregoing structure within the portals of the screws, the epoxy mix having a viscosity within the range of from about 100 to about 1000 cps is injected under 10 atmospheres pressure into the balloon.

Although the foregoing composite structure was described using a carbon fiber example, any of a variety of fibers may be positioned within the balloon to enhance the physical properties of the finished product. For example, Kevlar fibers, PEEK, and any of a variety of alternatives may be used. In general, the fibers will preferably provide a very high tensile strength and high modulus, having a low diameter to enhance deliverability of the device.

The use of braided sleeves will produce higher structural resistance to sheer stress as a result of torsional loads, plus the ability to distribute unidirectional fibers in a homogenous manner within the balloon at all times. This appears to improve the performance of the implant.

One construction of a composite formable rod in accordance with the present invention is illustrated in FIG. 4C. An outer balloon or other containment structure 114 is provided, as has been discussed. A reinforcing element 120 such as a stent is concentrically positioned within the balloon. An outer support tube 121 is positioned within the stent in the illustrated embodiment, however, the outer support tube 121 can alternatively be positioned concentrically outside of the stent 120. The outer support tube 121, in one embodiment, is a 0.5 inch diameter braided carbon fiber tube, having cross strands oriented at 45° angles with respect to each other to improve torsion resistance as has been discussed.

An inner support tube 123 is spaced radially inwardly from the outer support tube 121. Inner support tube 123, in one embodiment, comprises a 0.3" diameter braided carbon fiber sleeve having characteristics described above. A first plurality of unidirectional fibers 125 is axially oriented within the annular space between the outer support tube 121 and inner support tube 123. A second plurality of unidirectional carbon fibers 127 is positioned within the inner support tube 123.

Any of a variety of alternate constructions can be readily utilized, in accordance with the teachings herein. For example, three or more tubular support tubes may be utilized. The layering sequence of the various components may be changed, and other features added or deleted depending upon the desired performance of the finished device. In addition, although the balloon 114 in one embodiment comprises a nylon single layer balloon, other materials may be utilized. In addition, multiple layer balloons may be utilized, with or without support structures such as stents, wires, or woven tubular support structures sandwiched therebetween.

In alternate embodiments, the formable rods do not include one or more of the reinforcing structures illustrated in FIG. 4C. In one such alternate embodiment, the first plurality of unidirectional fibers 125 and the second plurality of unidirectional fibers 127 are not present. In another such alternate embodiment, the inner support tube 123, outer support tube 121, and/or stent 120 are not present in the rod, which may or may not contain fibers 125, 127.

Other embodiments comprise a containment structure such as an outer balloon or mesh, and have none of the aforementioned reinforcing structures shown in FIG. 4C. In such other embodiments, the hardenable media alone suffices to form a rod having the needed strength and other physical characteristics. Embodiments that have few or no reinforcing or support structures are formed in substantially the same way as those discussed above, in that the hardenable media is injected into the containment structure in fluid form and then allowed to harden.

Marker bands made of materials such as gold, platinum or tantalum may also be positioned on the balloon, to facilitate fluoroscopic visualization. Alternatively, a radio opaque material, such as tantalum powder, may be sprinkled among the carbon fibers prior to infusion of the epoxy or other hardenable media, to allow visualization during placement.

The epoxy or the polyurethane material preferably has a relatively fast cure rate at 37° C. A low viscosity (no greater than from about 100 to about 1000 cps) facilitates rapid transluminal introduction through the delivery catheter and wetting of the relatively small interstitial spaces between adjacent carbon fibers. In addition, the polymer is preferably radiopaque. The polymerization is preferably minimally exothermic, to minimize or prevent thermal damage to the surrounding tissue. One epoxy which may be useful in the present invention is Epotek 301 available from Epoxy Technology, Inc. (Billerica, Mass.). This epoxy reaches 50 to 60% of its strength within about three to four hours following deployment, at 37° C. Using a bonding agent having these approximate characteristics, the patient can be restrained from rolling for an initial cure period of approximately three or four hours to achieve a partial cure (e.g., at least about 50% and preferably 60% or more), and be maintained in bed for a secondary cure period such as approximately the next eight to twelve hours or more to accommodate a full cure. Other formulations of two part epoxies or polyurethanes with faster cure times (preferably no more than about one hour full cure) can be formulated by changing the ratios of components and formulations for the catalysts. Cure time can also be accelerated through the use of accelerators, such as catalysts or the application of heat as is discussed in detail below.

In accordance with certain embodiments, preferred hardenable media have one or more of the following characteristics: (1) they cure completely at a temperature that approximates that of an animal body (about 35-42° C.); (2) they exhibit mildly exothermic curing behavior, meaning that the media only self-heats due to the curing reaction to a temperature below about 45° C., preferably below about 42° C. so as to reduce the risk of heat damage to nearby living tissues during curing; (3) they exhibit little or no shrinkage of during curing so as to maintain a tight fit following curing; (4) they have a pre-cure viscosity of preferably about 100-1000 cps, more preferably about 100-400 cps; (5) they have a useful life ("potlife") (i.e. have a viscosity low enough to allow for injection) of no more than about 30 minutes after mixing/initiation/activation, preferably no more than about 15 minutes; (6) they are substantially cured (i.e. they are capable of forming a rigid rod of material) preferably within about 20-100 minutes or less, including within about 30, 40, 50, 60, 70, 80, and 90 minutes or less after initiation, such as by mixing; (7) they will form a substantially cured rod having a static compression bending value (per ASTM F1717) of at least about 60 lbs. (force), including about 70, 80, 90 and 100 lbs.; (8) they will form a fully cured rod (unreinforced) having static compression bending values (per ASTM F1717) within the range of from about 100 to about 200 lbs (force), preferably greater than about 150 lbs, including about 110, 120, 130, 140, 160, 170, 180, and 190 lbs., preferably within about 10-12 hours of initiation; (9) they will form a fully cured rod (unreinforced) having a static torsion (per ASTM F1717) within the range of from about 300 to about 500 inch pounds, preferably in excess of about 400 inch pounds; and (10) they will form a biocompatible solid. Especially preferred embodiments of hardenable media exhibit most or all of the foregoing characteristics.

One preferred family of hardenable media are two part epoxies having a very short cure time. The first part preferably comprises one or more compounds bearing epoxide groups, preferably two or more epoxide groups, and has a low viscosity. Preferred compounds include diepoxide resins having molecular weights between about 100 and 400, including, but not limited to, aromatic diepoxide compounds such as diglycidyl ether of Bisphenol A, and diglycidyl ether of Bisphenol F. Other preferred compounds include aliphatic epoxide resins, including cycloaliphatic resins. One preferred class of aliphatic epoxide resins are the diepoxide resins that are alkane diols of glycidyl ether, wherein the alkane portion is pentane, butane, propane, and the like. Such compounds generally have low viscosity (less than about 100 cp) and are sometimes called "reactive diluents" in that, when they blended with other epoxide materials, they serve to reduce the viscosity of the mixture as well as react to form cross-links within the matrix of the cured epoxy. The first part may also comprise monofunctional epoxide modifiers. In a preferred embodiment, the first part comprises a mixture of aromatic diepoxide compounds and aliphatic diepoxide compounds.

The second part preferably comprises one or more curing agents or hardeners, including, but not limited to, aliphatic and cycloaliphatic hardeners, mercaptan curing agents, and amine curing agents such as diamines, triamines, tetramines, methylamines, ethylamines, propylamines, aminopiperazines, and other specialty amines. Preferred curing agents or hardeners allow for cure of the media at ambient or near ambient temperatures, preferably below about 45° C. Preferred compounds include 1,3 diaminopropane, diethylenetriamine, triethylenetetramine, N-aminoethylpiperazine (including N-aminoethylpiperazine nonyl/phenol from Air Products and Chemicals, Allentown, Pa.) and compounds according to the general formula:

$$H_2N\text{-}(R\text{-}NH)_xR\text{-}NH_2$$

wherein each R is independently selected from branched or unbranched chains of about 2-10, preferably 2-5, carbon atoms, and x is 0, 1, or 2. In preferred embodiments, R is alkyl, preferably straight chained, and all R groups are the same. In some embodiments, the second part comprises a mixture of a cycloalkylamines, such as piperazine-based amines, and alkylamines.

In accordance with a preferred embodiment, formulations comprise about 60-80%, more preferably about 65-75% by weight of diepoxide compounds (first part) and about 20-40%, more preferably about 25-35% by weight of amine curing agent (second part). In one embodiment, the first part comprises about 45-52% by weight aromatic diepoxide compounds and about 19-23% by weight aliphatic diepoxide compounds, and the second part comprises about 20-29% alkyldiamines and about 4-9% by weight N-aminoalkylpiperazines. Five examples of formulations according to preferred embodiments are presented in Table 1 below.

TABLE 1

| Formulation | Component | Quantity (weight %) |
|---|---|---|
| VL14M | | |
| Part 1 | Diglycidyl Ether of Bisphenol A | 46.75% |
| | Butane Diol of Glycidyl Ether | 20.00% |
| Part 2 | n-aminoethylpiperazine nonyl/phenol | 28.34% |
| | 1,3 diaminopropane | 4.91% |
| VL18 | | |
| Part 1 | Diglycidyl Ether of Bisphenol A | 49.12% |
| | Butane Diol of Glycidyl Ether | 21.05% |
| Part 2 | n-aminoethylpiperazine nonyl/phenol | 21.05% |
| | 1,3 diaminopropane | 8.78% |
| VL18-3 | | |
| Part 1 | Diglycidyl Ether of Bisphenol A | 51.47% |
| | Butane Diol of Glycidyl Ether | 22.06% |
| Part 2 | n-aminoethylpiperazine nonyl/phenol | 22.06% |
| | diethylene triamine | 4.41% |
| VL18-4 | | |
| Part 1 | Diglycidyl Ether of Bisphenol A | 51.09% |
| | Butane Diol of Glycidyl Ether | 21.90% |
| Part 2 | n-aminoethylpiperazine nonyl/phenol | 21.90% |
| | triethylene tetraamine | 5.11% |

TABLE 1-continued

| Formulation | Component | Quantity (weight %) |
|---|---|---|
| VL18-12 | | |
| Part 1 | Diglycidyl Ether of Bisphenol A | 49.82% |
| | Butane Diol of Glycidyl Ether | 21.35% |
| Part 2 | n-aminoethylpiperazine nonyl/phenol | 24.20% |
| | triethylene tetraamine | 4.63% |

For embodiments using other resins and/or hardeners, the amounts used will need to be adjusted to maintain the stoichiometric ratios (epoxy groups to amino groups), as will be appreciated by those skilled in the art.

The first part and/or the second part may further comprise a material to lend radiopacity or fluoropacity to the media so that it is more readily visualized during and after the procedure.

The hardenable material is made by mixing together the first and second parts. The first and second parts may be mixed prior to injection or they may be mixed during injection, such as by use of a static mixer as is known in the art. In preferred embodiments, the mixture is degassed to remove any air bubbles that are formed during mixing. Removal of air bubbles, if present, will serve to reduce the viscosity of the mixture and will also help prevent the formation of voids in the cured rod that result from air bubbles in the hardenable media.

Terms such as "hardenable" or "curable" media are used interchangeably herein, and are intended to include any material which can be transluminally introduced through the catheter body into the cavity 146 while in a first, flowable form, and transitionable into a second, hardened or polymerized form. These terms are intended to cover materials regardless of the mechanism of hardening. As will be understood by those of skill in the art, a variety of hardening or polymerizing mechanisms may exist, depending upon media selection, including hardening or polymerization due to exposure to UV or other wavelength of electromagnetic energy, catalyst initiated polymerization, thermally initiated polymerization, and the like. Mechanisms such as solvent volatilization may also be used, but are disfavored due to the greater likelihood of the formation of voids in the cured rod by evaporating solvent. While the media selection may affect catheter design in manners well understood by those of skill in the art, such as to accommodate outgassing of byproducts, application of heat, catalysts, or other initiating or accelerating influences, these variations do not depart from the concept of the invention of introducing a flowable media into a shape and subsequently curing the media to the shape. Two part media, such as a two part epoxy or polyurethane, or a monomer and an initiator may be introduced into the cavity 146 through separate lumen extending throughout the tubular body. Expandable media may also be provided, such as a material which is implantable in a first, reduced volume, and which is subsequently enlargeable to a second, enlarged volume such as by the application of water or heat, or the removal of a restraint.

Figure 53:
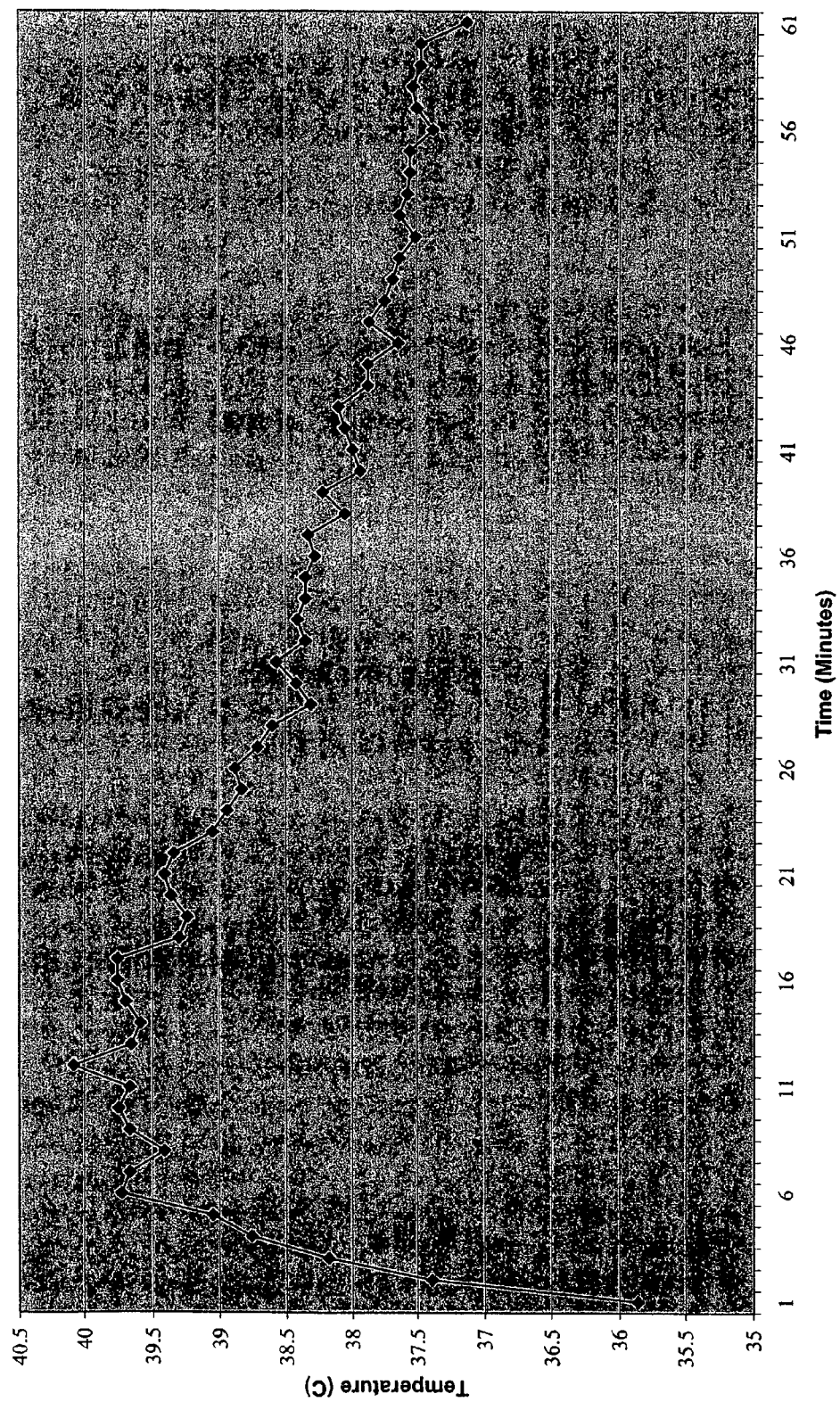
FIG. 53 is a graph showing time versus temperature during polymerization of a hardenable rod formed in situ.

A study was undertaken demonstrating the low exotherm during polymerization or hardening of a rod according to a preferred embodiment. The study involved the use of two pigs. In the first pig, 8 rods were implanted for mechanical strength studies. In the second pig, 5 rods were implanted for conducting thermal studies. All the rods were implanted in the back muscle near the vertebral structure. Epoxy formulation VL-14 mixed with tungsten powder (1-5 micron size) was injected at a pressure of about 8 atm (about 118 Psi) into the balloon to form the rod 2-3 minutes after it was mixed using an Angioplasty pump. Thermocouples were connected to the outside surface of the rods implanted in the second pig and a multichannel recorder connected to a PC monitored the temperature measured at the surface of the rod from the injection (time 0) to 60 minutes following injection at intervals of one minute. The data for one of the recorded channels is presented in FIG. 53. The data obtained for the other channels was substantially similar to that presented in the figure. As can be seen in FIG. 53, the maximum temperature reached was 40.5° C. The mechanical data obtained after curing period of 90 minutes resulted in an average of 93.5 lbf for maximum bending compression strength for the construct as defined by ASTM F-1717.

Various safety features to minimize the risk of rupture or leakage of the hardenable media may be utilized, depending upon design preferences. For example, a two-layer or three-layer or more balloon may be utilized to reduce the risk of rupture. In addition, the material of the single or multiple layers of the balloon may be selected to minimize escape of volatile components from the curable media. In one embodiment, a double balloon is provided having a nylon inside layer and a PET outside layer.

In addition, the inflation pressure of the curable media may be affected by the nature of the balloon. For example, a polyethylene balloon having a wall thickness of about 0.001" may have a burst pressure of about 7 to 8 atmospheres. In that embodiment, an inflation pressure of no more than about 4 to 5 atmospheres may be desired. A slightly higher inflation pressure, such as on the order of from about 5 to about 6 atmospheres, may be utilized with a nylon balloon. Relatively noncompliant materials such as PET have much higher burst pressures (range of 10-20 atmospheres), as is well understood in the balloon angioplasty arts.

In addition, the balloon contains a proximal valve as will be discussed in additional detail below. Multiple valves may be utilized, in series along the flow path, to reduce the risk of failure and escape of hardenable media. As a further safety feature, the deployment catheter may be provided with an outer spill sheath in the form of an elongate flexible tubular body which surrounds the deployment catheter and at least a proximal portion of the balloon. This spill sheath provides an additional removable barrier between the junction of the catheter and the balloon, and the patient. If a spill occurs during the filling process, the spill sheath will retain any escaped hardenable media, and the entire assembly can be proximally retracted from the patient. Following a successful filling of the balloon, the spill sheath and deployment catheter can be proximally retracted from the patient, leaving the inflated formable orthopedic fixation structure in place.

The reinforcing element 120 may be exposed to the interior cavity 146 formed by the flexible wall 148, providing additional structural integrity. See, e.g., FIGS. 1 and 4C. The reinforcing element 120 resists kinking of the balloon as the balloon is advanced around corners such as during advancement through an aperture (e.g., portal or eyelet) on a bone anchor. The reinforcing element 120 may be positioned within the balloon 114. The reinforcing element may alternatively be embedded within the wall of the balloon 114, or carried on the outside of the balloon much like a conventional stent. The reinforcing element 120 may be an expandable tube, a slotted metal tube, reinforcing wires, straight, woven or braided fibers such as carbon fibers, or a stent and may be provided with electrical conductors for completing a circuit through the deployment catheter, to generate heat and/or measure temperature, as is discussed below. Certain preferred embodiments may include a tube or wire. Reinforcement element 120 may comprise thin, reinforcing metallic wires, separate from the balloon wall. The wires increase the tensile strength of balloon 114 when inflated. Wires may be titanium, nitinol, elgiloy, or any other suitable material as known to those of skill in the art.

The reinforcement element 120 may include an expandable tubular stent. A stent of any suitable type or configuration may be provided with the delivery device, such as the Cordis artery stent ("smart stent"). Various kinds and types of stents are available in the market (Sulzer/Medica "Protege" stent and Bard "Memotherm" stent), and many different currently available stents are acceptable for use in the present invention, as well as new stents which may be developed in the future.

Figure 4B:
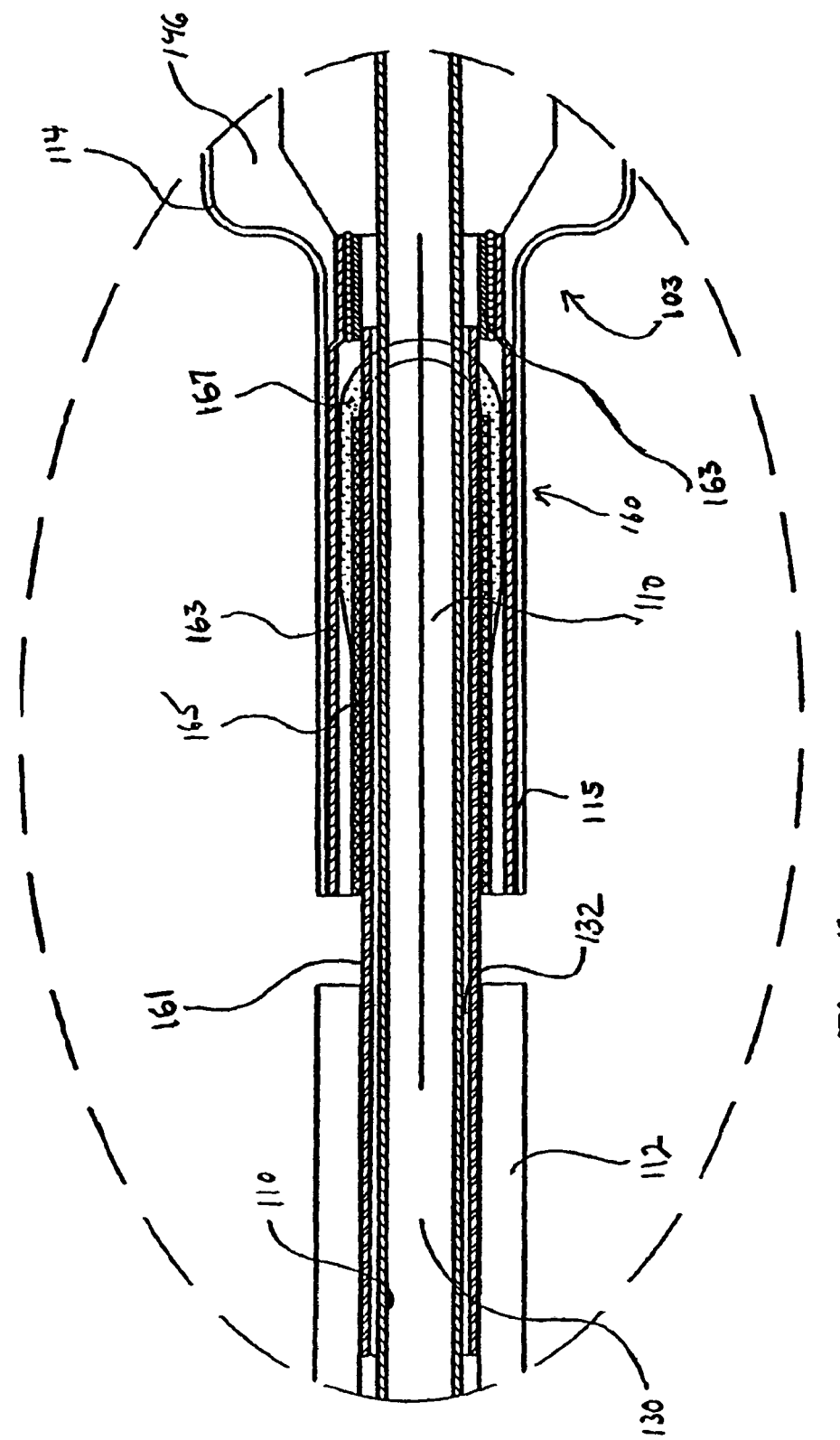
FIG. 4B is a detailed view of the inflatable fixation device of FIG. 4A.

Referring to FIGS. 4A and 4B, the illustrated elongate tubular body 104 comprises an outer sleeve 112 and an inner sleeve 110 movably positioned within the outer sleeve 112. The inflatable device 102 is removably carried by or near the distal end 108 of the outer sleeve 112. Alternatively, the inflatable device 102 may be removably carried by the inner sleeve 110. The inner sleeve 110 may extend into the inflatable device 102, as illustrated.

The balloon 114 may be removably attached to the tubular body 104 by a slip or friction fit on the distal end 108 of the outer sleeve 112 or on the inner sleeve 110. A variety of alternative releasable attachments may be used between the outer sleeve 112 and/or inner sleeve 110 and the proximal end 103 of the balloon 114, such as threaded engagement, bayonet mounts, quick twist engagements like a luer lock connector, and others known in the art. In each of these embodiments, a first retention surface or structure on the outer sleeve 112 and/or inner sleeve 110 releasably engages a complimentary surface or retention structure on the proximal end 103 of the balloon 114 as will be apparent to those of skill in the art.

The balloon 114 comprises a self-sealing valve 160 which prevents the hardenable media from leaking once the delivery catheter 100 is detached from the balloon 114. Valve 160 is provided for closing the pathway between inflation lumen 130 and inner cavity 146. Valve 160 may be located at the proximal end 116 of inflatable device 102. A variety of different valves may be used as will be recognized by those of skill in the art, such as a slit valve, check valve, duck-billed or flap valve. A pierceable, self-sealing septum may also be used. Alternatively, a stopper may be provided which can be placed within the pathway to prevent leakage.

Referring to FIG. 7A, a duck bill valve is schematically illustrated. This valve includes at least a first, and preferably two or more coaptive leaflets 161 and 163, which incline towards each other in the distal direction as will be understood by those of skill in the art. Distal advancement of the inner sleeve 110 and/or pressurized media through the valve 160 forces the coaptive leaflets 161 and 163 apart, to facilitate introduction of the hardenable media. Upon removal of the inner sleeve 110, the coaptive leaflets 161 and 163 return to a closed configuration to inhibit or prevent the escape of hardenable media. A single leaflet 161 may be utilized, in the form of a flapper valve.

An alternate valve is illustrated in FIGS. 7B and 7C, and in an assembled device in FIG. 4B. In this valve, a tubular support structure 165 is provided with a closeable cap 167. The closeable cap 167 may be formed from any of a variety of highly flexible polymeric materials, such as silicone, neoprene, latex, or others known in the art. Cap 167 may be formed such as by dip molding or liquid injection molding, followed by the provision of a slit or potential opening 169.

The valve 160 may be connected to or formed with the inflatable device in any of a variety of manners, as will be appreciated in view of the disclosure herein. In the illustrated embodiment, the balloon 114 is provided with a proximally extending neck 115 which carries the valve 160 therein. The tubular body 165 having the cap 167 thereon is positioned concentrically within the proximal neck 115, as illustrated in FIG. 4B. Alternatively, the valve 160 may be positioned within the balloon 114, i.e., distally of the proximal shoulder of the balloon 114.

Additional details of one detachable connection between the delivery system and the implantable device is illustrated in FIG. 4B. As illustrated therein, a tube 161 extends distally from the outer sleeve 112. Tube 161 may comprise any of a variety of materials, which exhibit sufficient structural integrity for the intended use. In one embodiment, tube 161 is a metal hypotube having an inside diameter of about 0.085" to about 0.086 and a wall thickness of about 0.001" to about 002". The tube 161 in the illustrative embodiment extends for a distance of about 0.50 mm to about 0.75 mm beyond the distal end of the outer sleeve 112.

The tube 161 extends into a sliding fit with a tubular support structure 163 which may be positioned in a proximal neck portion of the balloon. When positioned as illustrated, the tube 161 ensures that the valve 160 is open, so that the inner sleeve 110 may extend axially therethrough into the balloon.

In addition, the inside diameter of the tube 161 is preferably sufficiently larger than the outside diameter of the inner sleeve 110 to provide an annular passageway in communication with the vent lumen 132. This structure ensures that the interior of the balloon remains in communication with the proximal vent port by way of a vent lumen 132 extending throughout the length of the assembly. In the illustrated embodiment, the outside diameter of the inner sleeve 110 is about 0.082" to about 0.084", and the inside diameter of the tube 161 is about 0.085" to about 0.086". Following infusion of the curable media into the balloon, the inner tube 110 and tubular body 161 are both proximally retracted from the balloon, thereby enabling the valve 160 to close as is described elsewhere herein.

When fully inflated, as shown in FIG. 6, the balloon 114 has an inflated profile with a cylindrical working portion 140 having an inflated diameter located between a pair of conical end portions 142, 144.

Figure 9:
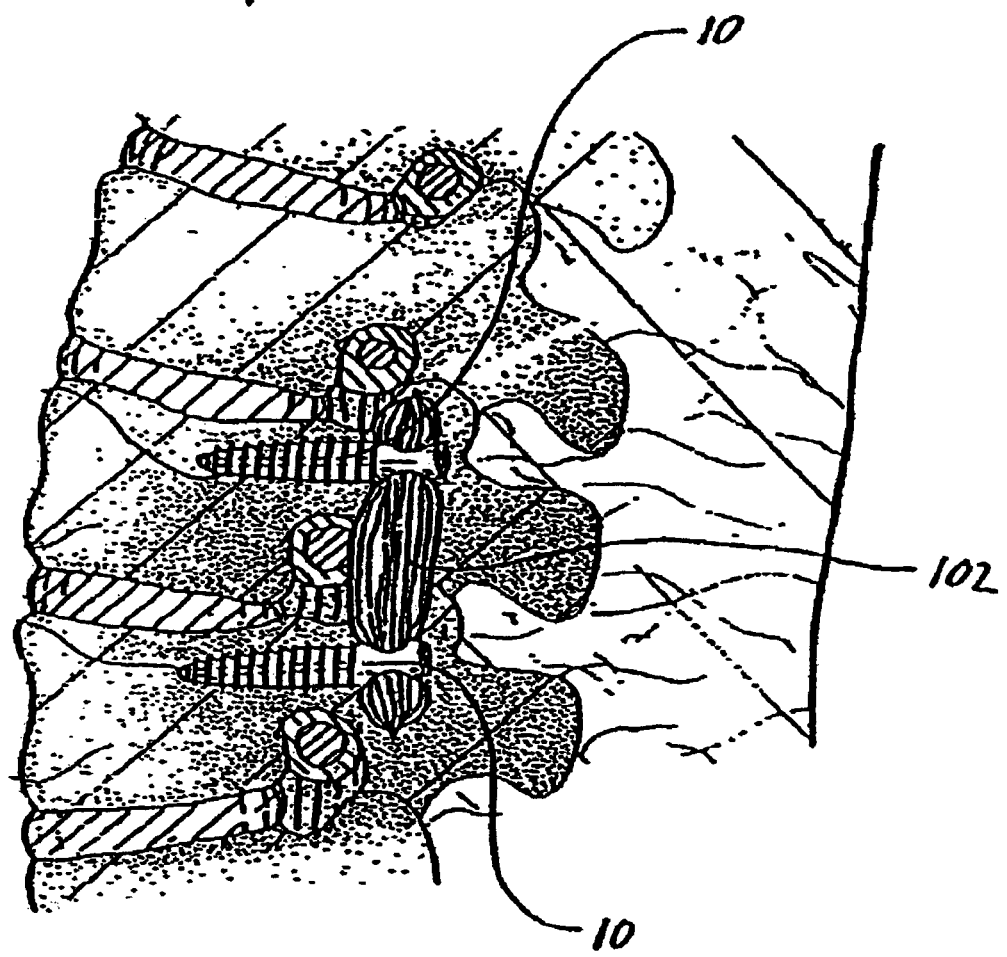
FIG. 9 is a side elevational view of a portion of the spine, having a formable orthopedic fixation system implanted therein.
Figure 10:
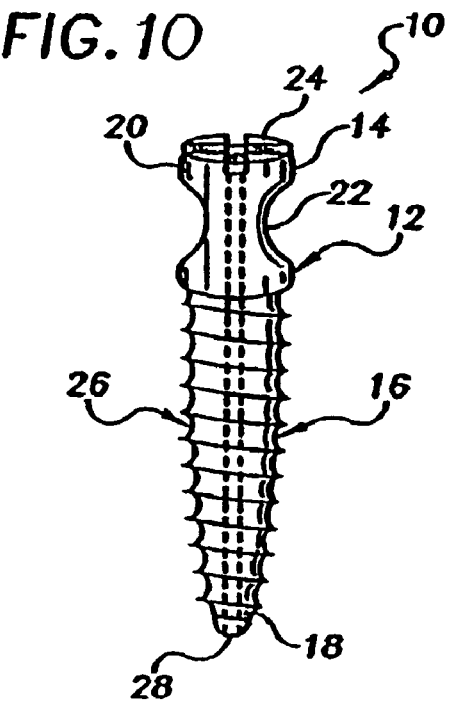
FIG. 10 is a side elevational view of a bone anchor.
Figure 11:
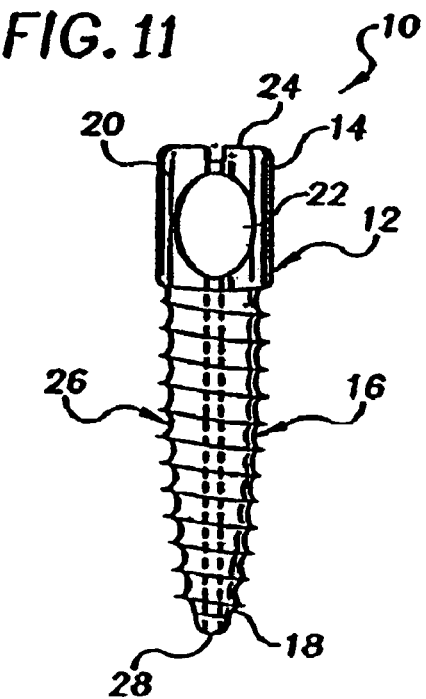
FIG. 11 is a side elevational view of the bone anchor of FIG. 10, rotated 90° about its longitudinal axis.
Figure 12:
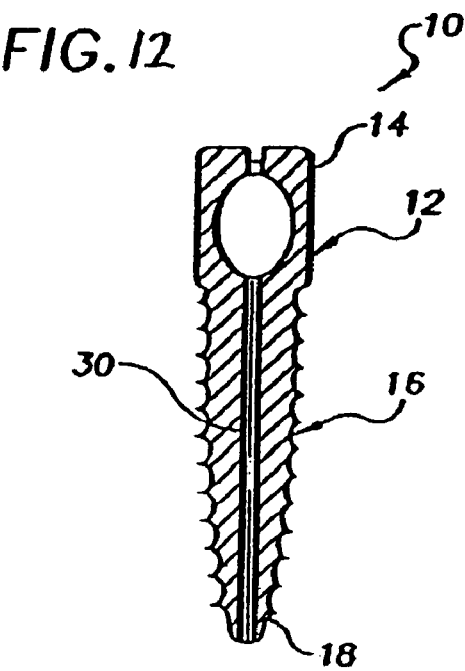
FIG. 12 is a longitudinal cross-sectional view of the bone anchor of FIG. 11.

Referring to FIG. 9, at least one bone anchor 10 may be provided, such as that shown in FIG. 10. The bone anchor 10 includes a first aperture 22, through which the orthopedic device 102 extends. A second bone anchor 10 may also be provided including a second aperture 22, through which the orthopedic device 102 also extends. The first bone anchor 10 is preferably implanted within a first bone. The second bone anchor 10 may be implanted within the second bone. The bones may be adjacent vertebrae or first and second vertebrae spaced apart by one or two or more intermediate vertebrae.

The bone anchors of FIGS. 10-13 are made of a biocompatible material such as titanium or stainless steel. Alternatively, bone anchors 10 may be made of a composite material. Bone anchors 10 may also be made of a suitable medical grade polymer. In one embodiment, bone anchors 10 have a length between about 40 mm and 60 mm, preferably about 50 mm. However, the actual length is dependent on location of the fracture, size of patient, etc.

Bone anchor 10 comprises a proximal portion 12 having a proximal end 14 and a distal portion 16 having a distal end 18. Proximal portion 12 typically comprises a head 20 and a portal 22. In a preferred embodiment, head 20 comprises a proximal portion 24 configured to mate with the tip of a screwdriver. Head 20 may comprise a standard or Phillips slot for mating with the screwdriver. A variety of slot configurations are also suitable, such as hexagonal, Torx, rectangular, triangular, curved, or any other suitable shape. The bone anchor of FIG. 13 has a raised platform 25 having a plurality of substantially straight sides, such as a hexagonal platform, configured to mate with a corresponding depression in the distal end of a screwdriver. Platform 25 may come in a variety of shapes suitable mating with a screwdriver.

Portal 22 of bone anchor 10 may extend through head 20 and is generally between about 4 mm and 8 mm in diameter, preferably about 6 mm to about 8 mm in diameter. Portal 22 may be of any shape suitable for receiving inflatable, implantable orthopedic device 102; however, portal 22 is preferably round.

Figure 13:
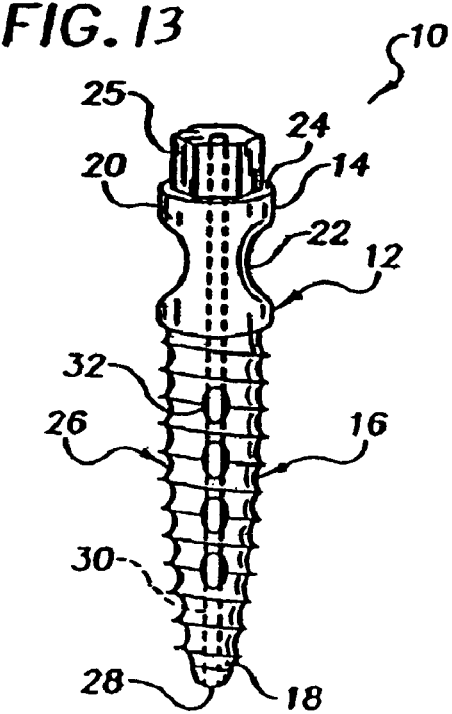
FIG. 13 is a side elevational view of an alternative embodiment of a bone anchor, with bone ingrowth apertures.

Distal portion 16 of bone anchor 10 typically comprises threads 26 and a sharp tip 28. Bone anchor 10 also preferably comprises a central lumen 30 extending coaxially completely through bone anchor 10 from proximal end 14 to distal end 18 and configured to receive a guidewire. Bone anchor 10 may also include at least one perforation 32, as shown in FIG. 13. Perforation 32 may be aligned axially, as shown, or may be staggered axially. Perforation 32 permits bone to grow into bone anchor 10, stabilizing bone anchor 10 within the bone. Additionally, bone matrix material such as a hydroxyapatite preparation can be injected into central lumen 30 and through perforation 32 to promote bone in-growth.

Figure 14:
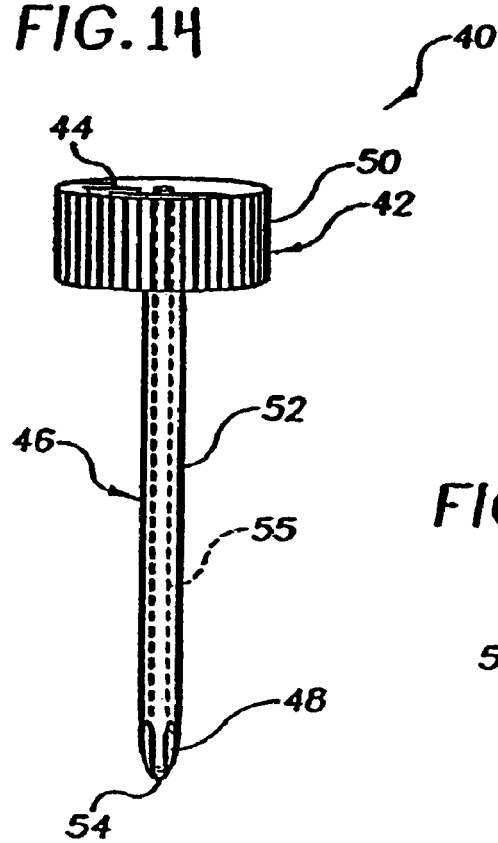
FIG. 14 is a side elevational view of a screwdriver.
Figure 15:
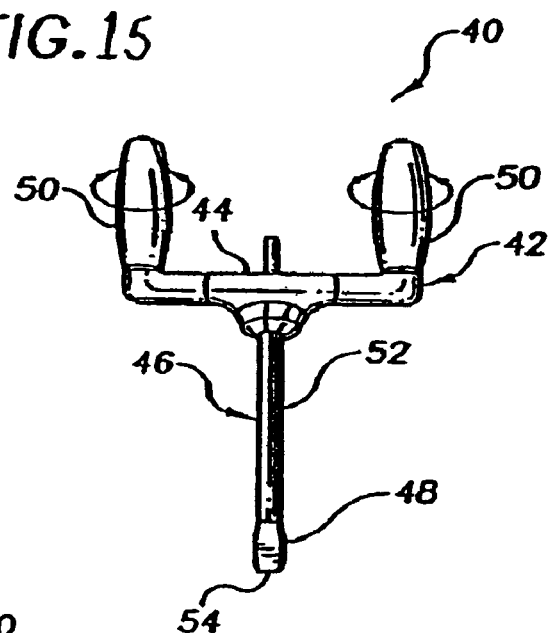
FIG. 15 is a side elevational view of an alternative embodiment of a screwdriver.

FIGS. 14 and 15 show screwdrivers 40 configured to apply torque to bone anchor 10. Screwdriver 40 comprises a proximal portion 42 having a proximal end 44 and a distal portion 46 having a distal end 48. Proximal portion 42 includes a handle 50 configured to permit grasping to apply torque to anchor 10. Various configurations of proximal end 44 are possible. In the embodiment of FIG. 15, the proximal handles 50 may be independently rotatable about their longitudinal axes.

Distal portion 46 comprises a shaft 52 having a tip 54 configured to interface with proximal portion of bone anchor 10. Screwdriver 40 may also comprise a central lumen 55 extending coaxially from proximal end 44 to distal end 48 configured to receive a guidewire.

Figure 16:
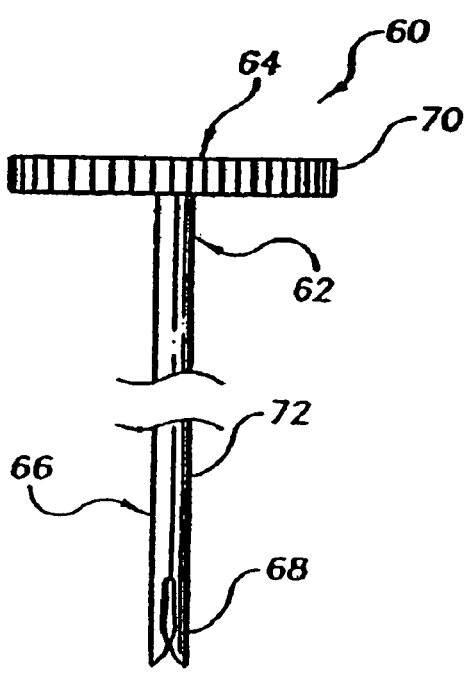
FIG. 16 is a side elevational view of a guidewire directing device.

FIG. 16 shows a guidewire directing device 60, which may be used percutaneously to alter the direction of an advancing guidewire. Guidewire directing device 60 comprises a proximal portion 62 having a proximal end 64 and a distal portion 66 having a distal end 68. Proximal portion 62 comprises a handle 70. Handle 70 is configured to assist in grasping and manipulating guidewire directing device 60. The distal portion 66 comprises a shaft 72 having a fork-tipped end 68. Guidewire directing device 60 engages a guidewire at the fork-tipped end 68. Handle 70 is rotated, advanced, and withdrawn, thereby altering the direction of the advancing guidewire.

Figure 17:
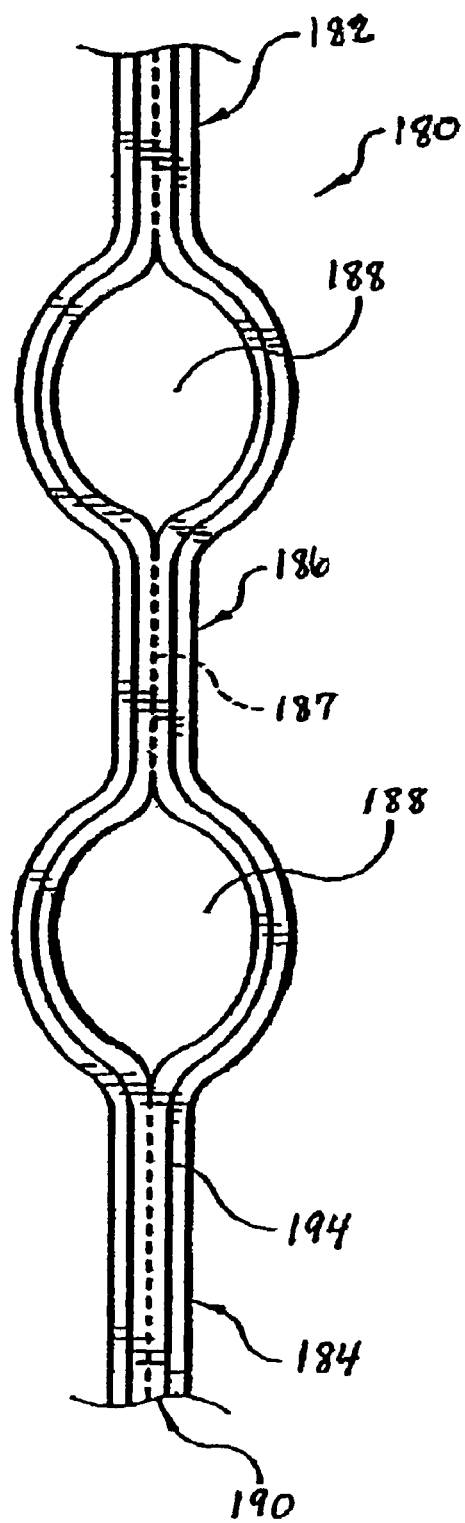
FIG. 17 is a top plan view of a directing sheath.

A directing sheath 180, as shown in FIG. 17, may also be provided for assisting in aligning the guidewire or delivery catheter to pass through bone anchors 10. Directing sheath 180 comprises a proximal portion 182, a distal portion 184, and a central portion 186. Central portion 186 includes at least two openings 188 sized substantially the same as portal 22 of bone anchor 10. Directing sheath 180 preferably includes a lumen 190 extending through its entire length. Lumen 190 is of sufficient diameter to allow a structure such as a guidewire or delivery catheter to pass through. Directing sheath 180 may be scored along its longitudinal axis, on either one line or two opposing lines 192. Scoring 192 allows directing sheath 180 to be split into two separate halves by pulling the sheath apart at its proximal or distal end. Scoring 192 can be partially or completely through the sheath wall.

Directing sheath 180 is preferably formed from a biocompatible polymer. Directing sheath 180 may also include a radiopaque filament 194 passing around each opening in central portion 186 or the entire length of sheath 180. Filament 194 aids in localizing directing sheath 180 after percutaneous placement.

FIG. 44 illustrates the structure of an accelerator for accelerating the curing of the curable media in one embodiment of the invention. In this embodiment, the accelerator comprises a heating coil 300 within the device 102 such as concentrically around the distal end of the inner sleeve 110 of the elongate tubular body 104 of a delivery catheter 100. While the heating coil 300 is shown coiled around the exterior surface of the distal end of the inner sleeve 110, it can also be fitted inside the distal end of the inner sleeve 110, or embedded within the distal end of the inner sleeve 110. The distal portion of the sleeve 110 may be provided with a detachable joint at the proximal end 116 of the balloon 114 such that it is left behind within the implantable device 102 following removal of the delivery catheter 100. A variety of releasable attachments may be used, such as threaded engagements, bayonet mounts, quick twist engagements like luer lock connectors, or others known in the art.

Figure 45:
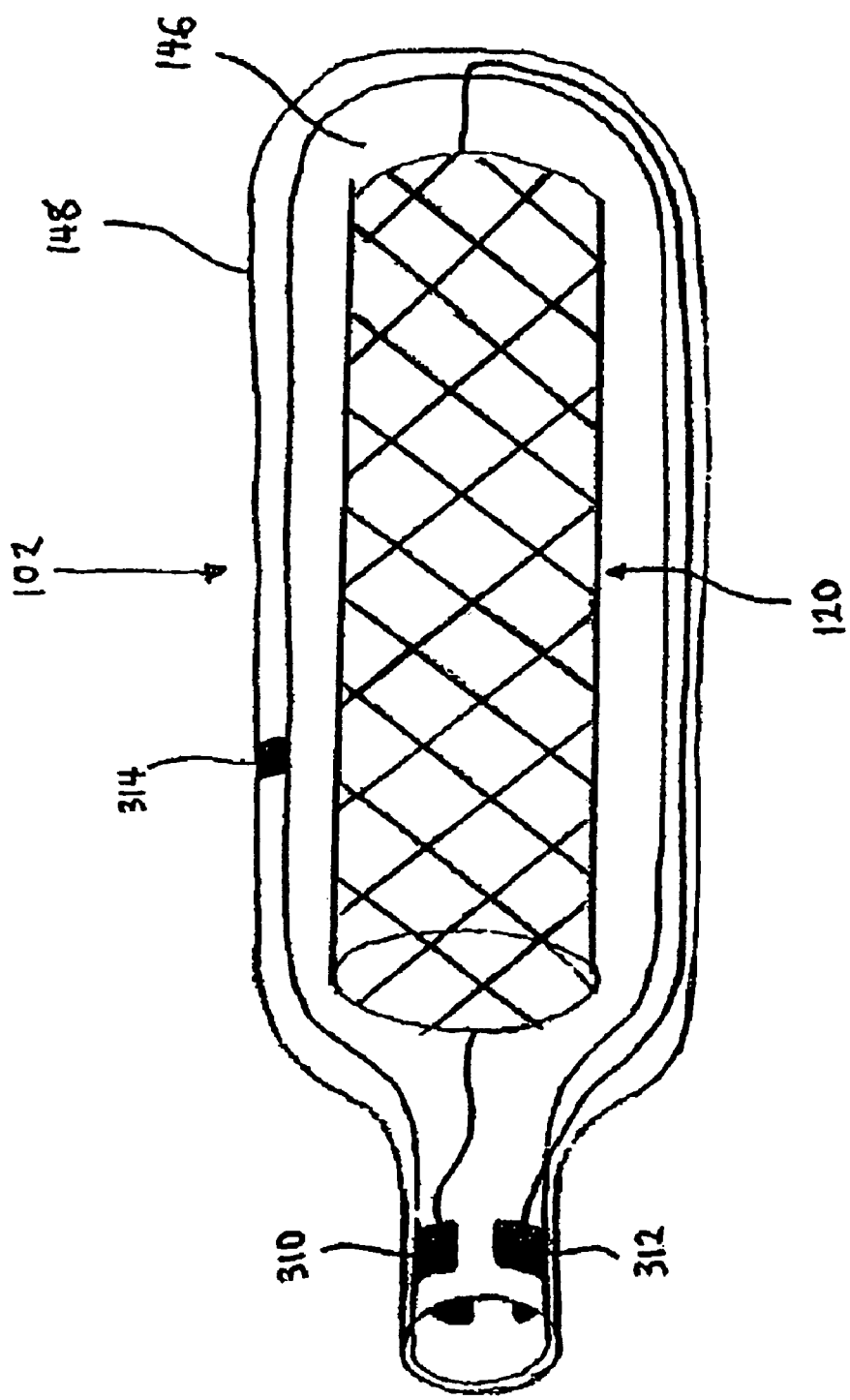
FIG. 45 is a schematic side elevational view of an implant having an alternate heating element.

The accelerator is not necessary a part of the delivery catheter 100. FIG. 45 schematically illustrates another embodiment in which the accelerator is built into the inflatable orthopedic device 102. As disclosed above, a variety of structures may be provided as reinforcement element 120 in the cavity 146 of the balloon 114, such as carbon fibers, titanium rods, or tubular stents. If the reinforcement element 120 is made from electrically conductive materials, it can also function as a resistive heating element. In FIG. 45 a metallic stent is illustrated. Titanium rods and carbon fibers may also be used. Electrical contacts 310 and 312 for conducting a current through the reinforcement element 120 are incorporated into the releasable attachment, such as a concentric sliding fit connection, used between the outer sleeve 112 and/or inner sleeve 110 and the proximal end 103 of the balloon 114. These electrical contacts engage complimentary contacts on the outer sleeve 112 and/or inner sleeve 110 to complete an electric circuit with a proximally located power supply for running the resistive heating element.

In order to accomplish the objective of accelerating polymerization of the epoxy or other hardenable media, the heating element preferably elevates the temperature of the epoxy to a point above normal body temperature. Temperatures at the heating element of at least about 43°, preferably at least about 50°, and, under certain circumstances as high as 60° C. or more are desirable to produce an optimal cure rate. However, the outside of the implant is preferably not heated to the extent that it causes localized tissue necrosis. Tissue necrosis occurs at approximately 45° C. Thus, the heat source preferably sets up a temperature differential between the surface of the implant and the interior of the implant. This may be accomplished in several ways; such as, for example, selecting materials and thickness of the outer flexible wall 148 to provide thermal insulation of the adjacent tissue from heat generated by the heating element. As an alternative or in addition, heat sink structures may be provided at or near the outer surface of the orthopedic device 102. A flow path such as an annular space formed within a double walled balloon may be utilized to circulate a coolant such as saline or other circulating cooling fluid. Such measures preferably permit the heating element to be heated as high as 50° C. or higher, while maintaining the outside surface of the device 102 at a temperature of no more than about 45° C., and, preferably no more than about 43° C.

Excessive temperature can also be reached transiently, such as at the beginning of a heating cycle when the temperature may temporarily overshoot the 45° C. desired maximum. The present inventors have determined that the initial temperature overshoot can be eliminated or reduced by appropriately driving the power to the heating element as is discussed in detail below. The driver circuitry preferably brings the heating element up to operating temperature rapidly, while minimizing the risk of thermal overshoot beyond a predetermined maximum. All of the foregoing measures preferably allow a sufficient curing of the hardenable media to limit the required period of immobility to no more than about 2 hours, preferably no more than about 1 hour and, optimally no more than about 45 minutes post implantation. Although a complete cure is not required within this time window, a sufficient cure is desirable that the patient need not be immobilized beyond the initial cure. Thereafter, the hardenable media will continue to harden, such as over the next few hours or even days, but with little or no restriction on the patient's activities.

The resistive heating element, whether the heating coil 300, the reinforcement element 120, or other structure, may be made from material with either a positive or negative temperature coefficient of resistance, e.g., electrical resistance either directly or indirectly proportionate to temperature, respectively. The temperature may be monitored by measuring the DC voltage across the resistive heating element, for the voltage is directly proportional to resistance for a given current, and the temperature coefficient of resistance is known. Alternatively, by measuring the voltage, current and phase of the drive system, the resistance of the heating element and thus its temperature can be calculated by a microprocessor or dedicated circuitry.

Alternatively a thermistor 314 may be used to monitor the temperature of the inflatable orthopedic device 102. Thermistors are well known in the art. Using one or more separate thermistors 314 would entail more electrical contacts (not shown) as another electrical loop in addition to the one running the heating element may be necessary. Other methods of measuring the temperature include the use of an optical fiber in conjunction with a thermally reactive material, a coaxial plunger in conjunction with a thermal bulb, or a semiconductor temperature sensor or junction (such as a diode) carried by the orthopedic implant. A bimetallic heating element may function similarly to a circuit breaker and self-regulate.

Figure 46:
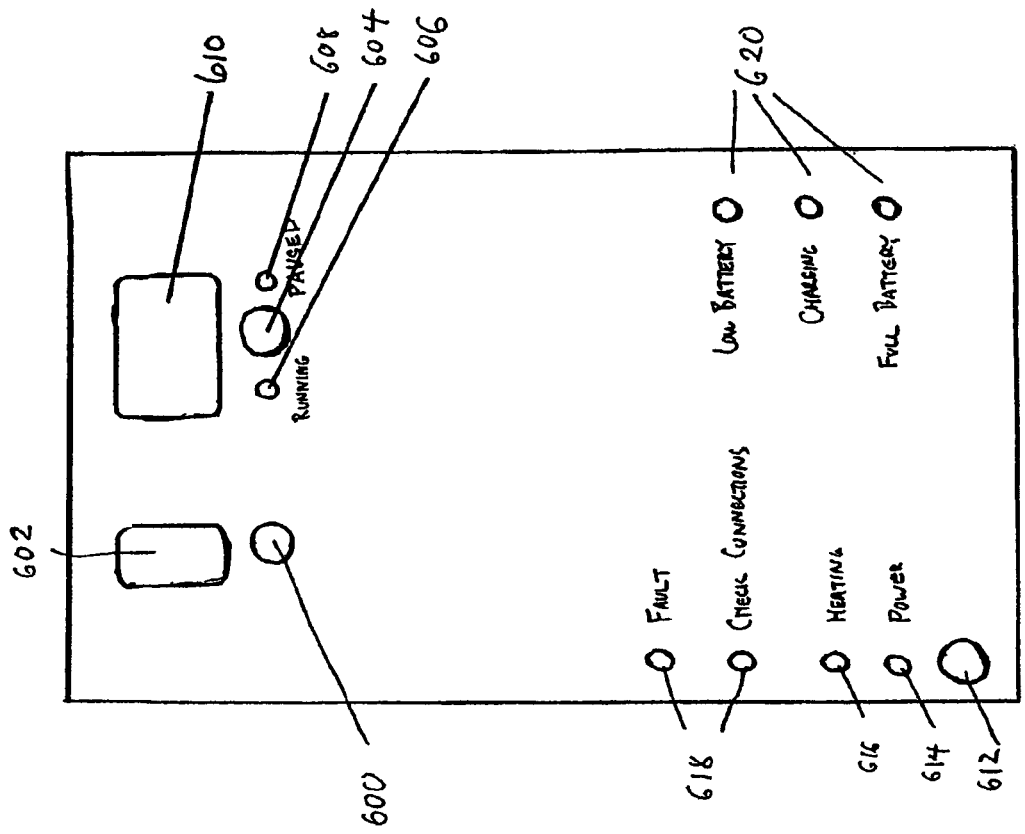
FIG. 46 is a frontal view of the control panel for the heating element.

FIG. 46 illustrates one embodiment of the control panel 316 for the heating element 300, in electrical communication with catheter manifold 124. The heating cycle selected and the time elapsed/remaining in the cycle are displayed. Each heating cycle is associated with a heating profile, a table of target temperatures at different points of time in the heating cycle. A button may be used to toggle the display between elapsed and remaining time. There is also a power switch, a selector for the heating cycle, and a run/pause button to interrupt the heating cycle. LED's or other indicators may be used to indicate whether the heating cycle is running or paused. LED's may also be used to indicate the status of the battery—low, charging or full, the status of the control block—on or off, and the status of the heating element—heating or not. The heating indicator is preferably configured to light when the heating element is first active, and blink when the temperature of the heating element is regulated via the heating profile. Ideally the control block 324 is provided with circuitry that detects faults and problems with the connection. These problems may be communicated to the user via LED's and/or audible alarms.

The illustrated embodiment of the control panel 316 has a cycle button 600 with which to select the heating cycle, and a cycle window 602 to display the cycle selected. The control panel 316 is also provided with a pause switch 604 to pause the heating cycle, and LED's 606 and 608 respectively to indicate whether the cycle is running or paused. A time window 610 indicates the time elapsed in the heating cycle. An optional toggle switch (not shown) may be used to toggle the time window 610 to display the time remaining in the heating cycle. A power switch 612 turns the control panel on and off while a power LED 614 displays its power status. A heating LED 616 indicates whether the heating cycle is in a heating phase. Warning LED's 618 indicate whether there is a fault in the circuitry or connection with the heating element 300. Battery LED's indicate the charge status of the battery.

Figure 47:
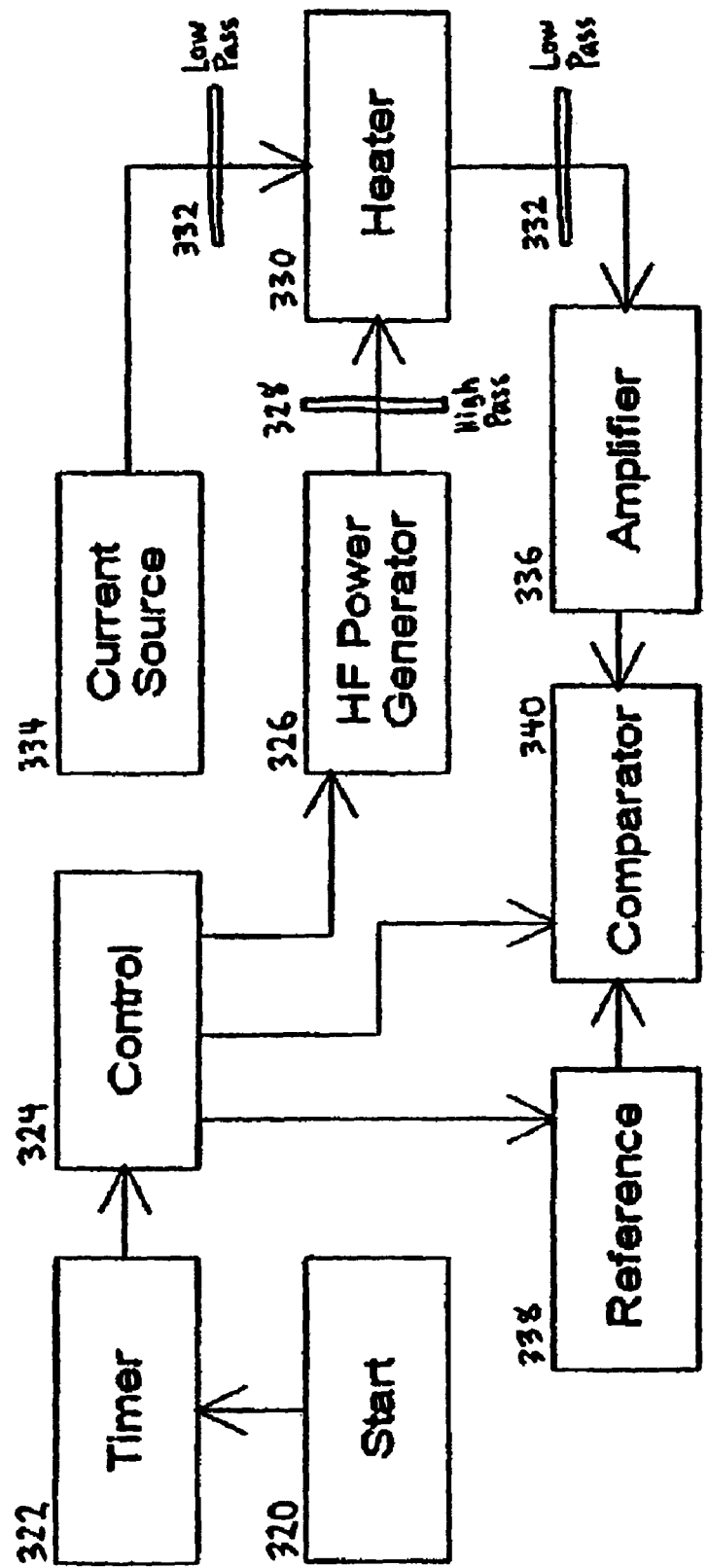
FIG. 47 is a block diagram of a driver circuit for driving a heating element in accordance with the present invention.

FIG. 47 is a simple block diagram of a control circuitry of the heating element in one embodiment. This circuit allows optimization of the heating cycle, by heating the heating element rapidly to the desired temperature but minimizing the risk of a thermal overshoot beyond the target temperature which would have created a risk of thermally induced necrosis. A start switch 320 begins a heating cycle and a timer 322. A control block 324, controlled via the control panel 316, stores a heating profile and controls the circuitry described below. A programmable pulse width modulated power source is used as a high frequency power generator 326 to supply power, through a high-pass filter 328 to the heating element 330. The high frequency power generator 326 ideally operates at a frequency above the biological bandwidth. While any circuitry operating at frequencies above 2 kHz would fit this description, frequencies above 10 kHz are preferable. In one embodiment the high frequency power generator 326 operates at 125 kHz, and in another it operates at 128 kHz.

Low-pass filters 332 isolate the high frequency power generator 326 from a precision current source 334 and an amplifier 336. The precision current source 334 feeds a low precise DC current through the heating element 330. The resulting DC voltage across the heating element 330 is amplified by the amplifier 336 and compared against a reference voltage generated by a reference module 338. The comparison is done by a level comparator 340. As voltage is directly proportionate to resistance at a given current, the resistance across the heating element 330 can thus be measured. With the temperature coefficient of resistance of the heating element 330, the temperature of the heating element 330 can thus be calculated. The control block 324 acts on feedback from the comparator 340 to enable or disable the high frequency power generator 326, and thus regulate the temperature of the heating element 330 according to the heating profile. In one embodiment a clinical practitioner may have the option of overriding the heating profile by inputting the desired temperature into the control block 324 directly. While a resistive heat source has been described in some of the above embodiments, other energy sources to accelerate the curing of the curable media may be used. These include, but are not limited to, adding a polymerizing agent, radio frequency, ultrasound, microwave and lasers. Also, the complete curing of the curable media by the described apparatus and methods is not always required to occur before discontinuing the heat source or other initiator step in these embodiments. When the curable media has been partially cured to a certain level of structural integrity, the patient does not have to be retrained for the remaining cure time necessary to achieve a complete cure. Thus the period of patient immobilization is minimized using the curing accelerators of the present invention.

Another specific embodiment is described in connection with FIGS. 48 through 51. Although certain specific materials and dimensions will be disclosed below, these are exemplary only and may be varied as will be understood by those of skill in the art. FIG. 48a is an overview of a heated inflatable orthopedic balloon 400. The distal end 402 of the balloon 400 is sealed with a silicone adhesive. This silicone adhesive also holds the distal marker 404 in place. The distal marker 404 may be made of various materials, including gold, platinum or tantalum. An inner tubing 406, made of PET, runs from the distal tip 402 along the axis of the balloon 400 to the proximal end. The inner tubing 406 is porous, to allow the curable media to flow radially outwardly therethrough. A heating element 408, such as a coated tungsten wire, is coiled around the inner tubing 406. In the illustrated embodiment, the heating element 408 is coiled in a parallel double-stranded fashion around the inner tubing 406, with the two strands joined in a loop 410 towards the distal end 402 to form a continuous electrical pathway. Carbon fibers are provided in the space 412 between the inner tubing 406 and the outer wall 414 of the balloon 400. The carbon fibers may have a diameter of between 0.003 to 0.007 inches. They are bundled in tows of about 3,000 to about 12,000 fibers. A typical carbon fiber suitable for such use is made by Hexcel Carbon Fibers, Salt Lake City, Utah, Part No. HS/CP-5000/IM7-GP 12K. Tow tensile strength in the range of about 5,000 to about 7,000 Mpa may be achieved. Tow tensile modulus may be within the range of about 250 to 350 Gpa. As noted above, in embodiments wherein the hardenable media alone has sufficient strength, the carbon fibers may be omitted.

FIG. 48b is an enlarged view on the proximal portion of the balloon 400. The inner tubing 406 terminates at about the proximal end 416 of the balloon 400. The proximal end 416 comprises a nylon tubular support structure 417. Both the proximal marker 418 and the valve assembly 420 are held in place in the tubular support 417 by a silicone adhesive. Two concentric electrical connector rings are also supported by the support structure 417. The inner electrical connector ring 422 is smaller in diameter, and located more distally, than the outer electrical connector ring 424. Each end of the heating element 408 is electrically joined to one of these electrical connector rings. A seal 426 is provided at the proximal tip of the tubular support 417. The proximal end 416 is shaped with an annular reduction in diameter such that a bottleneck 428 is formed just distal of the seal 426.

Figure 48C:
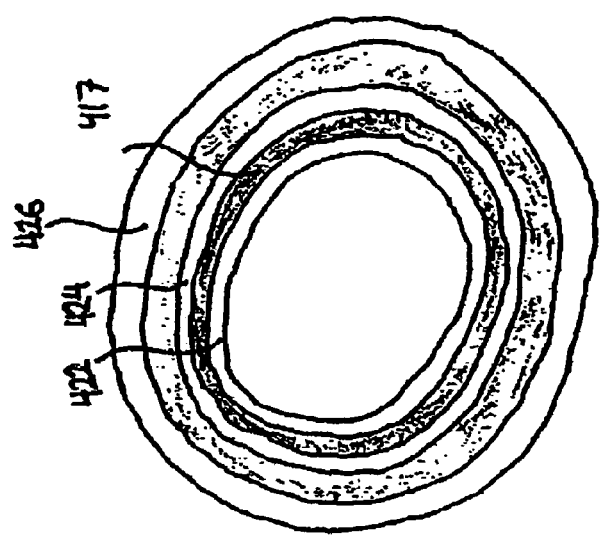
FIG. 48C is an end view taken along the line 48C-48C of FIG. 48B.

FIG. 48c is an end view of the proximal end 416 along the axis of the balloon 400.

Figure 49:
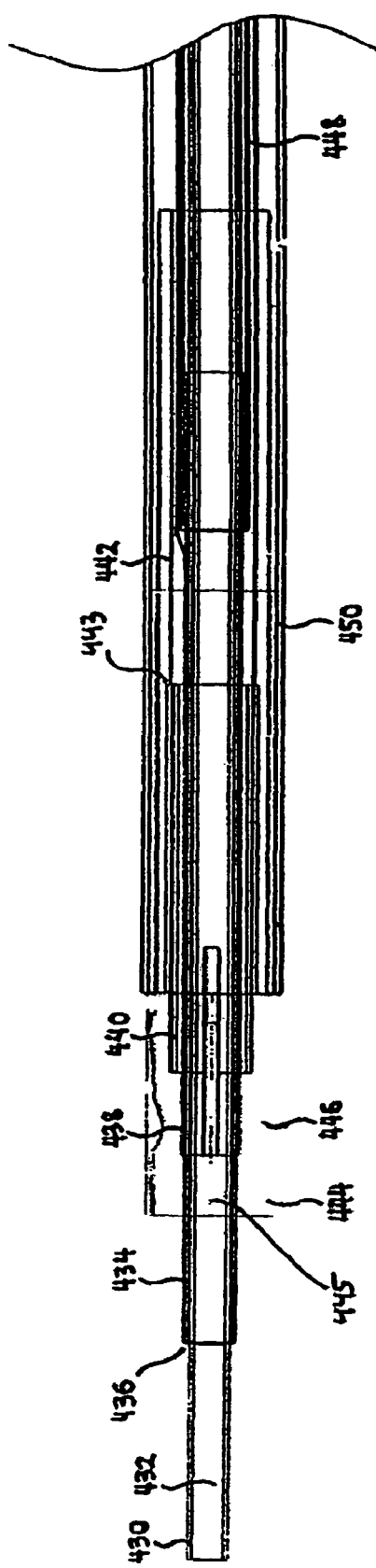
FIG. 49 is a side elevational schematic view of the distal end of a deployment catheter in accordance with the present invention, with the implant removed.

FIG. 49 is an enlarged view of the distal end of the catheter, with the balloon 400 removed. The innermost tube is the injection tube 430. The lumen therein is the injection lumen 432. The injection lumen 432 extends proximally to an injection port on the proximal end of the catheter. The injection tube 430 is coaxially arranged within the suction tube 434. An annular space between the outside surface of the injection tube 430 and the inside surface of the suction tube 434 defines the suction lumen 436. The suction lumen 436 communicates with a suction port on the proximal end of the catheter.

The inner electrical connector tube 438 is coaxially carried by the exterior perimeter of the suction tube 434. The outer electrical connector tube 440 is coaxially arranged around the exterior perimeter of the inner electrical connector tube 438. A layer of electrical insulation is provided between the two electrical connector tubes 438 and 440. This can be accomplished by coating the inner surface of the outer electrical connector tube 440 or the outer surface of a proximal portion of the inner electrical connector tube 438 with an electrically insulating material, such as polyurethane or PTFE. Both electrical connector tubes 438 and 440 may be slotted to ease connection, as discussed below. A wire connects each electrical connector tube to the drive circuit of the heating element 408. Each electrical connector tube may have an additional wire connected to it, which may be used together as a dedicated feedback loop to more accurately measure the electrical resistance of the heating element 408. A spacer tube 442 is provided with a notch 443 which provides an annular seat for the proximal end of the outer electrical connector 440, to hold the outer electrical connector tube 440 in place.

A lock tube 444 is coaxially arranged around the exterior perimeter of the spacer tube 442. The lock tube 444 is provided with one or two or more axially extending slits 445 and provided with a radially inwardly extending projection 446 for releasable engagement with a corresponding annular recess on the proximal end of the balloon 400, as discussed below. The inner tube 448 holds the suction tube 434 and the injection tube 430, as all three extend all the way proximally into the catheter handle. The outer tube 450 terminates proximally at a luer lock at the distal end of the catheter handle.

Figure 50:
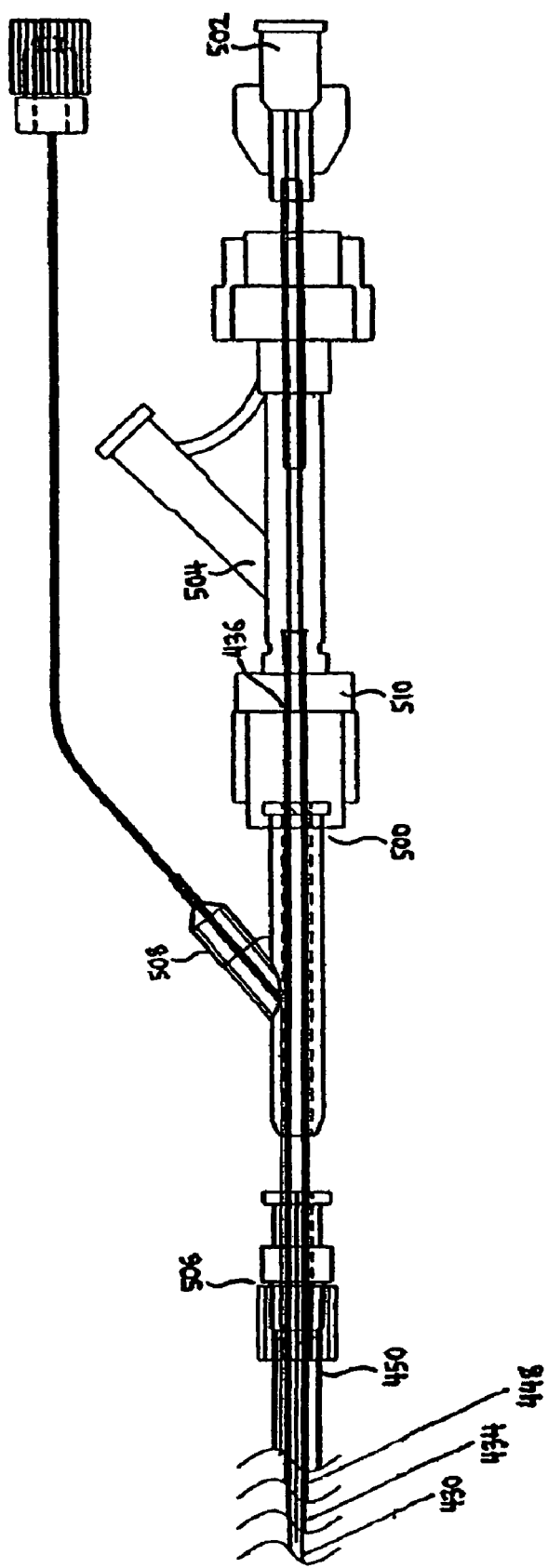
FIG. 50 is a side elevational schematic view of the proximal end of the deployment catheter illustrated in FIG. 49.

FIG. 50 illustrates the proximal connections of the injection tube 430, the suction tube 434, the inner tube 448 and the outer tube 450 to the catheter handle 500. As discussed above, the injection tube 430 is connected to an injection port 502. The suction lumen 436, defined by the space between the injection tube 430 and the suction tube 434, opens into the suction port 504. The inner tube 448 extends into the catheter handle 500, while the outer tube 450 terminates at a luer lock 506 at the distal end of the catheter handle 500. The wires connecting the electrical connector tubes 438 and 440 are routed through an electrical port 508. A luer lock 510 allows both injection tube 430 and suction tube 434 to be removed from the catheter following injection of a curable medium into the balloon 400, as will be discussed below.

Referring to FIGS. 48a, 48b, 49, and 50, the attachment of the catheter to the balloon 400 is now described. As described above, the injection tube 430 and the suction tube 434 of the catheter are coaxial, with the injection tube 430 inside the suction tube 434. The injection tube 430 extends through the inner tubing 406 into or close to the distal end 402 of the balloon 400. The suction tube 434 extends through the valve assembly 420 of the balloon 400 to a point just distal of the proximal marker 418. The valve assembly 420 thus seals around the exterior surface of the suction tube 434.

When the catheter is attached to the balloon 400, the inner electrical connector tube 438 contacts the inner electrical connector ring 422, and the outer electrical connector tube 440 contacts the outer electrical connector ring 424. As described above, both electrical connector tubes are slotted to ease their insertion into the respective electrical connector rings. These two contacts complete the electric circuit between the heating element 408 and its drive circuitry.

The lock tube 444 holds the balloon 400 in place at the end of the catheter. A seal 426 at the proximal end 416 of the balloon 400 seals against the interior surface of the lock tube 444. As described above, the lock tube 444 is slit to ease its insertion over the proximal end 416 of the balloon 400. One or more radially inwardly extending projections 446 provided on the interior surface of the lock tube 444 complements the bottleneck 428 in the proximal end 416 of the balloon 400 to provide an interference engagement which is maintained by the outer tube 450. The outer tube 450 may be released via the luer lock 506, allowing it to slide distally over the lock tube 444 to restrain the projection 446 of the lock tube 444 within the bottleneck 428 of the balloon 400.

Any of a variety of releasable connectors may be utilized, between the catheter and the implant. For example, threaded connections, twist locks, interference fit and friction fit structures are well known in the art. In general, a releasable connection which will withstand sufficient tension and compression during the positioning process is preferred. Such structures will generally include an interference fit. In the illustrated embodiment, a radially inwardly extending annular ridge which is provided with two or more axially extending slots to allow lateral movement cooperates with a radially inwardly extending annular recess on the proximal end of the implant as has been discussed. The radially inwardly extending ridge provides an interference surface, which may also be carried by one or more lever arms or other support structures. The relationship may alternatively be reversed between the deployment catheter and the implant, such that one or more radially outwardly extending projections on the implant engage a radially outwardly extending recess on the interior wall of the deployment catheter. In general, a positive interference fit can be readily accomplished by a first locking surface on the catheter which is removably engaged with a second, complementary locking structure on the implant. Preferably, one of the first and second locking structures is laterally moveable to engage and disengage the implant, and a lock is provided for releasably locking the first and second engagement surfaces to releasably retain the implant on the catheter.

Figure 51:
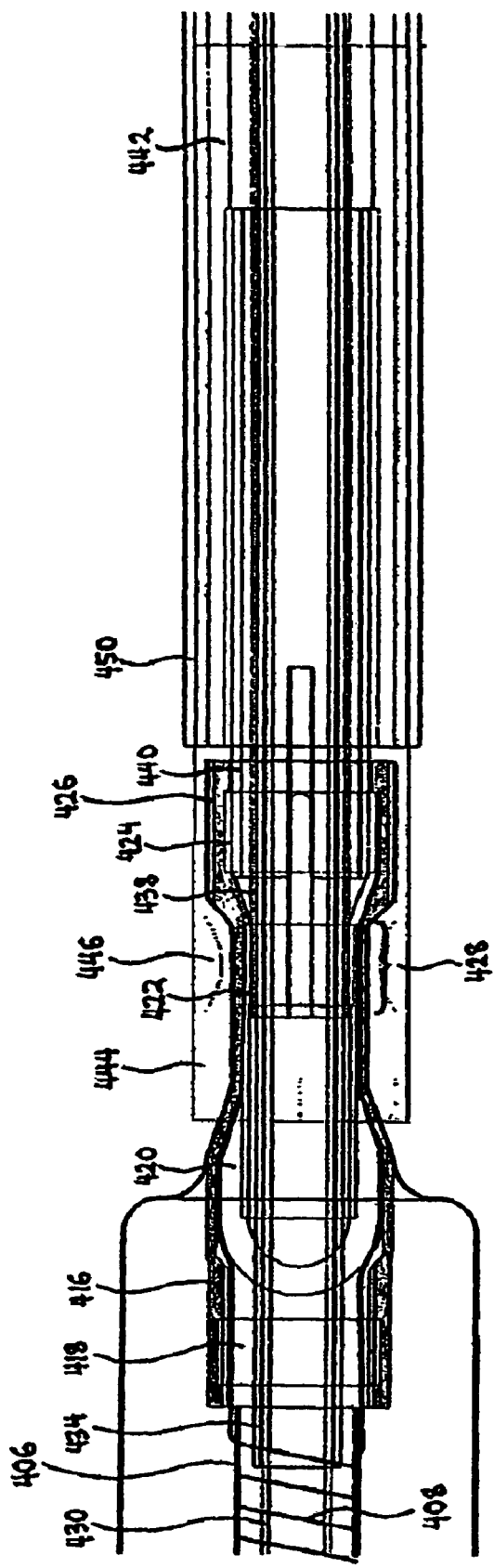
FIG. 51 is a side elevational view of the removable junction between the distal end of the deployment catheter and the proximal end of the implant.

FIG. 51 illustrates the proximal end of the balloon 400 attached to the distal end of the catheter as described above.

Figure 52:
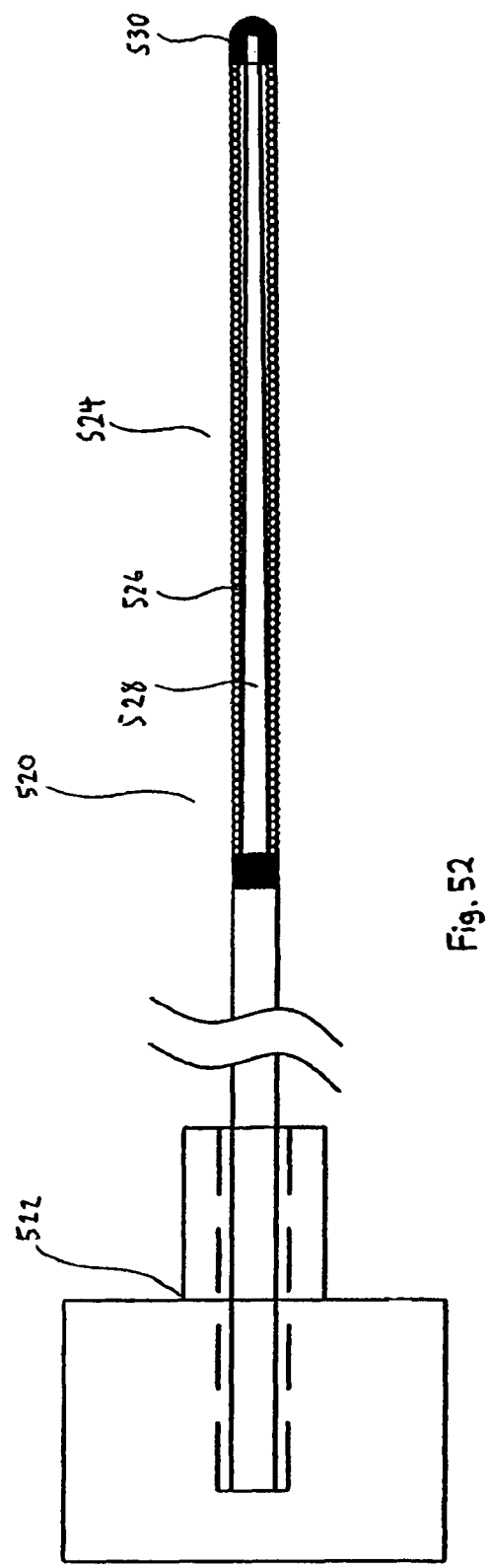
FIG. 52 is a side elevational view of a stiffening wire in accordance with one aspect of the invention.

FIG. 52 illustrate an embodiment of a stiffening wire 520 used to facilitate the insertion of the catheter. The stiffening wire 520 comprises an elongate flexible body, having a proximal end and a distal end. A handle 522 is provided at its proximal end. The length of the wire is sufficient to provide support to the catheter during insertion, and thus may be varied depending on the catheter dimensions which are discussed elsewhere herein. Diameters are also based upon the ID of the inflation lumen of the intended catheter. In one embodiment, the wire comprises an 0.050 inch OD wire or tube, which may be stainless steel or other material. A lubricious coating, such as PTFE may also be provided. To achieve more flexibility in distal region 524, the wire or tube may taper throughout a tapered zone 528 to a smaller OD distally. A coil spring 526 may be carried concentrically around the tapered zone 528, and attached at a distal tip 530. This allows the guide wire to be increasingly flexible distally.

The deployment and release of the inflatable orthopedic balloon 400 is now described. A guide wire may be inserted into the injection lumen 432 to stiffen the entire catheter to facilitate insertion of the balloon 400. This guide wire may be inserted via the injection port 502. Ideally this guide wire extends all the way to the distal end 402 of the balloon, and has a diameter that permits axial movement within the inner diameter of the injection tube 430. The insertion of the balloon 400 may be visualized by fluoroscopy of the distal marker 404 and the proximal marker 418. The guide wire is removed prior to the injection of curable medium into the balloon 400 via the injection lumen 432.

The injection port 502 is then connected to a pump, which pumps curable medium into the balloon 400 through the injection tube 430. As the injection tube 430 in the illustrated embodiment extends through the inner tubing 406 into or close to the distal end 402 of the balloon 400, the balloon is filled from the distal end 402 first. A vacuum is connected to suction port 504. As described above, the suction tube 434 extends through the valve assembly 420 of the balloon 400 to a point just distal of the proximal marker 418, and the inner tubing 406 of the balloon 400 is porous. This suction thus contributes to the filling of the balloon 400 with curable medium.

After the space 412 (as defined by the volume between the inner tubing 406 and the outer wall 414 of the balloon 400) is filled with curable medium, the luer lock 510 may be disengaged to allow the removal of the injection tube 430 and the suction tube 434. Any space remaining in the inner tubing 406 is filled with curable medium as the injection tube 430 is slowly pulled out. The valve assembly 420 of the balloon 400 prevents any curable medium from leaking.

For those embodiments in which heating is used to accelerate the curing of the hardenable media, a high frequency current is passed through the heating element 408 to accelerate the curing of the curable medium in the balloon 400, as has been discussed above in FIG. 47.

After the completion of the heating cycle (if performed), the catheter is removed from the balloon 400 by first sliding outer tube 450 proximally, exposing the lock tube 444. As described above, the lock tube 444 is slit. Without the outer tube 450 around it, the rounded proximal surface of projection 446 of the lock tube 444 will slide over and off the bottleneck 428 of the balloon 400 as the catheter handle 500 is pulled proximally. This action will also disengage the inner electrical connector tube 438 from the inner electrical connector ring 422 and the outer electrical connector tube 440 from the outer electrical connector ring 424. The balloon 400 is thus left in place after the removal of the catheter.

Although the application of the present invention will be disclosed in connection with connecting two adjacent vertebrae, the methods and structures disclosed herein are intended for various other applications such as to connect three or more vertebrae, as will be apparent to those of skill in the art in view of the disclosure herein. In addition, the method may be used to stabilize the L5 vertebrae, using the cranial-ward portion of the sacrum as the vertebrae with which L5 is anchored. Furthermore, although the method is disclosed and depicted as applied on the left side of the vertebral column, the method can also be applied on the right side of the vertebral column, or both sides of the vertebral column sequentially or simultaneously.

The method of the present invention involves percutaneously inserting one or more fusion devices into two or more than two adjacent vertebrae, either unilaterally or, preferably bilaterally, where a portion or all of at least one of the vertebrae is unstable, separated or displaced. The fusion devices reposition or fix the displaced vertebra or portion of the displaced vertebra to a position within the vertebral column which is more stable or which causes less morbidity.

Referring now to FIG. 18 through FIG. 28, there are shown a series of drawings depicting various stages of the method of repositioning and fixing a displaced vertebra or portion of a displaced vertebra, unilaterally, according to the present invention. FIGS. 18-28 show partial cutaway, perspective, midline sagittal views of a portion of a vertebral column undergoing the method of the present invention.

The method will now be disclosed and depicted with reference to only two vertebrae, one which is either unstable, separated or displaced and one of which is neither unstable, separated nor displaced. However, the method can also be applied to three or more vertebrae simultaneously, as will be understood by those with skill in the art with reference to this disclosure. Additionally, the method can be used to stabilize the L5 vertebrae, using the cranial-ward portion of the sacrum as the "vertebrae" with which L5 is anchored. Further, though the method is disclosed and depicted as applied on the left side of the vertebral column, the method can also be applied on the right side of the vertebral column or, preferably, can be applied on both sides of the vertebral column, as will be understood by those with skill in the art with reference to this disclosure.

First, the present method comprises identifying a patient who is a suitable candidate for undergoing the method. In connection with a spinal application, a suitable candidate has one or more unstable vertebrae, one or more portions of one or more vertebrae at least partly separated from the remainder of the vertebrae, one or more portions of one or more vertebrae at least partly separated from the remainder of the vertebrae with potential or complete separation, or has one or more vertebrae or a portion of one or more vertebrae displaced from its normal position relative to the vertebral column, or has one or more portions of one or more vertebrae at least partly separated from the remainder of the vertebrae and displaced from its normal position relative to the vertebral column. Further, the suitable candidate will normally have either pain, loss of function or real or potential instability which is likely due to the separation or displacement, or separation and displacement. If only a portion of the vertebra is unstable, separated or displaced, the portion of the vertebra that is unstable, separated or displaced will generally include at least part of the vertebral body and adjoining pedicle. However, other unstable, separated or displaced portions of a vertebra can be repositioned or fixed using the present method, as will be understood by those with skill in the art with reference to this disclosure. For example, a suitable patient can have a disease or condition such as spondylosis, spondylolisthesis, vertebral instability, spinal stenosis and degenerated, herniated, or degenerated and herniated intervertebral discs, though actual indications require the expertise of one of skill in the art as will be understood by those with skill in the art with reference to this disclosure.

Next, the present method comprises making a stab incision in the patient's skin overlying the patient's vertebral column at or near the level of the vertebrae or portion of vertebrae to be repositioned or fixed. In one embodiment, the incision is made at or near the level of the pedicle of the vertebra or portion of vertebra to be repositioned or fixed. The pedicle level is located preferably by identifying the pedicle shadow using fluoroscopy. In a preferred embodiment, the stab incision is made using a #11 scalpel blade.

Figure 18:
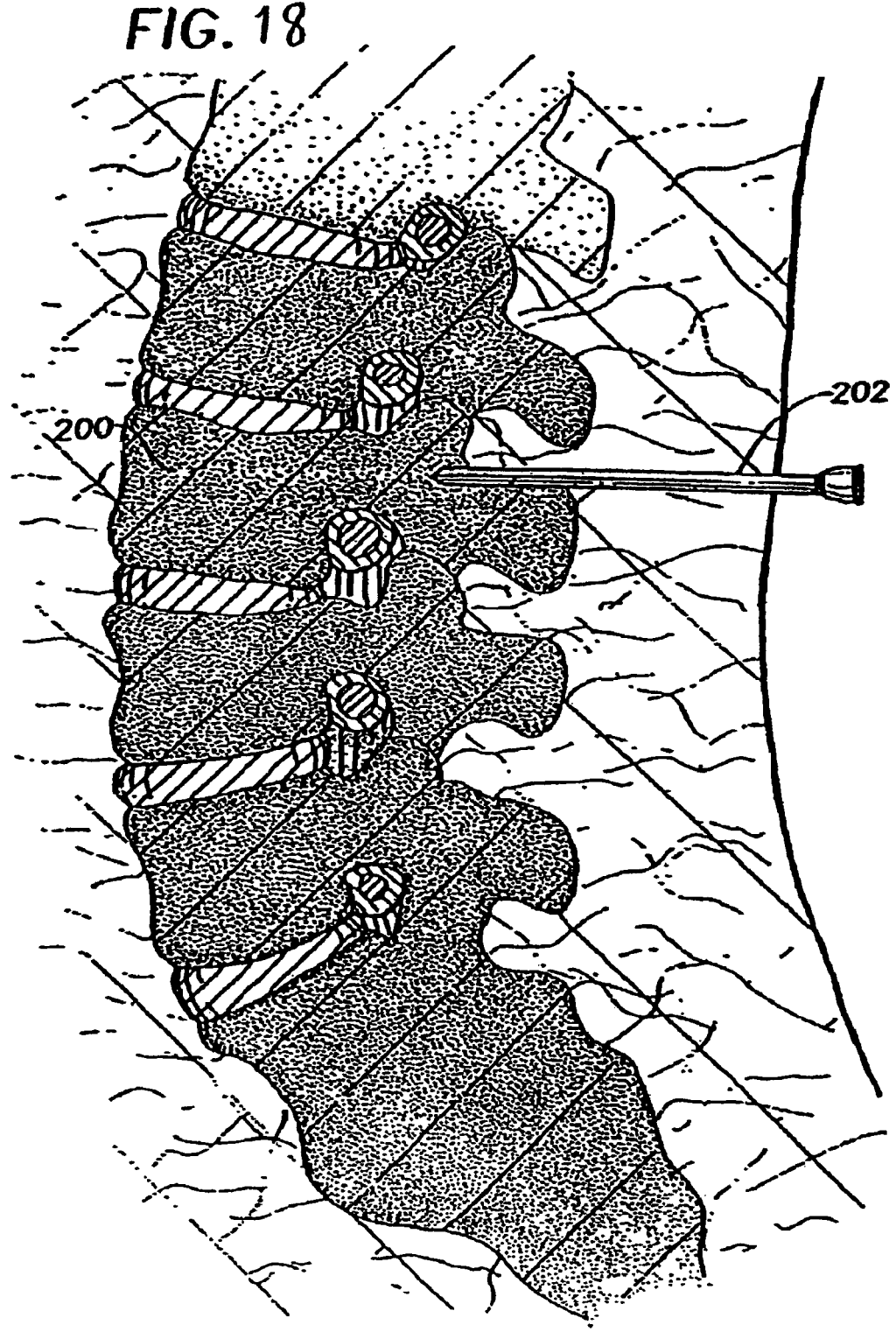
FIGS. 18-28 are partial cross-sectional midline sagittal views of a portion of a vertebral column showing an implantation method of the present invention.

Then, as shown in FIG. 18, an 11-gauge bone biopsy needle 202 or its equivalent is placed through the stab incision to create a tract to the posterior periosteal surface of the vertebra 200 which is to be stabilized, repositioned or fixed. Next, the biopsy needle 202 is used to make a small incision in the periosteum and into the cortex of the vertebrae.

Figure 19:
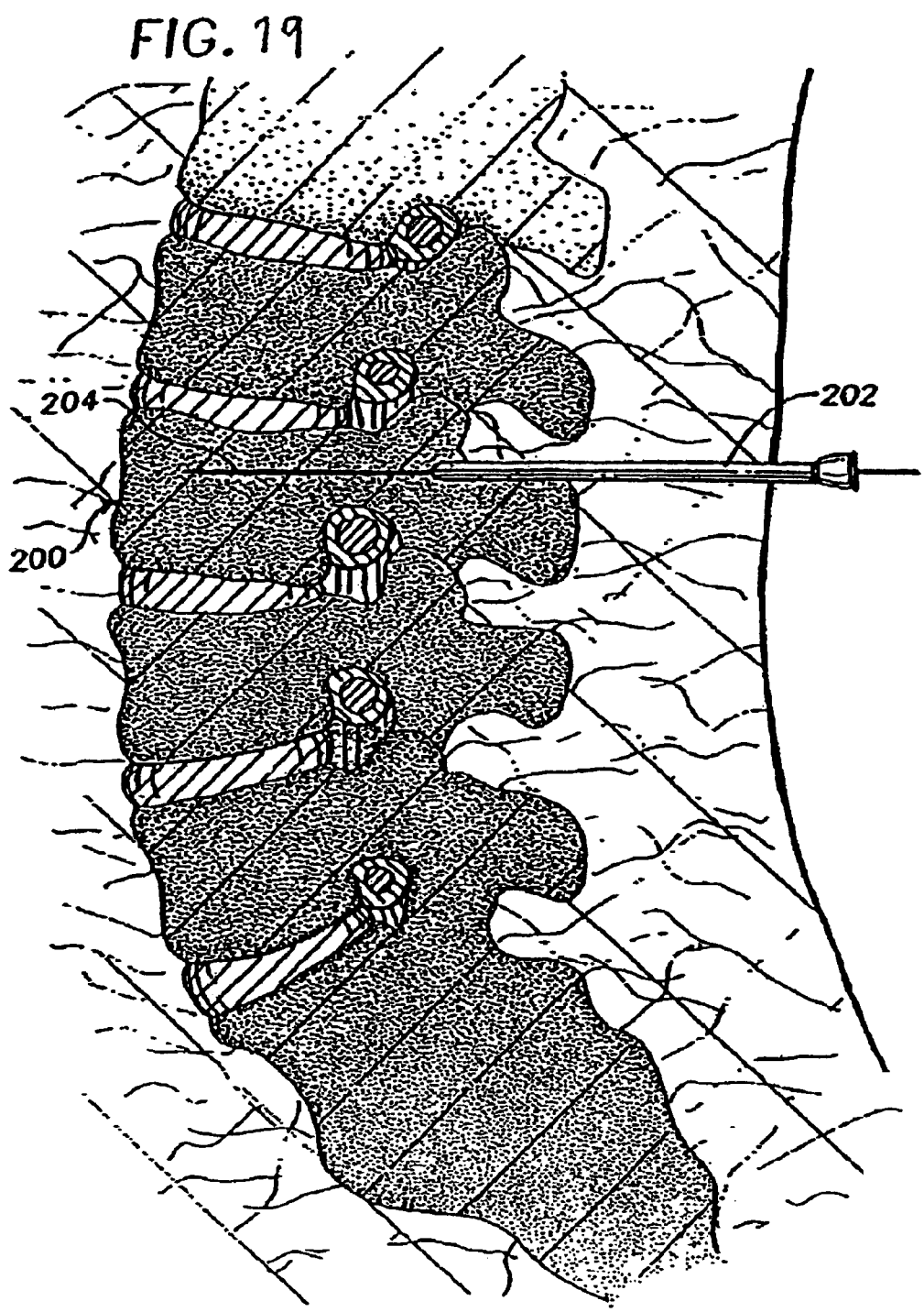

Then, as shown in FIG. 19, a rigid, needle-tipped guidewire 204 having a diameter in the range of 0.035" to about 0.060" is inserted though the biopsy needle 202 into the tract, through the periosteal incision and into the cortex of the bone, and the guidewire 204 is advanced into the anterior aspect of the vertebral body 200 or into another suitable portion of the vertebrae 200, as will be understood by those with skill in the art with reference to this disclosure. Insertion of the guidewire 204 is preferably accomplished using fluoroscopy. This process creates a continuous tract from the skin surface into the anterior vertebral body or suitable portion of the vertebrae 200.

The biopsy needle 202 is then removed and the tract from the skin surface to the nicked periosteal surface is enlarged by using a high-pressure fascial dilator balloon (not shown) over the needle-tipped guidewire. Then, the balloon is removed and a working sheath 206 is introduced into the dilated tract. Alternately, a hard plastic or metallic sheath with a central dilator is advanced over the guidewire from the skin surface to the periosteal surface. Next, a pilot hole may be drilled using an over-the-wire drill bit driven by a hand held drill.

Figure 20:
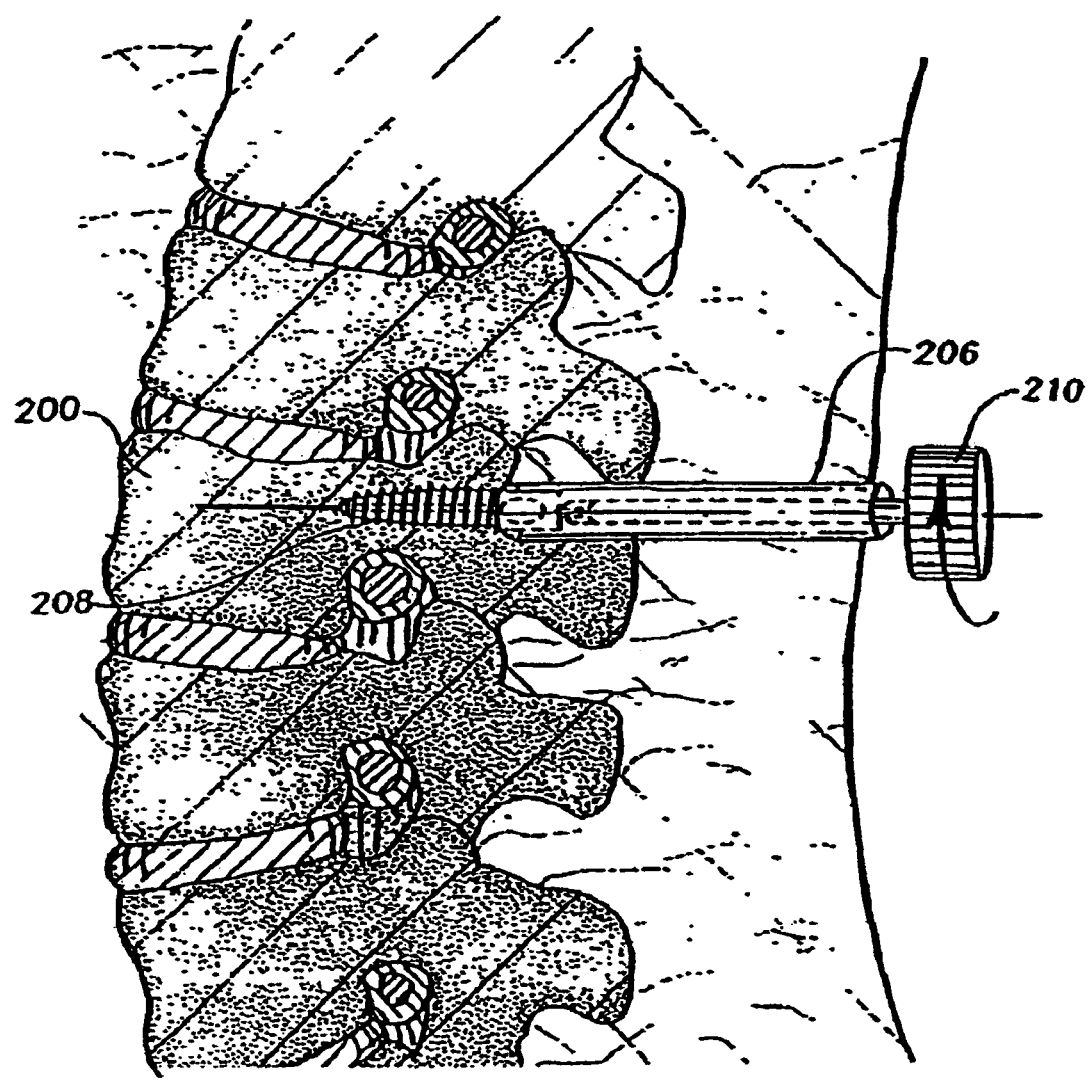
Figure 21:
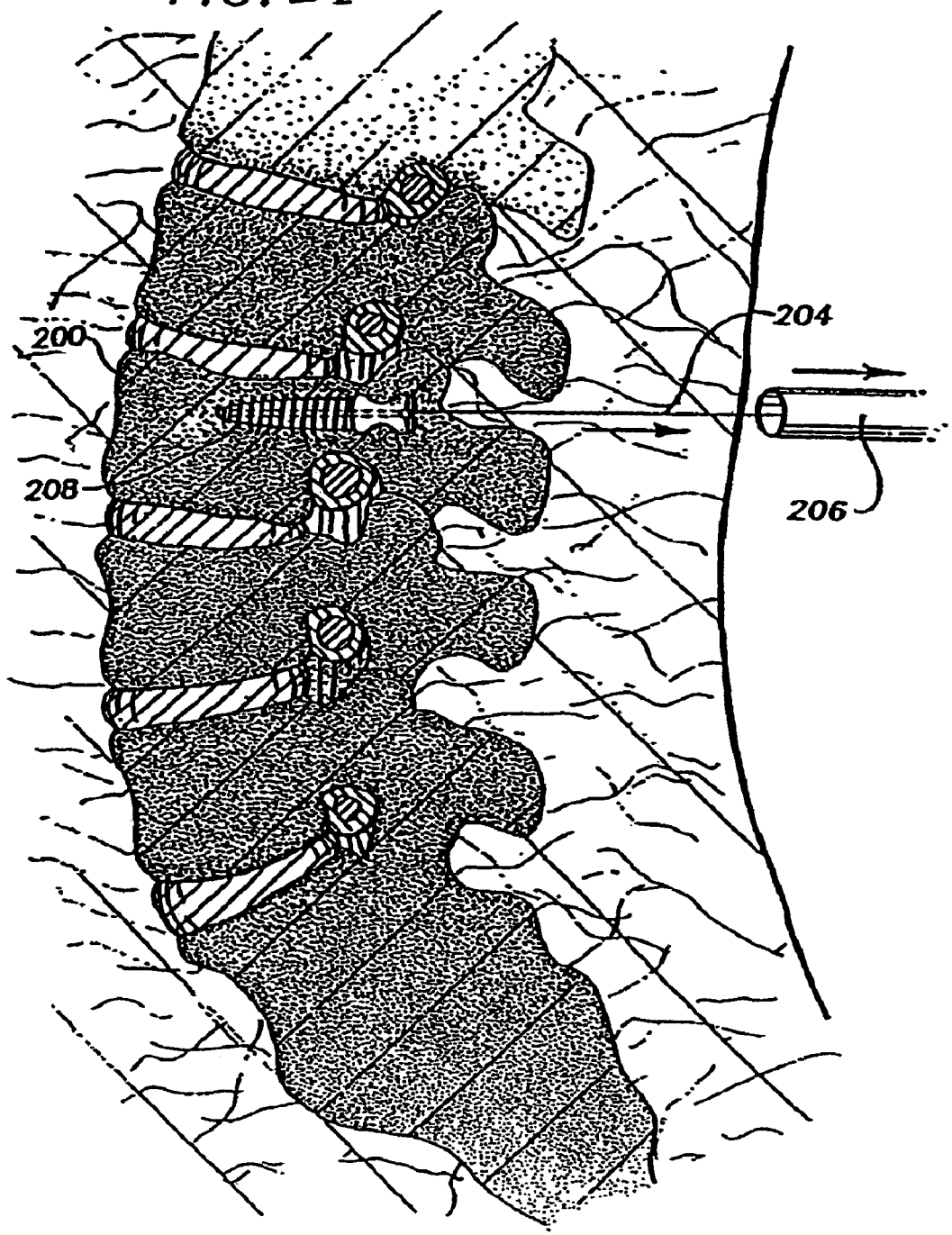

Next, as shown in FIG. 20, a bone screw 208 according to the present invention is introduced into the working sheath 206 over the guidewire 204 by introducing the central lumen of the bone screw 208 over the proximal end of the guidewire 204. A screwdriver 210 according to the present invention is similarly introduced over the guidewire 204. The bone screw 208 and distal portion of the screwdriver 210 are then advanced distally through the sheath 206 and the tract to the periosteal surface of the vertebral 200 until the proximal portion of the bone screw 208 is engaged by the tip of the screwdriver 210. Torque is applied to the bone screw 208 using the screwdriver 210 and the bone screw 208 is advanced until the distal portion of the bone screw 208 enters the anterior vertebral body or other suitable portion of the vertebra 200, while the portal of the bone screw 208 is exterior and dorsal to the vertebra 200 and the portal is open parallel to the long axis of the vertebral column. Then, as shown in FIG. 21, the guidewire 204, sheath 206 and screwdriver 210 are removed after satisfactory placement of the bone screw 208 has been obtained and confirmed by fluoroscopy. Additionally, bone matrix material such as a hydroxyapatite preparation can be injected into the central lumen of the bone screw and through the one or more than one perforation, if present, to promote bone ingrowth.

The stages discussed above are repeated for at least one additional vertebra 212 until each vertebra that is to be repositioned or fixed has a bone screw 208 applied, and additionally for at least one vertebra which is neither unstable, separated nor displaced and which lies adjacent the cranial-most or caudal-most vertebra that is being repositioned or fixed. The bone screw 208 placed into the vertebra 212 which is neither unstable, separated nor displaced is used as the anchor to reposition or fix each vertebra 200 which is unstable, separated or displaced as follows. As will be understood by those with skill in the art with reference to this disclosure, the bone screws can be placed into the vertebrae in a different order to that described above.

After a bone screw is positioned in each vertebra, the portals are connected using an inflatable connection rod according to the present invention where the rod is inserted between the portals of the bone screws and inflated to create a rigid structure with the bone screws, thereby repositioning and fixing the one or more than one previously unstable, separated or displaced vertebra, or one or more previously unstable, separated or displaced portions of one or more vertebrae with the vertebra that is neither unstable, separated nor displaced. Connection of the bone screws with the inflatable rod is accomplished as follows.

Figure 22:
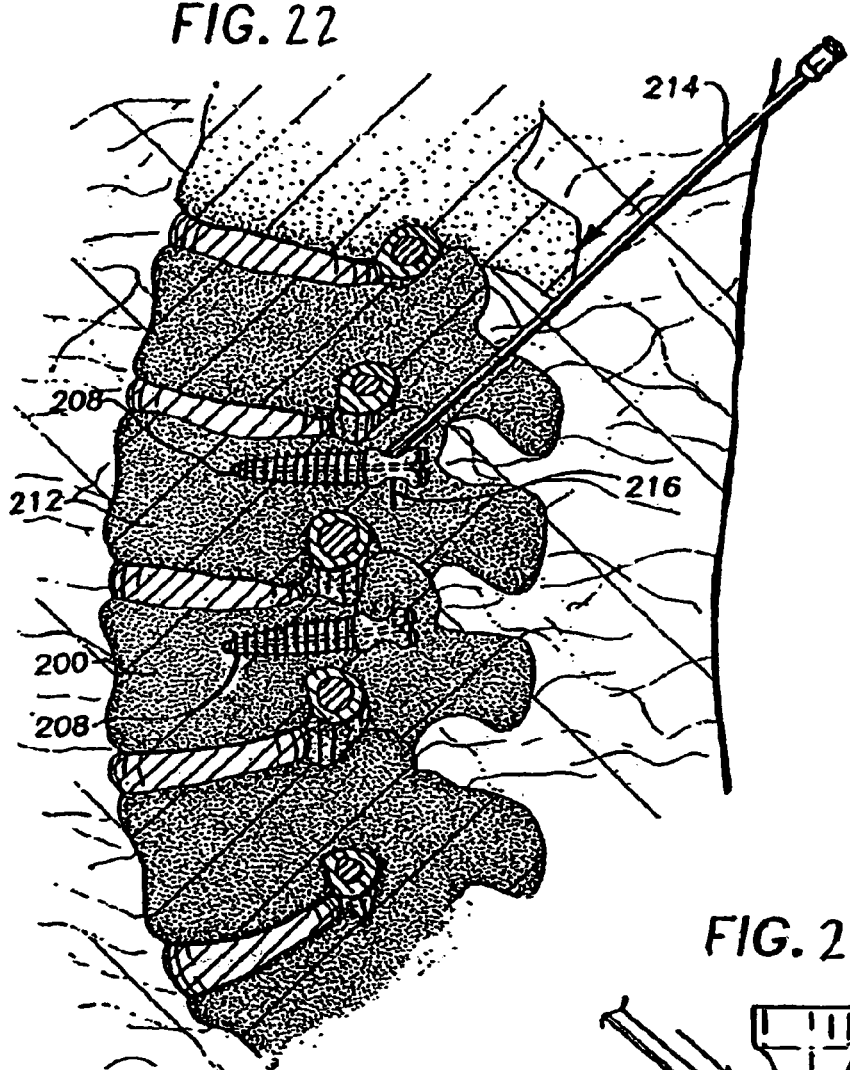
Figure 23:
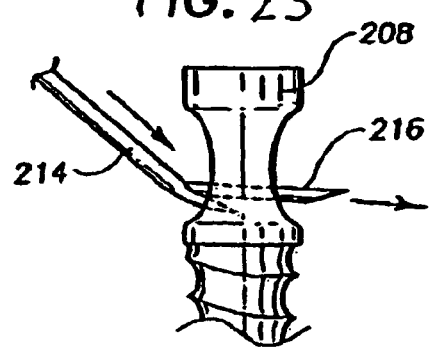

Referring now to FIG. 22 and FIG. 23, a hollow needle 214, such as a 16 gauge or 18 gauge needle, is inserted percutaneously and fluoroscopically advanced to the portal of one of the bone screws 208. While the hollow needle is shown engaging the bone screw 208 in the cranial-ward vertebrae 212, the hollow needle can engage the bone screw 208 in the caudal-ward vertebrae 200 first, as will be understood by those with skill in the art with reference to this disclosure. FIG. 23 is a detailed view of FIG. 22.

Figure 24:
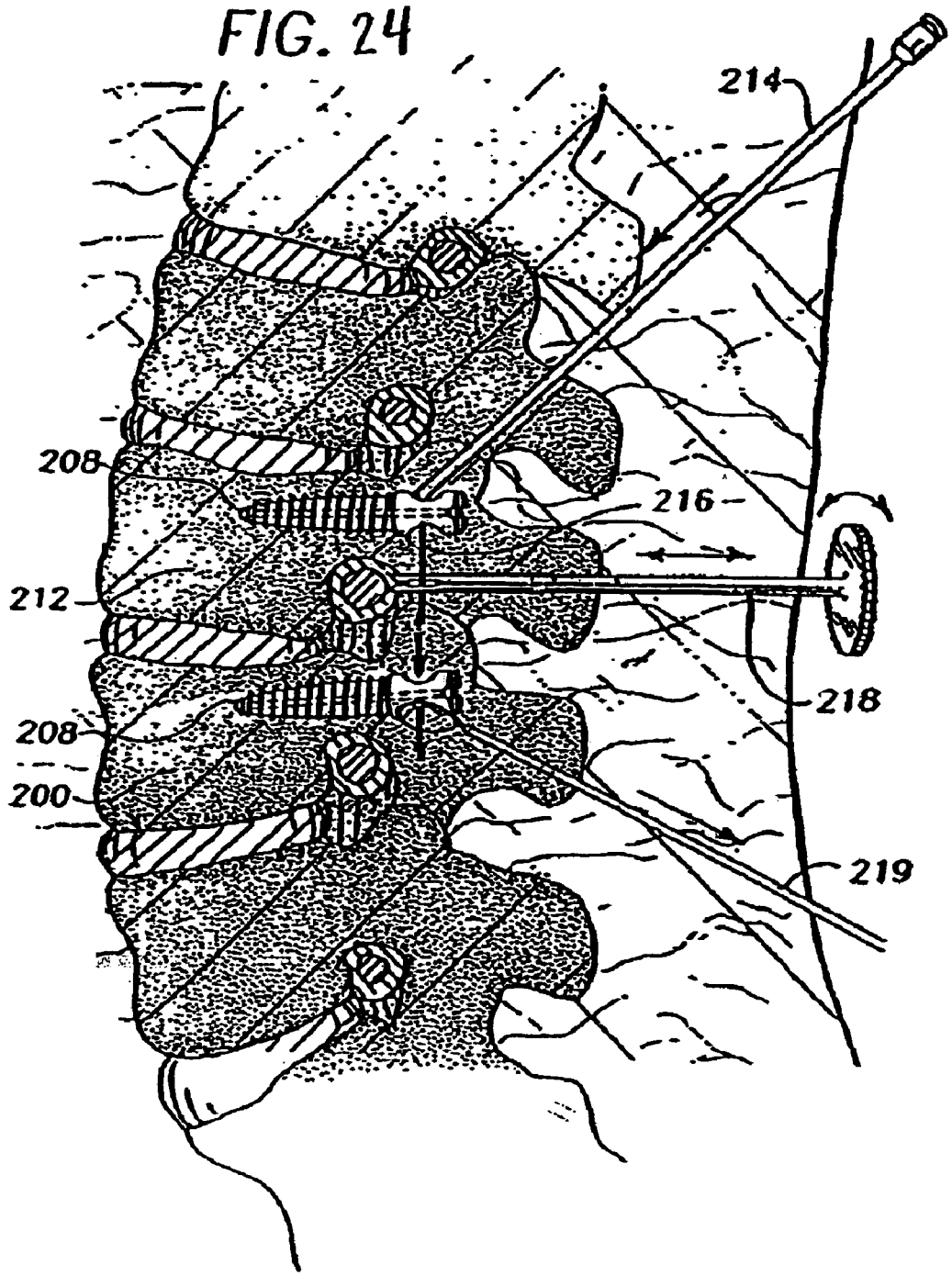

Then, as shown in FIG. 24, a needle-tipped, semi-rigid guidewire 216 is introduced through the lumen of the hollow needle 214 and into the portal of the bone screw 208 in the cranial-ward vertebrae 212. The hollow needle 214 preferably has a Tuohy needle tip which causes the guidewire 216 to exit the hollow needle 214 perpendicular to the distal-proximal axis of the bone screw 208 and parallel to the long axis of the vertebral column. Alternately, the hollow needle 214 can have an angled-tip modified Ross needle or other suitable structure as will be understood by those with skill in the art with reference to this disclosure.

In one embodiment, as further shown in FIG. 24, a guidewire directing device 218 according to the present invention is inserted percutaneously between the portals of each bone screw 208 and the fork-tipped end is used to direct the advancing guidewire 216 through the second bone screw portal, and to reorient the guidewire 216 after the guidewire 216 has passed through the portal on the bone screw 208 of the caudal-ward vertebrae 212.

In another embodiment, as further shown in FIG. 24, a guidewire capture device 219, such as a snare or grasping forceps, is inserted percutaneously, caudal to the portal of the bone screw in the caudal-ward vertebrae. The capture device 219 engages the guidewire after it passes through the portal of the bone screw in the caudal-ward vertebra and allows the distal end of the guidewire to be pulled through the skin posteriorly to obtain control of both the proximal and distal ends of the guidewire.

In another embodiment, the needle-tipped, semi-rigid guidewire 216 comprises an outer helical, flat wire sheath and an inner retractable sharp tip stylet. Once the needle-tipped, semi-rigid guidewire is placed, the stylet can be removed to allow for easier capture by the capture device with less trauma to the surrounding tissue.

Figure 25:
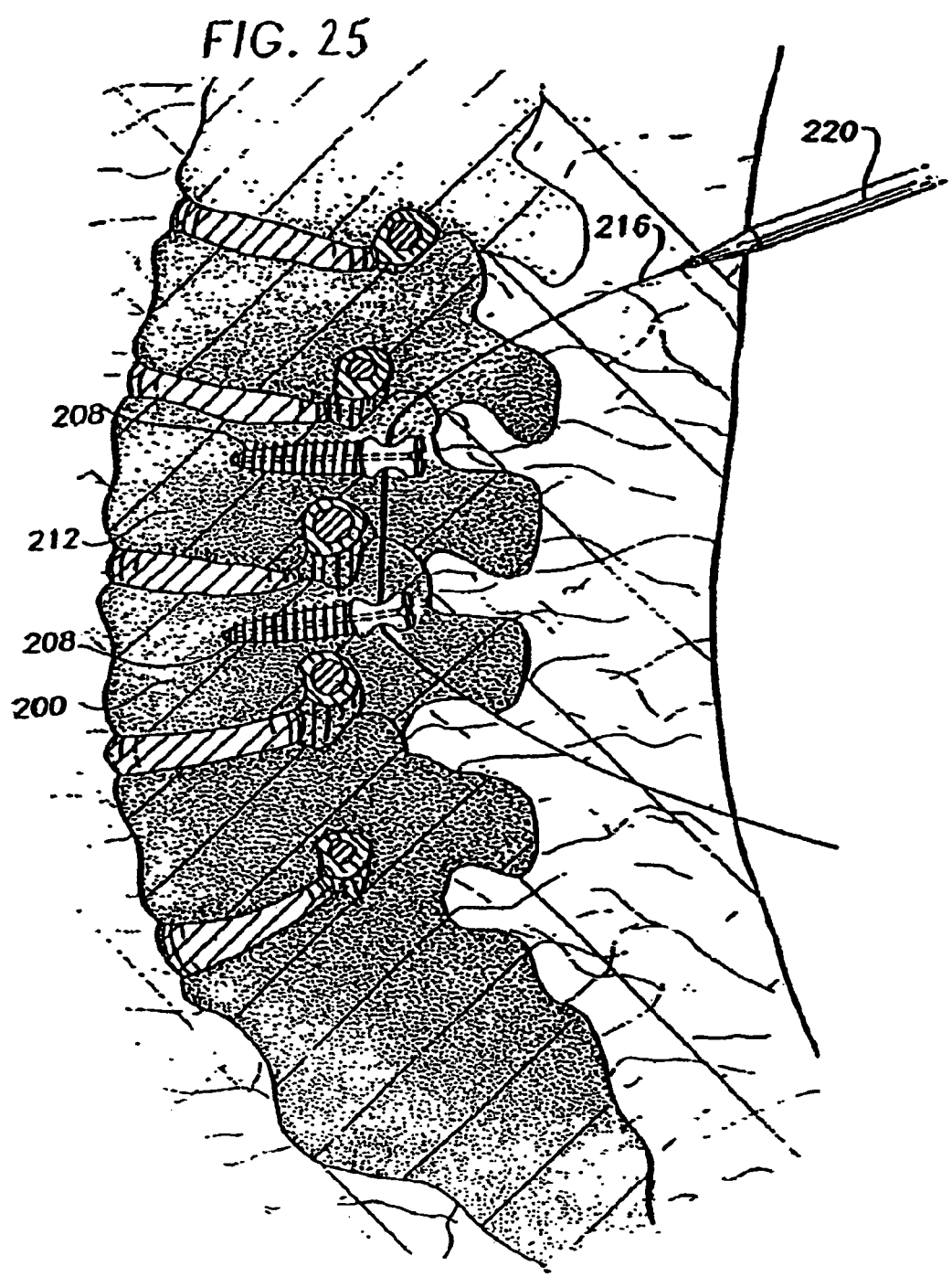

Then, as shown in FIG. 25, the entire guidewire tract is dilated using a high pressure balloon and a flexible introducer sheath 220 may be passed over the guidewire 216 along the entire guidewire tract exiting the caudal-ward stab incision. The guidewire 216 is removed after the introducer sheath 220 is placed. Alternatively, the implant is advanced over the wire 216 without the use of a sheath 220.

Figure 26:
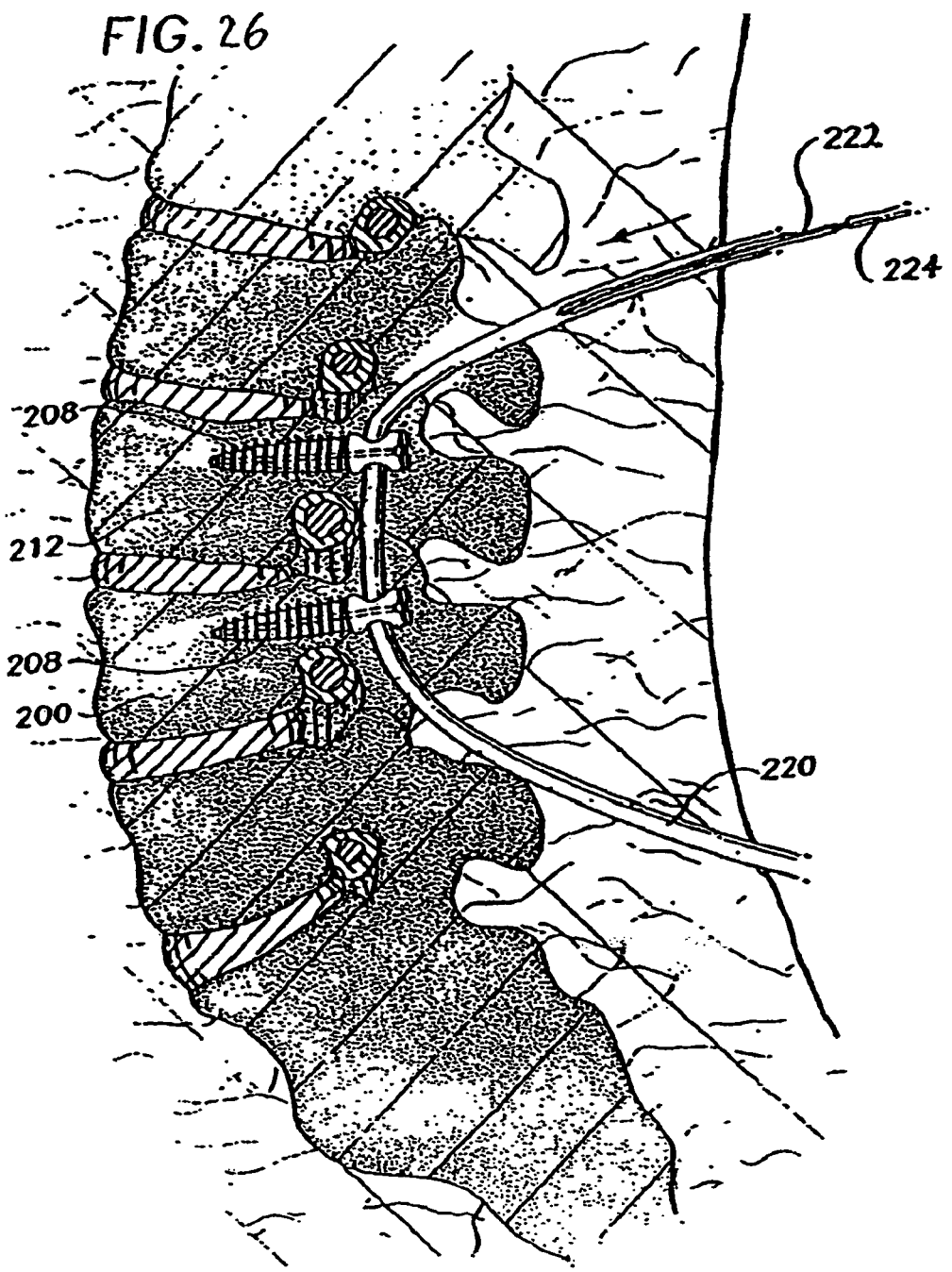

Next, as shown in FIG. 26, an uninflated, inflatable connection rod 222 according to the present invention which is attached to a proximal pushing catheter 224 is advanced through the introducer sheath 220 until the inflatable connection rod 222 advances between the two portals and the proximal end of the inflatable connection rod 222 lies cranial to the portal on the bone screw 208 in the cranial-ward vertebra 212 while the distal end of the inflatable connection rod 222 lies caudal to the portal on the bone screw 208 in the caudal-ward vertebra 200. The sheath 220 is removed and the placement is confirmed by fluoroscopy.

Figure 27:
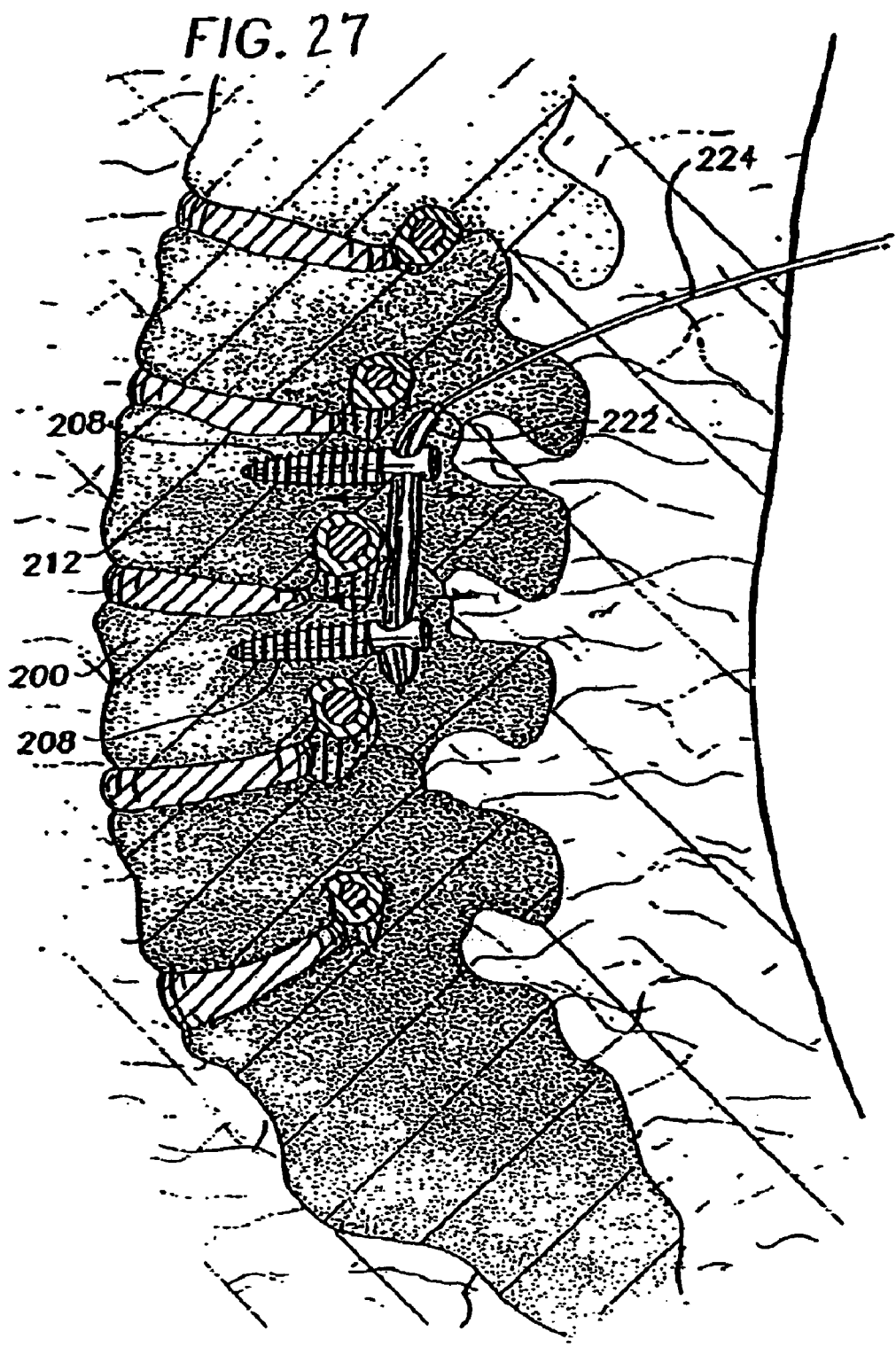

Then, as shown in FIG. 27, the balloon of the inflatable connection rod 222 is inflated with a rapid setting, curable media such as liquid polymer, or its equivalent, and the polymer is allowed to set fixing each bone screw 208 in relation to each other and repositioning and fixing the vertebra 200 or portion of the vertebra that was unstable, separated or displaced. In one embodiment, the liquid polymer is or includes a two part epoxy or other hardenable media such as those discussed elsewhere herein, and curing is optionally accelerated by the application of heat. The inflated balloon of the inflatable connection rod 222 expands radially beyond the diameter of the portals of each bone screw 208 which helps fix the bone screws 208 in relation to each other.

Figure 28:
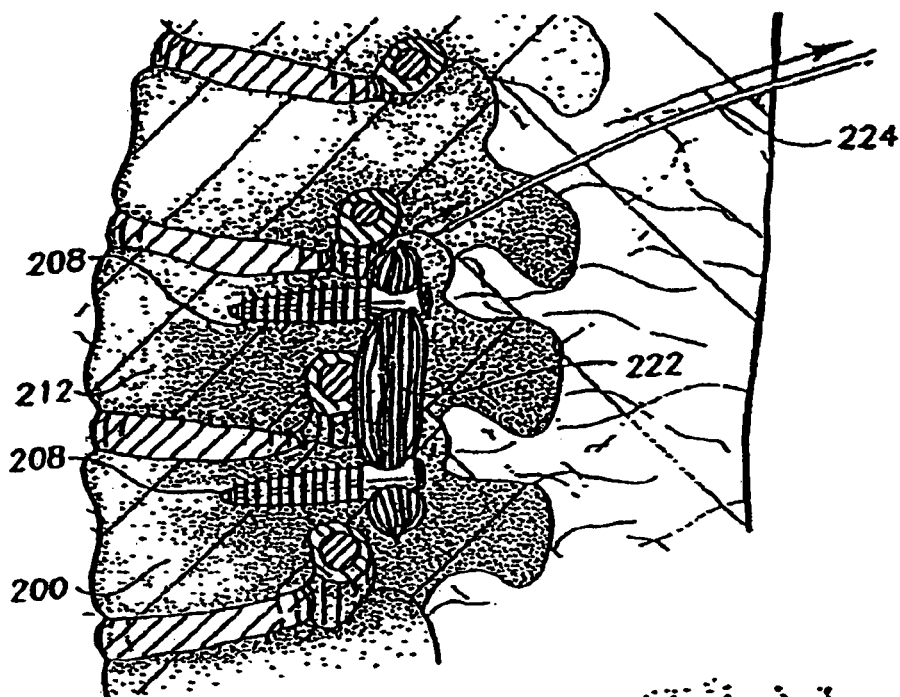

Finally, as shown in FIG. 28, the delivery or pushing catheter 224 is detached from the inflatable connection rod 222 by pulling on the pushing catheter 224 while resisting proximal movement of the inflatable connection rod 222 to disengage the inflatable connection rod 222 from the pushing catheter 224 and the pushing catheter 224 is removed. The inflatable connection rod 222 comprises a self-sealing valve which prevents the polymer from leaking once the pushing catheter is detached. The vertebra is then fixed unilaterally. The method can be repeated on the opposite side of the spinous processes of the patient's vertebrae column, thereby repositioning or fixing the one or more unstable, separated or displaced vertebrae or the one or more portions of one or more vertebrae bilaterally. The access incisions are closed or sealed as necessary and routine postoperative care administered.

Figure 29:
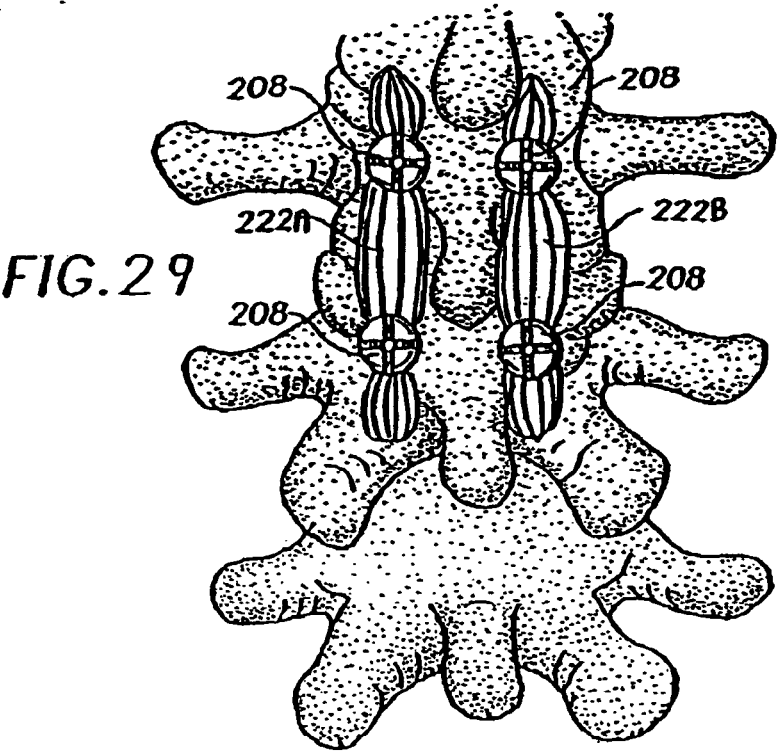
FIG. 29 is a posterior elevational view of a portion of a vertebral column post-procedure, with two fixation devices mounted thereon.

Referring now to FIG. 29, there is shown a posterior perspective view of a portion of a vertebral column which has had some vertebrae repositioned and fixed bilaterally according to the present invention. When bilateral fixation is accomplished, it is preferred to place all bone screws before connecting the portals with inflatable connection rods.

Figure 30:
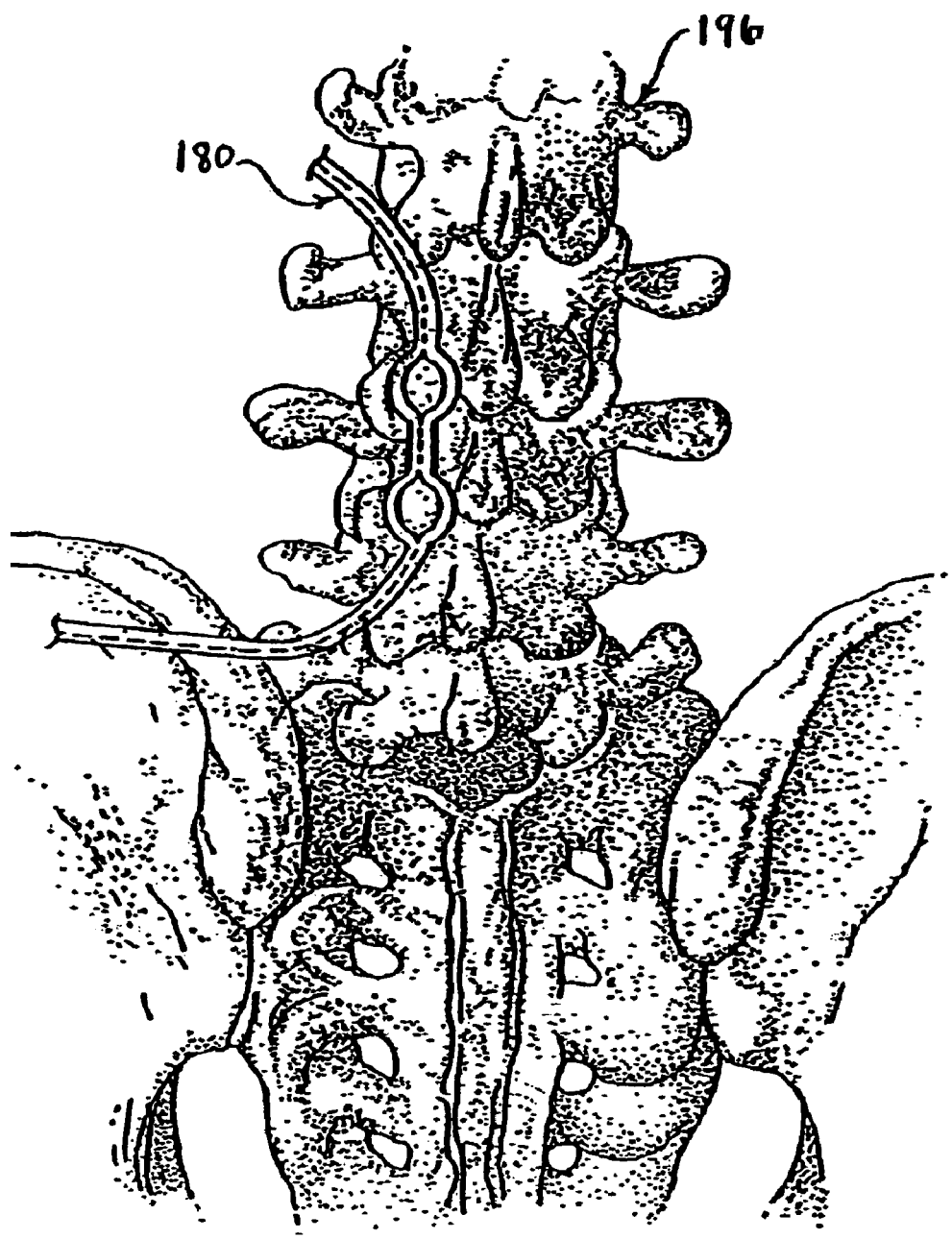
FIGS. 30-32 are posterior elevational views of a portion of a vertebral column showing a method of the present invention using a directing sheath.
Figure 31:
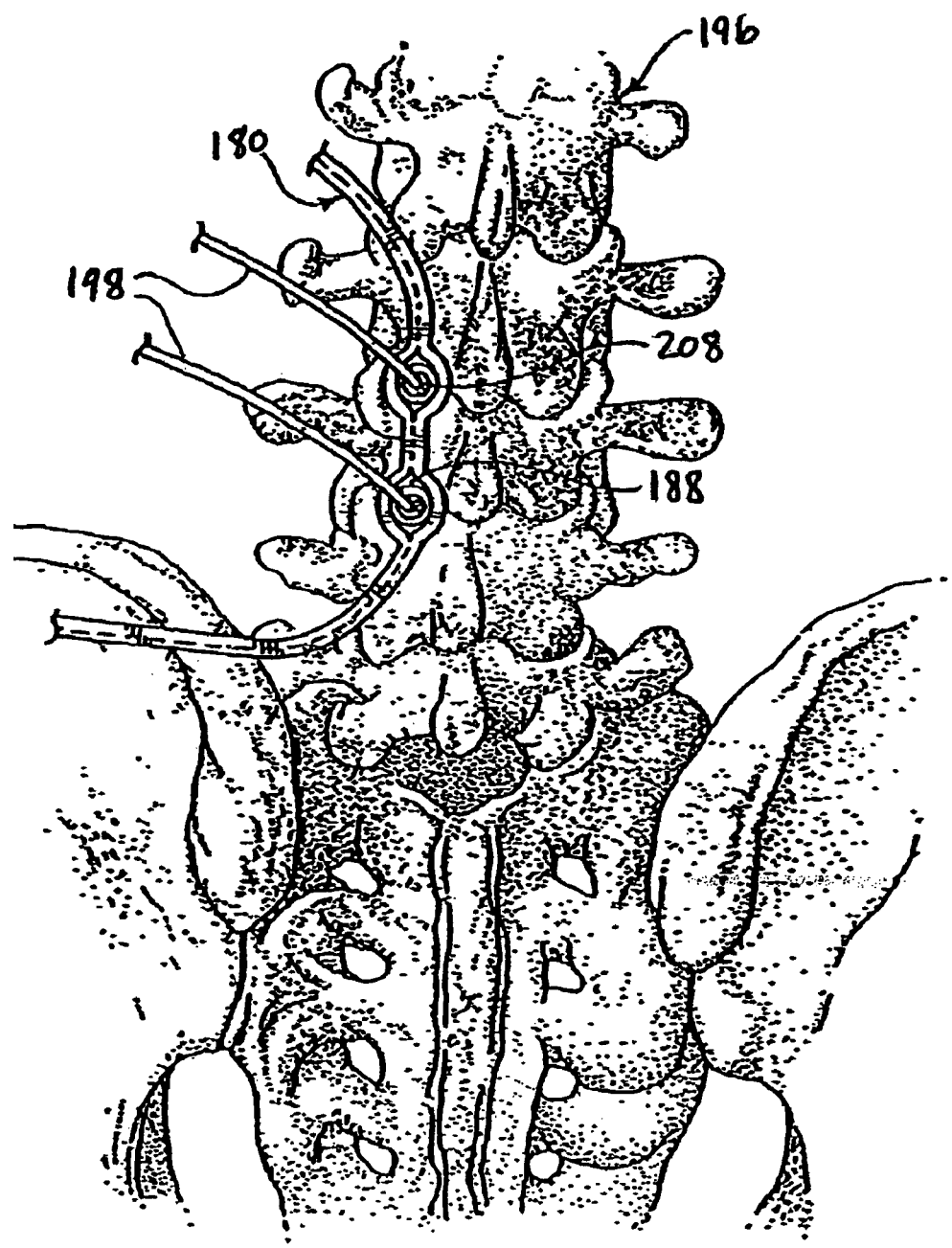
Figure 32:
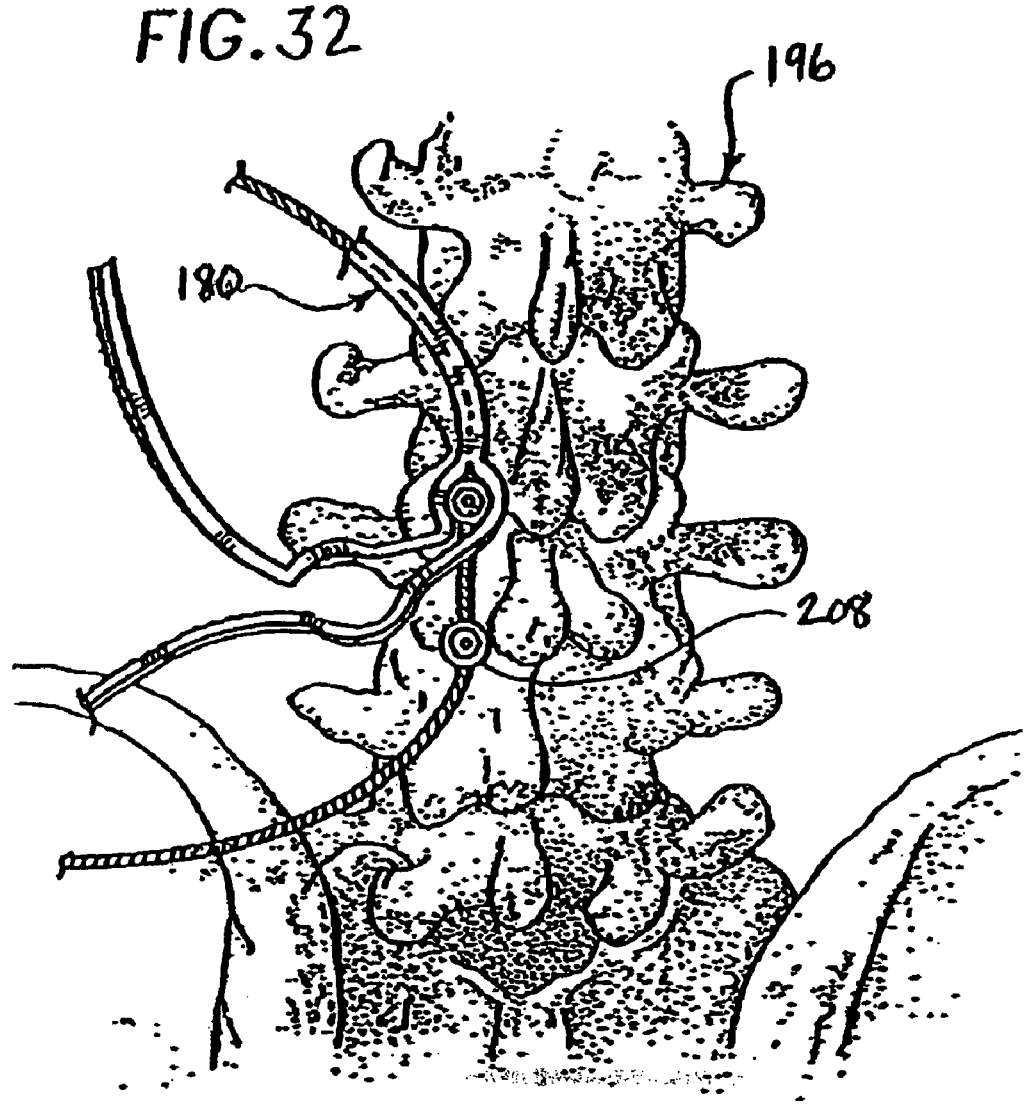

In another embodiment of the present method, a directing sheath 180 according to the present invention is advanced over a guidewire until the openings in the directing sheath 180 overlie the position in each vertebra which will receive a bone screw 208. The bone screws 208 are then placed as disclosed in this disclosure, but through the openings in the directing sheath 180, which aligns the lumen in the directing sheath with the portals of the bone screw 208. Then (not shown), a guidewire is inserted into the lumen of the directing sheath at the proximal end of the directing sheath and advanced until the guidewire passes through each portal of the bone screws and exits the body through the lumen of the directing sheath at the distal end. The directing sheath is then removed by peeling the sheath apart along the scored lines and pulling the two halves out from the body. The guidewire that was in the lumen of the directing sheath remains in place to guide the placement of the uninflated, inflatable connection rod. Alternately, the uninflated, connection rod can be inserted directly into the lumen of the directing sheath at the proximal end and advanced until the uninflated, inflatable connection rod is properly positioned between the portals of the bone screws. Referring now to FIG. 30 through 32, there are shown posterior perspective views of a portion of a vertebral column undergoing the method of the present invention using a directing sheath according to the present invention, showing the bone screws placed through the openings of the directing sheath. As can be seen in FIG. 30, the directing sheath 180 is positioned adjacent the vertebral column 196 according to the present invention. Next as can be seen in FIG. 31, guidewires 198 are used to place bone screws 208 through openings 188 in the directing sheath 180. Finally, as can be seem in FIG. 32, the directing sheath 180 is removed by the directing sheath 180 into two separate halves.

In one embodiment, there is provided a kit for performing methods of the present invention. The kit comprises a plurality of bone screws according to the present invention. The kit can also comprise other components of the system of the present invention, such as a guidewire directing device, an inflatable connection rod, the curable medium to be injected and a directing sheath. The curable medium may comprise one part or it may comprise two or more parts that are mixed before, during or after injection. In another preferred embodiment, the kit also comprises a screwdriver according to the present invention. A control with electronic driving circuitry can also be provided, for thermal acceleration of the hardenable media.

Referring to FIG. 29, a first inflatable connection rod 222a and a second inflatable connection rod 222b are illustrated as extending generally in parallel with each other, and also generally in parallel to the longitudinal axis of the spine. Deviations from this illustrated parallel relationship may also occur, in either or both of the lateral plane as well as the anterior/posterior plane. Such deviations from parallel may be a consequence of anatomical variations, or procedural choices or irregularities as will be appreciated by those of skill in the art. In any of these configurations, additional stability may be achieved by cross-linking the first inflatable connection rod 222a with the second inflatable connection rod 222b. Thus, in accordance with a further aspect of the present invention, there is provided a method and apparatus for cross-linking two or more inflatable connection rods.

Cross-linking may be accomplished in any of a variety of configurations, as will be apparent to those of skill in the art in view of the disclosure herein. For example, a pair of laterally opposing pedicle screws 208 may be connected to each other by an inflatable crossbar or solid crossbar as will be apparent from the disclosure herein. Alternatively, the body of the two opposing inflatable connection rods 222a and 222b can also be connected by a crossbar. Although the present discussion will focus primarily upon the latter construction, it is to be understood that the present invention contemplates any cross connection between a left and right connection rod, preferably through a procedure in which each of the connection rods or crossbars is installed in a less invasive or minimally invasive procedure.

Figure 33:
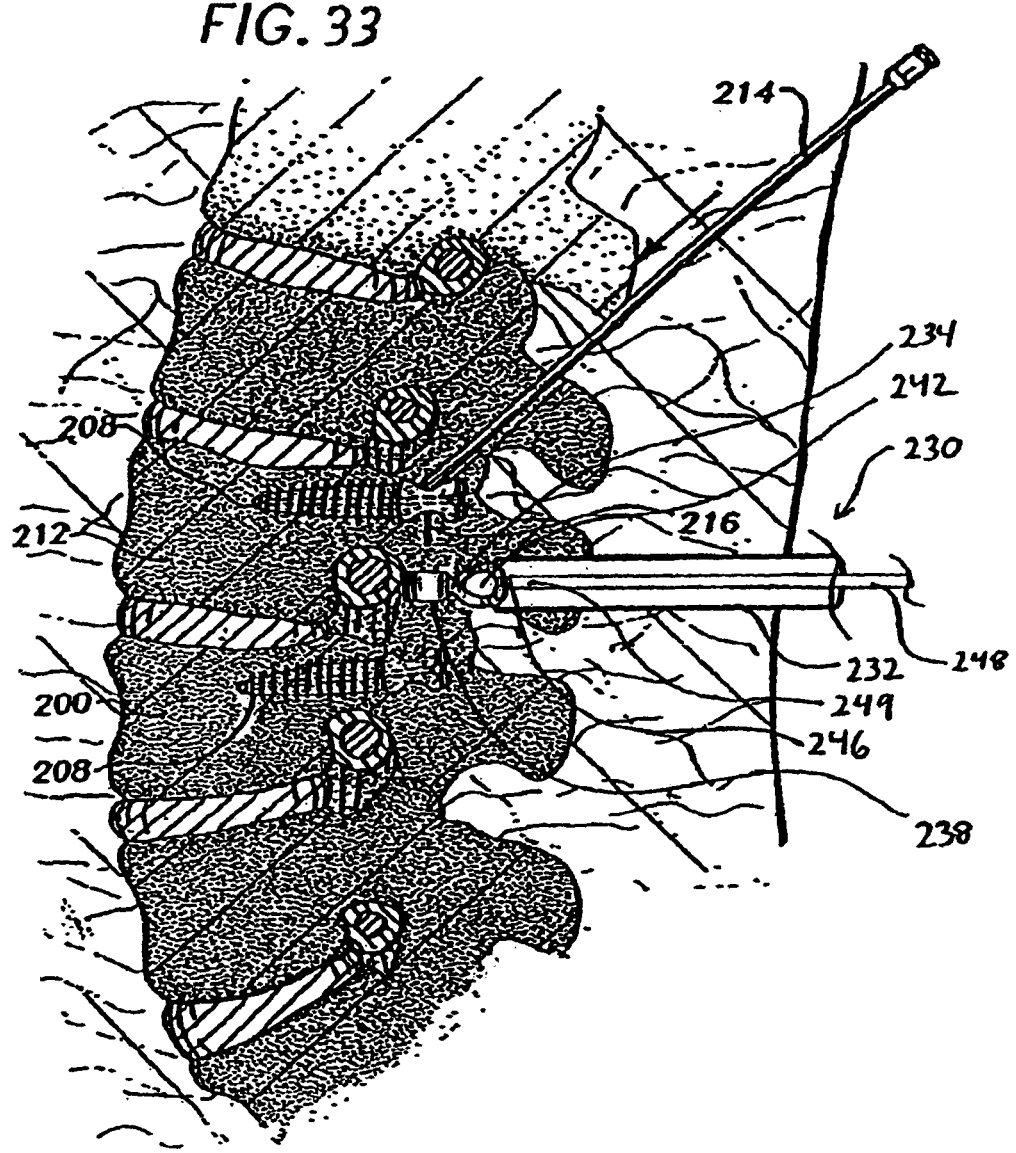
FIG. 33 is a side elevational view of a cross tie held in position by a cross tie deployment system, in-between a first and a second pedicle screw.

Referring to FIG. 33, a side elevational view of a portion of the spine is illustrated. A first and second pedicle screws 208 have been positioned in accordance with procedures discussed previously herein. A hollow needle 214 is illustrated, for guiding a "rocketwire" or guidewire 216 through the coaxial apertures in the first and second pedicle screws 208.

FIG. 33 additionally illustrates a cross tie deployment system 230, partway through a deployment procedure. The cross tie deployment system 230 comprises an access sheath 232. Access sheath 232 comprises an elongate tubular body having a proximal end and a distal end, and a central lumen extending therethrough. In general, the central lumen will have a diameter within the range of from about 24 French to about 30 French, although other diameters may be utilized depending upon the size of the device to be deployed. The access sheath 232 is positioned through tissue along an axis which intersects the path of the guidewire 216, as is advanced from a first pedicle screw 208 through an aperture in a second pedicle screw 208, as illustrated.

A cross tie support 248 is axially movably positioned within the access sheath 232. Cross tie support 248 is connected at a distal end 249 through a releasable connector 246 to a cross tie 234. Cross tie 234 facilitates connection of a crossbar with a primary inflatable connection rod, to achieve cross linking of the orthopedic fixation system.

Although a variety of structures for cross tie 234 can be utilized, one convenient construction is illustrated in FIG. 37. In general, the cross tie 234 includes a first connector 236 such as a first aperture 238 for receiving an inflatable connection rod 222 as has been discussed previously herein. In one implementation, the aperture 238 has an inside diameter of approximately 6 mm. However, diameters of the first aperture 238 may be varied widely, depending upon the diameter of the inflatable connection rod 222, and the desired physical performance characteristics.

Figure 35:
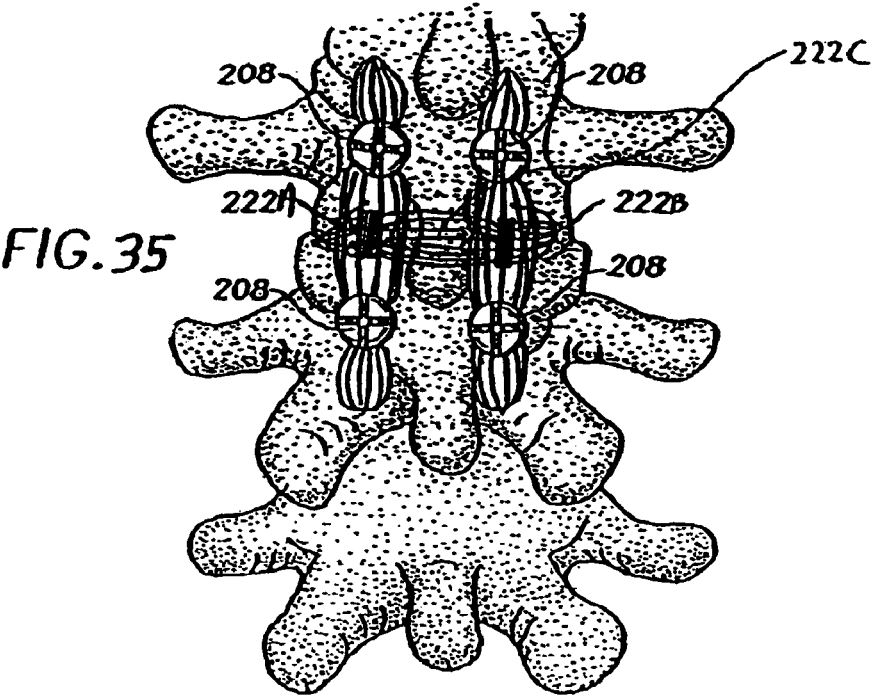
FIG. 35 is a posterior elevational view of a portion of a vertebral column, post procedure, with two inflatable connection rods and one crossbar mounted thereon.

The cross tie 234 additionally comprises a second connector 240, such as a second aperture 242. The second aperture 242 is adapted to receive a crossbar 222c, as illustrated in FIGS. 35 and 36. In the illustrated cross tie 234, a longitudinal axis extending through the first aperture 238 is generally perpendicular to a longitudinal axis extending through a second aperture 242, and offset by a spacing distance which will determine the anterior-posterior spacing between the axis of an inflatable connection rod 222a and a corresponding crossbar 222c. In one embodiment, the overall as mounted anterior-posterior length of the cross tie 234 is approximately 16 mm, and the width of the cross tie 234 is no more than about 8 mm.

The cross tie 234 is held in place during the procedure by a cross tie support 248 through a releasable connector 246. The releasable connector 246 facilitates the positioning of the cross tie 234 during the deployment step, but enables decoupling following proper positioning of at least an inflatable connection rod 222a and possibly also the crossbar 222c. Any of a variety of releasable connection structures may be utilized, such as a threaded distal end on the cross tie support 248, which threadably engages an aperture on the cross tie 234.

As illustrated in FIGS. 33, 36 and 37, the cross tie 234 is held in position by the cross tie support 248 such that the longitudinal axis extending through the first aperture 238 is collinear with the path of the guidewire 216. The longitudinal axis of the second aperture 242 extends transversely such that it aligns with a second aperture 242 in a second cross tie 234 to accomplish the cross-linked construction illustrated in FIGS. 35 and 36.

Figure 34:
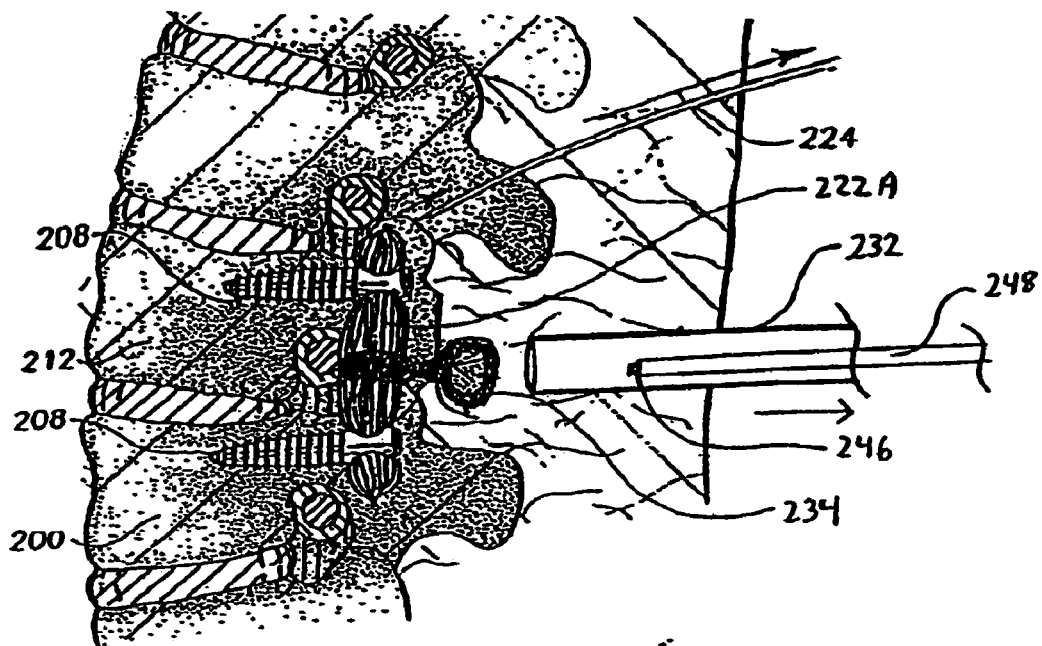
FIG. 34 is a side elevational view as in FIG. 33, illustrating an inflatable connection rod inflated between the first and second pedicle screws, with a cross tie mounted thereon.

Referring to FIG. 34, the first inflatable connection rod 222a is illustrated as inflated after having been positioned through the first aperture 238 on the cross tie 234, as well as through the approximately collinear apertures on a pair of bone screws 208. This is accomplished by advancing the guidewire 216 through the first bone screw, then the first aperture 238 and then the second bone screw 208, as illustrated in progress in FIG. 33. The connection rod 222a may then be advanced over the wire and inflated following the inflatable connection rod implantation procedures discussed previously herein.

Preferably, the first aperture 238 is dimensioned with respect to the connection rod 222a such that a secure fit is provided between the inflatable connection rod 222a and cross tie 234 following complete curing of the curable media. If shrinkage of the curable media is contemplated, the first aperture 238 may be defined within an annular ring on the frame 244 which has an expansion break extending therethrough. In this manner, inflation of the inflatable connection rod 222a can be accomplished such that the expansion break allows a slight enlargement of the diameter of the first aperture 238. Upon transverse shrinkage of the inflatable connection rod 222a during the curing process, the natural bias imparted by the frame 244 allows the first aperture 238 to shrink, thereby retaining a tight fit with the inflatable connection rod 222a throughout a range of diameters. This construction may also be applied to the apertures extending through the bone screws 208, as well as the second apertures 242.

The cross tie support 248 is illustrated in FIG. 34 as detached from the cross tie 234, such as by unscrewing the releasable connector 246. This may be accomplished before or after positioning of the crossbar 222c, depending upon the clinical judgment of the practitioner.

The final construction is illustrated in FIG. 35. As seen therein, a crossbar 222c extends between a first cross tie 234 carried by the first inflatable connection rod 222a and a second cross tie 234 carried by the second inflatable connection rod 222b. The crossbar 222c may be positioned through the pair of opposing apertures 242 using the same techniques discussed and illustrated previously herein for the implantation of the inflatable connection rods 222. The initial position of a curved needle and guidewire for positioning the crossbar 222c is schematically illustrated in FIG. 36.

Although only a single crossbar 222c is illustrated, two or three or four or more crossbars 222c may alternatively be used, depending upon the axial lengths of the inflatable connection rods 222a and 222b, and the desired structural integrity of the finished assembly. In addition, although the crossbar 222c is illustrated as extending generally perpendicular to the longitudinal axis of each of the inflatable connection rods 222a and 222b, the crossbar 222c may cross each of the inflatable connection rods 222 at any of a variety of angles ranging from approximately +45° to −45° with respect to the illustrated position. Thus, the crossbar 222c may be implanted at a diagonal if the desired structural integrity can be thus achieved.

The crossbar 222c may comprise any of a variety of forms. For example, the crossbar illustrated in FIG. 35 may be identical in construction to any of the inflatable connection rods discussed previously herein.

In an alternate application of the cross-linking technology of the present invention, the crossbar is constructed in a manner which enables elimination of the separate cross tie 234. Referring to FIGS. 40-43, the crossbar comprises a first portal 250, for receiving a first inflatable connection rod 222a, and a second portal 252 for receiving a second inflatable connection rod 222b. First portal 250 and second portal 252 are spaced apart by an elongate tubular body 254. Body 254 may be a solid element, such as a polymeric extrusion, molded part or metal rod. Alternatively, body 254 comprises a tubular sleeve, such as illustrated in FIGS. 40-42. In the illustrated embodiment, the tubular sleeve is provided with a plurality of circumferentially extending slots 254, to permit flexibility of the crossbar 222c during deployment. Slots 254 may be formed such as by laser cutting a stainless steel, nickel-titanium alloy or other tube.

FIG. 41 schematically illustrates the distal end of a deployment system 258 for deploying the crossbar 222c of FIG. 40. The tubular body 254 is carried by a dilator 260 which extends axially therethrough. In one application, the dilator 260 is approximately 21 French, for accommodating a tubular body 254 having an inside diameter of about 7 mm and an outside diameter of about 8 mm.

The 21 French dilator 260 is advanced over a stiff 0.038" guidewire, with an 8 French catheter. A 24 French pusher sheath 262 is positioned proximally of the tubular body 254.

Using this deployment system, the tubular body 254 may be positioned relative to two pairs of bone screws 208 as illustrated schematically in FIG. 42. A first pair of bone screws 208a and 208b contain apertures which coaxially align with the first portal 250. A second pair of bone screws 208c and 208d carry apertures which are coaxially aligned with a second portal 252. Once positioned as illustrated in FIG. 242, a guiding assembly such as a curved needle 214 and a rocket wire 216 may be advanced as illustrated in FIG. 42. An inflatable connection rod 222a may thereafter be advanced along the wire, and inflated to secure the first and second bone screws 208a and 208b, and also the crossbar 222c. A similar procedure may be accomplished to install a second inflatable connection rod 222b.

The tubular body 254 may by itself provide sufficient cross-linking strength for the intended purpose. Alternatively, the tubular body 254 may be filled with a curable media 266 to enhance the structural integrity of the resulting assembly. For example, as illustrated in FIG. 43, the deployment system 258 may additionally comprise an inflatable container such as an inflatable connection rod previously disclosed herein, in communication with a source of curable media through an inflation lumen. Depending upon the construction of the inflatable container, it may be filled with a hardenable media 266 either prior to or following positioning of the first inflatable connection rod 222a and second inflatable rod 222b as discussed previously herein.

Figure 38:
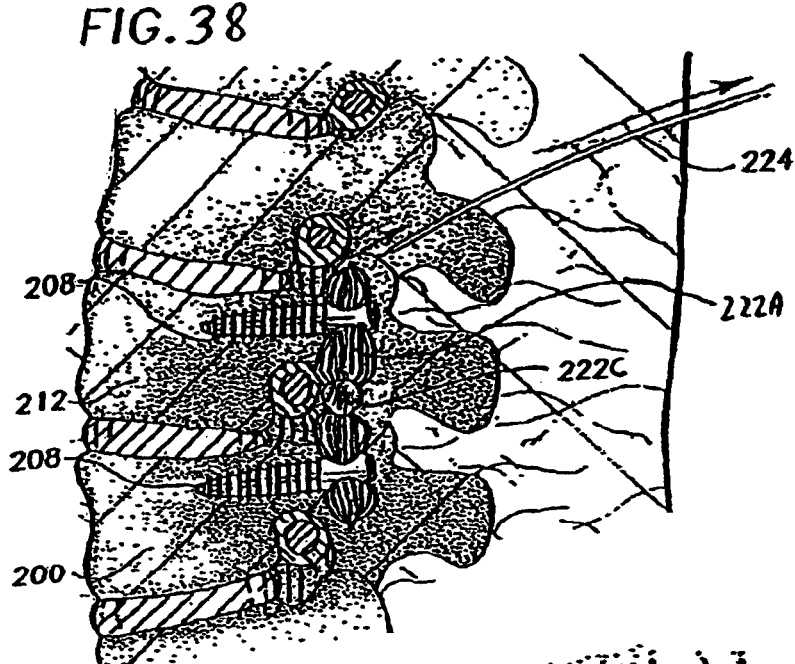
FIG. 38 is a side elevational view of a portion of a spine, having an alternate crossbar connected to an inflatable connection rod.
Figure 39:
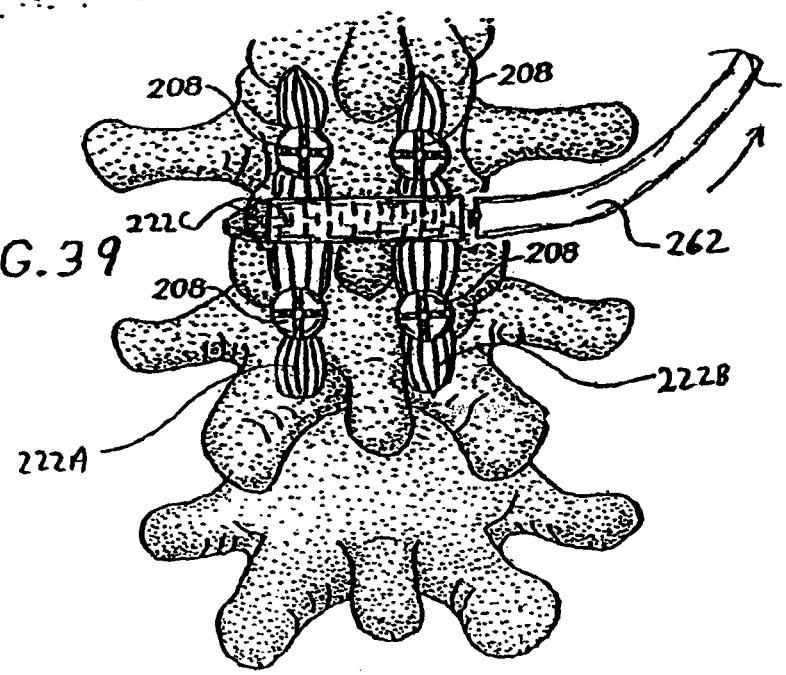
FIG. 39 is a posterior elevational view of a portion of a vertebral column, showing the crossbar of FIG. 38.

The embodiment of FIGS. 40-43 is illustrated in position within the patient, in FIGS. 38 and 39. As can be seen from FIGS. 38 and 39, the crossbar 222c resides within the plane that extends through the apertures in the bone screws 208. Thus, the crossbar 222c in the configuration illustrated in FIGS. 38 and 39 is lower profile, or positioned anteriorly of the crossbar 222c in the embodiment of FIGS. 34 and 35. The location of the crossbar 222c in FIGS. 38 and 39 is not, however, precisely to scale or in the exact or only implantable location in the spine. For example, the crossbar 222c may extend laterally through a space in-between an adjacent pair of caudal and cephalad spinous processes. If the crossbar 222c is preferably positioned at a more caudal or cephalad position than the opening between adjacent spinous processes, or if the crossbar 222c is preferably positioned farther anteriorly than would be permitted by the transverse process or other bony structure, the crossbar 222c may extend through an aperture bored through the bone, or portions of the bone may be removed. Any of a variety of bores or drills may be utilized to bore a transverse aperture, such as through a spinous process. The crossbar 222c may thereafter be advanced through the bore and locked into place using the first and second support structure 222a and 222b as is disclosed elsewhere herein.

The various materials, methods and techniques described above provide a number of ways to carry out the invention. Of course, it is to be understood that not necessarily all objectives or advantages described may be achieved in accordance with any particular embodiment described herein. Thus, for example, those skilled in the art will recognize that the materials such as media may be made and the methods may be performed in a manner that achieves or optimizes one advantage or group of advantages as taught herein without necessarily achieving other objectives or advantages as may be taught or suggested herein.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A formed in place implantable orthopedic device, comprising:
   an elongated implantable device sized and shaped to extend between a first vertebra and a second vertebra, the elongated implantable device having an outer wall defining a cavity therein; and
   a hardenable media within the cavity to form the orthopedic device, said hardenable media comprising a resin and hardener mixture that is substantially cured at a temperature below 45° C. in 90 minutes or less;
   wherein the hardenable media is hardened while the implantable device is positioned within the body of a patient to create the formed in place orthopedic device, the formed in place orthopedic device having a static compression bending value for supporting spinal loads and fixing the first vertebra relative to the second vertebra.

2. The formed in place orthopedic device of claim 1, wherein said hardenable media comprises an epoxy resin.

3. The formed in place orthopedic device of claim 2, wherein said epoxy resin comprises a total of about 65-75% by weight of one or more diepoxide resins and a total of about 25-35% by weight of one or more amine curing agents.

4. The formed in place orthopedic device of claim 2, wherein said epoxy resin comprises about 45-52% by weight aromatic diepoxide resin, about 19-23% by weight aliphatic diepoxide resin, about 20-29% by weight dialkylamines and about 4-9% cycloalkylamines.

5. The formed in place orthopedic device of claim 4, wherein the aromatic diepoxide resin comprises diglycidyl ether of Bisphenol A or diglycidyl ether of Bisphenol F.

6. The formed in place orthopedic device of claim 4, wherein the aliphatic diepoxide resin comprises one or more alkane diols of glycidyl ether.

7. The formed in place orthopedic device of claim 4, wherein the dialkylamines are according to the formula H2N—R—NH2, wherein R is a branched or unbranched C2-C10 alkyl group.

8. The formed in place orthopedic device of claim 4, wherein the cycloalkylamines are N-aminoalkylpiperazines.

9. The formed in place orthopedic device of claim 4, wherein the aromatic diepoxide resin comprises diglycidyl ether of Bisphenol A, the aliphatic diepoxide resin comprises butane diol of glycidyl ether, the dialkylamine comprises 1,3-diaminopropane, and the cycloalkylamine comprises N-aminoethylpiperazine.

10. The formed in place orthopedic device of claim 1, wherein said hardenable media cures to a hardened form having a static compression bending value (ASTM F1717) of at least 100 lbs.

11. The formed in place orthopedic device of claim 1, wherein the elongated implantable device is inflatable between a first insertion configuration having a first diameter and a second fixation configuration having a second diameter, the second diameter being greater than the first diameter.

12. The formed in place orthopedic device of claim 11, further comprising a first bone anchor having a first portal sized to receive at least a portion of the elongated implantable device, wherein the at least a portion of the elongated implantable device is able to pass through the first portal in the first insertion configuration and is secured to the first portal in the second fixation configuration.

13. A method of forming an orthopedic device at a treatment site within the body of a patient, comprising the steps of:
  positioning an implantable device having an outer wall at the treatment site within the patient, the outer wall defining a chamber therein;
  introducing a hardenable media into the chamber, wherein the hardenable media cures from a liquid form to a hardened form having a static compression bending value of at least 90 lbs (ASTM F1717) in 20-100 minutes at temperature between 35° C. and 42° C.; and
  curing the hardenable media within the chamber of the implantable device at a temperature between 35° C. and 42° C. in 20-100 minutes to form the orthopedic device.

14. The method of forming an orthopedic device as in claim 13, wherein the positioning step comprises positioning the outer wall between two bone anchors.

15. The method of claim 14, further comprising:
  engaging a first of the two bone anchors with a first vertebra;
  engaging a second of the two bone anchors with a second vertebra;
  wherein curing the hardenable media within the chamber of the implantable device at a temperature between 35° C. and 42° C. in 20-100 minutes to form the orthopedic device fixes the first bone anchor to the second bone anchor and thereby fixes the first vertebra to the second vertebra.

16. The method of claim 15, wherein positioning the implantable device comprises passing the implantable device through a first portal of the first bone anchor and a second portal of the second bone anchor.

17. The method of claim 16, wherein introducing the hardenable media into the chamber inflates the implantable member such that a diameter of the implantable member is greater than the diameters of the first and second portals.

18. The method of claim 13, wherein said hardenable media comprises about 45-52% by weight aromatic diepoxide resin, about 19-23% by weight aliphatic diepoxide resin, about 20-29% by weight dialkylamines and about 4-9% cycloalkylamines.

19. The method of claim 18, wherein the aromatic diepoxide resin comprises diglycidyl ether of Bisphenol A or diglycidyl ether of Bisphenol F; the aliphatic diepoxide resin comprises one or more alkane diols of glycidyl ether; the cycloalkylamines are N-aminoalkylpiperazines; and the dialkylamines are according to the formula H2N—R—NH2, wherein R is a branched or unbranched C2-C10 alkyl group.

20. The method of claim 18, wherein the aromatic diepoxide resin comprises diglycidyl ether of Bisphenol A, the aliphatic diepoxide resin comprises butane diol of glycidyl ether, the dialkylamine comprises 1,3-diaminopropane, and the cycloalkylamine comprises N-aminoethylpiperazine.

21. The method of claim 13, wherein the hardenable media has a static compression bending value (ASTM F1717) of at least 150 lbs within 12 hours.

22. A formed in place medical device, comprising:
  an inflatable spinal rod having an outer wall and defining a cavity therein; and
  a hardenable media positionable within the cavity to form the medical device, said hardenable media comprising a resin and hardener mixture that cures at a temperature below 45° C. in 100 minutes or less;
  wherein said cured media has a static compression bending value (ASTM F 1717) of at least 150 lbs;
  wherein the hardenable media is hardened while the device is positioned within the body of a patient to create the formed in place medical device.

23. The formed in place medical device of claim 22, further comprising a pair of bone anchors having portals for receiving the inflatable spinal rod, each of the pair of bone anchors having a bone-engaging portion for fixedly engaging with a vertebra.

* * * * *